United States Patent
Ledeboer et al.

(10) Patent No.: US 7,361,665 B2
(45) Date of Patent: Apr. 22, 2008

(54) INHIBITORS OF C-JUN N-TERMINAL KINASES (JNK) AND OTHER PROTEIN KINASES

(75) Inventors: Mark Ledeboer, Acton, MA (US); Jian Wang, Boston, MA (US); Young Choon Moon, Belle Mead, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 321 days.

(21) Appl. No.: 10/616,560

(22) Filed: Jul. 9, 2003

(65) Prior Publication Data

US 2004/0097531 A1 May 20, 2004

Related U.S. Application Data

(60) Provisional application No. 60/395,202, filed on Jul. 9, 2002.

(51) Int. Cl.
C07D 409/04 (2006.01)
A61K 31/506 (2006.01)
(52) U.S. Cl. ..................... 514/275; 544/331
(58) Field of Classification Search ............... 544/331; 514/275
See application file for complete search history.

(56) References Cited

FOREIGN PATENT DOCUMENTS

| EP | 1 180 518 A | 2/2002 |
|---|---|---|
| WO | WO 01/30778 A | 5/2001 |
| WO | WO 01/72745 A | 10/2001 |
| WO | WO 02/064586 A | 8/2002 |
| WO | WO 02/083111 | * 10/2002 |
| WO | WO 03/015776 A | 2/2003 |
| WO | WO 03/076434 A | 9/2003 |

OTHER PUBLICATIONS

Sah et al., Translation Inhibitors Sensitize Prostate Cancer Cells to Apoptosis Induced by TNF-related Apoptosis-inducing ligand (TRAIL) by activating c-Jun N-terminal kinase, The Journal of Biological Chemistry, vol. 278, No. 23, pp. 20593-20602, 2003.*
Casanova et al., PubMed Abstract (Rev Neurol. 28(9):909-15), May 1-15, 1999.*
Tanaka et al., PubMed Abstract (Cell 108(3):317-29) Feb. 8, 2002.*
Rogers et al., PubMed Abstract (J Cell Biol. 157(2):219-29) Apr. 2002.*
Layzer, Degenerative Diseases of the Nervous System, Cecil Textbook of Medicine, 20th Edition, vol. 2, pp. 2050-2057, 1996.*
Simone, Oncology: Introduction, Cecil Textbook of Medicine, 20th Edition, vol. 1, pp. 1004-1010, 1996.*
Damasio, Alzheimer's Disease and related Dementias, Cecil Textbook of Medicine, 20th Edition, vol. 2, pp. 1992-1996, 1996.*
Douglas, Jr. Introduction to Viral Diseases, Cecil Textbook of Medicine, 20th Edition, vol. 2, pp. 1739-1747, 1996.*
Christopher A. Lipinski et al., "Bioisosteric Prototype Design of Biaryl Imidazoyl and Triazoyl Competitive Histamine $H_2$-Receptor Antagonists", J. Med. Chem., 29, 2154-2163 (1986).

* cited by examiner

Primary Examiner—Deepak Rao
(74) Attorney, Agent, or Firm—Karen E. Brown

(57) ABSTRACT

The present invention provides compounds of formula I:

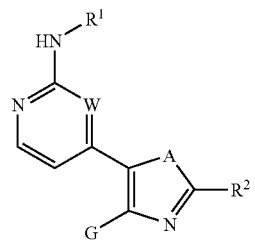

or a pharmaceutically acceptable derivative thereof, wherein $R^1$, $R^2$, A, G, and W are as described in the specification. These compounds are inhibitors of protein kinase, particularly inhibitors of JNK, a mammalian protein kinase involved cell proliferation, cell death and response to extracellular stimuli, Lck, Src, and Aurora kinases. The invention also relates to methods for producing these inhibitors. The invention also provides pharmaceutical compositions comprising the inhibitors of the invention and methods of utilizing those compositions in the treatment and prevention of various disorders.

12 Claims, No Drawings

SEQUENCE LISTING

<160> NUMBER OF SEQ ID NOS: 3

<210> SEQ ID NO 1
<211> LENGTH: 39
<212> TYPE: DNA
<213> ORGANISM: Artificial
<220> FEATURE:
<223> OTHER INFORMATION: forward primer JNK3

<400> SEQUENCE: 1
gctctagagc tccatgggca gcaaaagcaa agttgacaa                        39

<210> SEQ ID NO 2
<211> LENGTH: 37
<212> TYPE: DNA
<213> ORGANISM: Artificial
<220> FEATURE:
<223> OTHER INFORMATION: Reverse Primer for JNK3

<400> SEQUENCE: 2
tagcggatcc tcattctgaa ttcattactt ccttgta                          37

<210> SEQ ID NO 3
<211> LENGTH: 21
<212> TYPE: PRT
<213> ORGANISM: Artificial
<220> FEATURE:
<223> OTHER INFORMATION: EGF receptor peptide

<400> SEQUENCE: 3

Lys Arg Glu Leu Val Glu Pro Leu Thr Pro Ser Gly Glu Ala Pro Asn
1               5                   10                  15

Gln Ala Leu Leu Arg
            20

INHIBITORS OF C-JUN N-TERMINAL KINASES (JNK) AND OTHER PROTEIN KINASES

CROSS REFERENCE TO RELATED APPLICATIONS

This application claims priority to U.S. Provisional Patent Application 60/395,202, filed Jul. 9, 2002, which is hereby incorporated by reference in its entirety.

TECHNICAL FIELD OF THE INVENTION

The present invention relates to inhibitors of protein kinase, especially c-Jun N-terminal kinases (JNK) the Src-family of kinases, including Lck, which are members of the mitogen-activated protein (MAP) kinase family, and the Aurora family, including Aurora-2, which are serine/threonine kinases. JNK, Src, Lck, and Aurora-2 have been implicated in a number of different human diseases. The invention also provides pharmaceutical compositions comprising the inhibitors of the invention and methods of utilizing those compositions in the treatment and prevention of various disorders in which JNK, Src, Lck, and/or Aurora-2 kinases play a role.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occurs by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One particularly interesting kinase family are the c-Jun $NH_2$-terminal protein kinases, also known as JNKs. Three distinct genes, JNK1, JNK2, JNK3 have been identified and at least ten different splicing isoforms of JNKs exist in mammalian cells [Gupta et al., *EMBO J.*, 15:2760-70 (1996)]. Members of the JNK family are activated by proinflammatory cytokines, such as tumor necrosis factor-α (TNFα) and interleukin-1β (IL-1β), as well as by environmental stress, including anisomycin, UV irradiation, hypoxia, and osmotic shock [Minden et al., *Biochemica et Biophysica Acta*, 1333:F85-F104 (1997)].

The down-stream substrates of JNKs include transcription factors c-Jun, ATF-2, Elk1, p53 and a cell death domain protein (DENN) [Zhang et al. *Proc. Natl. Acad. Sci. USA*, 95:2586-91 (1998)]. Each JNK isoform binds to these substrates with different affinities, suggesting a regulation of signaling pathways by substrate specificity of different JNKs in vivo [Gupta et al., supra].

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21:326-9 (1999); *FEBS Lett.* 420:201-4 (1997); *J. Clin. Invest.* 102:1942-50 (1998); and *Hepatology* 28:1022-30 (1998)]. Therefore, inhibitors of JNK may be useful to treat various hepatic disorders.

A role for JNK in cardiovascular disease such as myocardial infarction or congestive heart failure has also been reported as it has been shown that JNK mediates hypertrophic responses to various forms of cardiac stress [*Circ. Res.* 83:167-78 (1998); *Circulation* 97:1731-7 (1998); *J. Biol. Chem.* 272:28050-6 (1997); *Circ. Res.* 79:162-73 (1996); *Circ. Res.* 78:947-53 (1996); and *J. Clin. Invest.* 97:508-14 (1996)].

It has also been demonstrated that the JNK cascade plays a role in T-cell activation, including activation of the IL-2 promoter. Thus, inhibitors of JNK may have therapeutic value in altering pathologic immune responses [*J. Immunol.* 162:3176-87 (1999); *Eur. J. Immunol.* 28:3867-77 (1998); *J. Exp. Med.* 186:941-53 (1997); and *Eur. J. Immunol.* 26:989-94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13:135-42 (1996)]. JNK may play a role in Kaposi's sarcoma (KS) because it is thought that the proliferative effects of bFGF and OSM on KS cells are mediated by their activation of the JNK signaling pathway [*J. Clin. Invest.* 99:1798-804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92:2450-60 (1998)].

JNK1 and JNK2 are widely expressed in a variety of tissues. In contrast, JNK3 is selectively expressed in the brain and to a lesser extent in the heart and testis [Gupta et al., supra; Mohit et al., *Neuron* 14:67-78 (1995); and Martin et al., *Brain Res. Mol. Brain Res.* 35:47-57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity [Yang et al., *Nature*, 389:865-870 (1997)].

Based on these findings, JNK signaling, especially that of JNK3, has been implicated in the areas of apoptosis-driven neurodegenerative diseases such as Alzheimer's disease, Parkinson's disease, ALS (amyotrophic lateral sclerosis), epilepsy and seizures, Huntington's disease, traumatic brain injuries, as well as ischemic and hemorrhaging stroke.

The Src-family of kinases are implicated in cancer, immune system dysfunction, and bone remodeling diseases. For general reviews, see Thomas and Brugge, *Annu. Rev. Cell Dev. Biol.* 13:513 (1997); Lawrence and Niu, *Pharmacol. Ther.* 77:81 (1998); Tatosyan and Mizenina, *Biochemistry* (Moscow) 65:49 (2000); and Boschelli et al., *Drugs of the Future* 2000, 25(7):717 (2000).

Members of the Src family include the following eight kinases in mammals: Src, Fyn, Yes, Fgr, Lyn, Hck, Lck, Blk and Yrc. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region [Tatosyan et al. *Biochemistry* (Moscow) 65:49-58 (2000)].

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src [Soriano et al., *Cell*, 69:551 (1992) and Soriano et al., *Cell*, 64: 693 (1991)].

Suppression of arthritic bone destruction has been achieved by the overexpression of CSK in rheumatoid synoviocytes and osteoclasts [Takayanagi et al., *J. Clin. Invest.*, 104:137 (1999)]. CSK, or C-terminal Src kinase, phosphorylates and thereby inhibits Src catalytic activity. This implies that Src inhibition may prevent joint destruction that is characteristic in patients suffering from rheumatoid arthritis [Boschelli et al., *Drugs of the Future* 2000, 25(7):717 (2000)].

Src also plays a role in the replication of hepatitis B virus. The virally encoded transcription factor HBx activates Src in a step required for propagation of the virus [Klein et al., *EMBO J.*, 18:5019, (1999) and Klein et al., *Mol. Cell. Biol.*, 17:6427 (1997)].

A number of studies have linked Src expression to cancers such as colon, breast, hepatic and pancreatic cancer, certain B-cell leukemias and lymphomas [Talamonti et al., *J. Clin. Invest.*, 91:53 (1993); Lutz et al., *Biochem. Biophys. Res.* 243:503 (1998); Rosen et al., *J. Biol. Chem.*, 261:13754 (1986); Bolen et al., *Proc. Natl. Acad. Sci. USA*, 84:2251 (1987); Masaki et al., *Hepatology*, 27:1257 (1998); Biscardi et al., *Adv. Cancer Res.*, 76:61 (1999); Lynch et al., *Leukemia*, 7:1416 (1993)]. Furthermore, antisense Src expressed in ovarian and colon tumor cells has been shown to inhibit tumor growth [Wiener et al., *Clin. Cancer Res.*, 5:2164 (1999) and Staley et al., *Cell Growth Diff.*, 8:269 (1997)].

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis [Molina et al., *Nature*, 357: 161 (1992)]. Hck, Fgr and Lyn have been identified as important mediators of integrin signaling in myeloid leukocytes [Lowell et al., *J. Leukoc. Biol.*, 65:313 (1999)]. Inhibition of these kinase mediators may therefore be useful for treating inflammation [Boschelli et al., *Drugs of the Future* 2000, 25(7):717 (2000)].

The Aurora family of serine/threonine kinases is essential for cell proliferation [Bischoff, J. R. & Plowman, G. D. *Trends in Cell Biology et al.*, 9:454-459 (1999); Giet et al. *Journal of Cell Science*, 112:3591-3601 (1999); Nigg *Nat. Rev. Mol. Cell Biol.* 2:21-32 (2001); Adams et al., *Trends in Cell Biology* 11:49-54 (2001)]. Inhibitors of the Aurora kinase family therefore have the potential to block growth of all tumour types.

The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, Since its discovery in 1997 the mammalian Aurora kinase family has been closely linked to tumorigenesis. The most compelling evidence for this is that over-expression of Aurora-A transforms rodent fibroblasts [Bischoff et al., *EMBO J.*, 17:3052-3065 (1998)]. Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. [Miyoshi et al. *Int. J. Cancer*, 92:370-373 (2001) and Sakakura et al. *British Journal of Cancer*, 84:824-831 (2001)]. The Aurora kinases have been reported to be over-expressed in a wide range of human tumours. Elevated expression of Aurora-A has been detected in over 50% of colorectal [Bischoff et al., *EMBO J.*, 17:3052-3065 (1998) and Takahashi et al., *Jpn. J. Cancer Res.*, 91:1007-1014 (2000)] ovarian [Gritsko et al. *Clinical Cancer Research*, 9:1420-1426 (2003)], and gastric tumors [Sakakura et al., *British Journal of Cancer*, 84:824-831 (2001)], and in 94% of invasive duct adenocarcinomas of the breast [Tanaka et al. *Cancer Research*, 59:2041-2044 (1999)]. High levels of Aurora-A have also been reported in renal, cervical, neuroblastoma, melanoma, lymphoma, pancreatic and prostate tumour cell lines. [Bischoff et al., *EMBO J.*, 17:3052-3065 (1998); Kimura et al. *J. Biol. Chem.*, 274:7334-7340 (1999); Zhou et al., *Nature Genetics*, 20:189-193 (1998); Li et al., *Clin Cancer Res.* 9(3):991-7 (2003)]. Amplification/overexpression of Aurora-A is observed in human bladder cancers and amplification of Aurora-A is associated with aneuploidy and aggressive clinical behaviour [Sen et al., *J Natl Cancer Inst.*, 94(17):1320-9 (2002)]. Moreover, amplification of the aurora-A locus (20q13) correlates with poor prognosis for patients with node-negative breast cancer [Isola, *American Journal of Pathology* 147, 905-911 (1995)]. Aurora-B is highly expressed in multiple human tumour cell lines, including leukemic cells [Katayama et al., *Gene* 244:1-7)]. Levels of this enzyme increase as a function of Duke's stage in primary colorectal cancers [Katayama et al., *J. Natl Cancer Inst.*, 91:1160-1162 (1999)]. Aurora-C, which is normally only found in germ cells, is also over-expressed in a high percentage of primary colorectal cancers and in a variety of tumour cell lines including cervical adenocarinoma and breast carcinoma cells [Kimura et al., *J. Biol.*

Chem. 274:7334-7340 (1999) and Takahashi et al., *Jpn. J. Cancer Res.*, 91:1007-1014 (2000)].

Based on the known function of the Aurora kinases, inhibition of their activity should disrupt mitosis leading to cell cycle arrest. In vivo, an Aurora inhibitor therefore slows tumor growth and induces regression.

Elevated levels of all Aurora family members are observed in a wide variety of tumour cell lines. Aurora kinases are over-expressed in many human tumors and this is reported to be associated with chromosomal instability in mammary tumors.

Aurora-2 is highly expressed in multiple human tumor cell lines and levels increase as a function of Duke's stage in primary colorectal cancers [Katayama et al., *J. Natl Cancer Inst.*, 91:1160-1162 (1999)]. Aurora-2 plays a role in controlling the accurate segregation of chromosomes during mitosis. Misregulation of the cell cycle can lead to cellular proliferation and other abnormalities. In human colon cancer tissue, the Aurora-2 protein has been found to be over expressed [Bischoff et al., *EMBO J.*, 17: 3052-3065 (1998); Schumacher et al., *J. Cell Biol.*, 143:1635-1646 (1998); Kimura et al., *J. Biol. Chem.*, 272: 13766-13771 (1997)]. Aurora-2 is over-expressed in the majority of transformed cells. Bischoff et al found high levels of Aurora-2 in 96% of cell lines derived from lung, colon, renal, melanoma and breast tumors [Bischoff et al., *EMBO J.*, 17:3052-3065 (1998)]. Two extensive studies show elevated Aurora-2 in 54% and 68% [Bishoff et al., *EMBO J.*, 17:3052-3065 and Takahashi et al. *Jpn J Cancer Res.* 91:1007-1014 (2000)] of colorectal tumours and in 94% of invasive duct adenocarcinomas of the breast (Tanaka et al., *Cancer Research*, 59:2041-2044 (1999)].

Aurora-1 expression is elevated in cell lines derived from tumors of the colon, breast, lung, melanoma, kidney, ovary, pancreas, CNS, gastric tract and leukemias (Tatsuka et al 1998 58, 4811-4816).

High levels of Aurora-3 have been detected in several tumour cell lines, although it is restricted to testis in normal tissues [Kimura et al. *Journal of Biological Chemistry*, 274:7334-7340 (1999)]. Over-expression of Aurora-3 in a high percentage (c. 50%) of colorectal cancers has also been documented (Takahashi et al., *Jpn J. Cancer Res.* 91:1007-1014 (2001)]. In contrast, the Aurora family is expressed at a low level in the majority of normal tissues, the exceptions being tissues with a high proportion of dividing cells such as the thymus and testis [Bischoff et al *EMBO J.*, 17:3052-3065 (1998)].

For further review of the role Aurora kinases play in proliferative disorders, see Bischoff et al., *Trends in Cell Biology* 9:454-459 (1999); Giet et al. *Journal of Cell Science*, 112:3591-3601 (1999); Nigg et al., *Nat. Rev. Mol. Cell Biol.*, 2:21-32 (2001) et al., *Trends in Cell Biology*, 11:49-54 (2001); and Dutertre, et al. *Oncogene*, 21:6175-6183 (2002).

There is a continued need to develop potent inhibitors of JNKs, Src family kinases, and Aurora family kinases that are useful in treating or preventing various conditions associated with JNK, Src, and Aurora activation.

SUMMARY OF THE INVENTION

The present invention provides compounds of formula I:

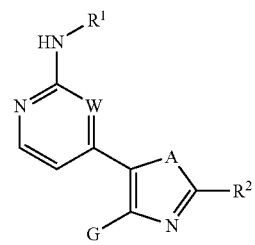

or a pharmaceutically acceptable derivative thereof, wherein $R^1$, $R^2$, A, G, and W are as described below.

The present invention also provides a pharmaceutical composition comprising a compound of formula I.

The compounds and pharmaceutical compositions of the present invention are useful as inhibitors of c-Jun N-terminal kinases (JNK) Src family kinases, including Src and Lck, and Aurora family kinases, including Aurora-2. Thus, they are also useful in methods for treating or preventing a variety of disorders, such as heart disease, immunodeficiency disorders, inflammatory diseases, allergic diseases, autoimmune diseases, destructive bone disorders such as osteoporosis, proliferative disorders, infectious diseases and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders.

DETAILED DESCRIPTION OF THE INVENTION

The present invention provides a compound of formula I:

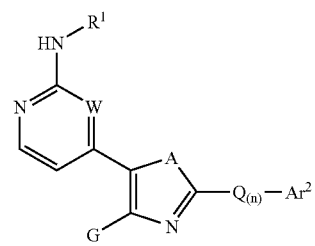

or a pharmaceutically acceptable derivative thereof, wherein:

W is nitrogen or CH;

G is hydrogen or $C_{1-3}$ aliphatic wherein one methylene unit of G is optionally replaced by —C(O)—, —C(O)O—, —C(O)NH—, —SO$_2$—, or —SO$_2$NH—;

A is —N-T$_{(n)}$—R, oxygen, or sulfur;

R$^1$ is selected from -T$_{(n)}$—R or -T$_{(n)}$—Ar$^1$;

each n is independently 0 or 1;

T is a C$_{1-4}$ alkylidene chain wherein one methylene unit of T is optionally replaced by —C(O)—, —C(O)O—, —C(O)NH—, —SO$_2$—, or —SO$_2$NH—;

Ar$^1$ is a 3-7 membered monocyclic saturated, partially saturated, or aromatic ring having 0-3 heteroatoms independently selected from nitrogen, oxygen, or sulfur, or a 8-10 membered bicyclic saturated, partially saturated, or aromatic ring having 0-5 heteroatoms independently selected from nitrogen, oxygen, or sulfur, wherein each member of Ar$^1$ is optionally substituted with one -Z-R$^3$ and one to three additional groups independently selected from —R, halogen, oxo, —NO$_2$, —CN, —OR, —SR, —N(R)$_2$, —NRC(O)R, —NRC(O)N(R)$_2$, —NRCO$_2$R, —C(O)R, —CO$_2$R, —OC(O)R, —C(O)N(R)$_2$, —OC(O)N(R)$_2$, —S(O)R, —SO$_2$R, —SO$_2$N(R)$_2$, —NRSO$_2$R, —NRSO$_2$N(R)$_2$, —C(O)C(O)R, or —C(O)CH$_2$C(O)R;

each R is independently selected from hydrogen or a C$_{1-6}$ aliphatic, wherein said aliphatic is optionally substituted with one to three groups independently selected from oxo, —CO$_2$R', —OR', —N(R')$_2$, —SR', —NO$_2$, —NR'C(O)R', —NR'C(O)N(R')$_2$, —NR'CO$_2$R', —C(O)R', —OC(O)R', —C(O)N(R')$_2$, —OC(O)N(R')$_2$, —S(O)R', —SO$_2$R', —SO$_2$N(R')$_2$, —NR'SO$_2$R', —NR'SO$_2$N(R')$_2$, —C(O)C(O)R', —C(O)CH$_2$C(O)R', halogen, or —CN, or two R bound to the same nitrogen atom are taken together with that nitrogen atom to form a five or six membered heterocyclic or heteroaryl ring having one to two additional heteroatoms independently selected from oxygen, nitrogen, or sulfur;

each R' is independently selected from hydrogen or C$_{1-6}$ aliphatic, wherein said aliphatic is optionally substituted with one to three groups independently selected from oxo, —CO$_2$H, —OH, —NH$_2$, —SH, —NO$_2$, —NHC(O)H, —NHC(O)NH$_2$, —NHCO$_2$H, —C(O)H, —OC(O)H, —C(O)NH$_2$, —OC(O)NH$_2$, —S(O)H, —SO$_2$H, —SO$_2$NH$_2$, —NHSO$_2$H, —NHSO$_2$NH$_2$, —C(O)C(O)H, —C(O)CH$_2$C(O)H, halogen, or —CN, or two R' bound to the same nitrogen atom are taken together with that nitrogen atom to form a five or six membered heterocyclic or heteroaryl ring optionally having one or two additional heteroatoms independently selected from nitrogen, oxygen, or sulfur;

Z is a C$_1$-C$_6$ alkylidene chain wherein up to two nonadjacent methylene units of Z are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO$_2$—, —N(R)SO$_2$—, —SO$_2$N(R)—, —N(R)SO$_2$N(R)—, —O—, —S—, or —N(R)—;

R$^2$ is -Q$_{(n)}$-Ar$^2$;

Ar$^2$ is selected from a 3-7 membered monocyclic saturated, partially saturated, or aromatic ring having 0-3 heteroatoms independently selected from nitrogen, oxygen, or sulfur, or a 8-10 membered bicyclic saturated, partially saturated, or aromatic ring having 0-5 heteroatoms independently selected from nitrogen, oxygen, or sulfur, wherein each member of Ar$^2$ is optionally substituted with 1-5 groups independently selected from -Z-R$^3$, —R, halogen, oxo, —NO$_2$, —CN, —OR, —SR, —N(R)$_2$, —NRC(O)R, —NRC(O)N(R)$_2$, —NRCO$_2$R, —C(O)R, —CO$_2$R, —OC(O)R, —C(O)N(R)$_2$, —OC(O)N(R)$_2$, —S(O)R, —SO$_2$R, —SO$_2$N(R)$_2$, —N(R)SO$_2$R, —N(R)SO$_2$N(R)$_2$, —C(O)C(O)R, or —C(O)CH$_2$C(O)R;

Q is a C$_{1-3}$ alkylidene chain wherein up to two non-adjacent methylene units of Q are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO$_2$—, —N(R)SO$_2$—, —SO$_2$N(R)—, —N(R)SO$_2$N(R)—, —O—, —S—, or —N(R)—;

R$^3$ is selected from —Ar$^3$, —R, halogen, —NO$_2$, —CN, —OR, —SR, —N(R)$_2$, —NRC(O)R, —NRC(O)N(R)$_2$, —NRCO$_2$R, —C(O)R, —CO$_2$R, —OC(O)R, —C(O)N(R)$_2$, —OC(O)N(R)$_2$, —SOR, —SO$_2$R, —SO$_2$N(R)$_2$, —NRSO$_2$R, —NRSO$_2$N(R)$_2$, —C(O)C(O)R, or —C(O)CH$_2$C(O)R; and Ar$^3$ is a 5-6 membered saturated, partially saturated, or aromatic ring having 0-3 heteroatoms independently selected from nitrogen, oxygen, or sulfur, wherein each member of Ar$^3$ is optionally substituted with halogen, oxo, —CN, —NO$_2$, —R', —OR', —N(R')$_2$, —N(R')C(O)R', —N(R')C(O)N(R')$_2$, —N(R')CO$_2$R', —C(O)R', —CO$_2$R', —OC(O)R', —C(O)N(R')$_2$, —OC(O)N(R')$_2$, or —SO$_2$R';

provided that when W is nitrogen and:
(i) A is —N-T$_{(n)}$—R and R$^2$ is a saturated ring or
(ii) A is sulfur,
then R$^1$ is other than an optionally substituted phenyl.

The following abbreviations are used throughout the specifications (including in chemical formulae):

iPr=isopropyl
t-Bu or tBu=tert-butyl
Et=ethyl
Me=methyl
Cbz=benzoyloxycarbonyl
BOC=tert-butyloxycarbonyl
Ph=phenyl
Bn=benzyl
DMF=N,N-dimethylformamide THF=tetrahydrofuran
DCM=dichloromethane
MOM=methoxymethyl
DMSO=dimethylsulfoxide
TLC=thin layer chromatography As used herein, the following definitions shall apply unless otherwise indicated.

The phrase "optionally substituted" is used interchangeably with the phrase "substituted or unsubstituted". Unless otherwise indicated, an optionally substituted group may have a substituent at each substitutable position of the group, and each substitution is independent of each other.

The term "aliphatic" or "aliphatic group" as used herein means a straight-chain or branched C$_1$-C$_{12}$ hydrocarbon chain that is completely saturated or that contains one or more units of unsaturation, or a monocyclic C$_3$-C$_8$ hydrocarbon or bicyclic C$_8$-C$_{12}$ hydrocarbon ring system that is completely saturated or that contains one or more units of unsaturation, but which is not aromatic (also referred to herein as "carbocycle", "carbocyclic", "carbocyclo", or "cycloalkyl"), that has a single point of attachment to the rest of the molecule wherein any individual ring in said bicyclic ring system has 3-7 members. For example, suitable aliphatic groups include, but are not limited to, linear or branched alkyl, alkenyl or alkynyl groups and hybrids thereof such as (cycloalkyl)alkyl, (cycloalkenyl)alkyl or (cycloalkyl)alkenyl.

The terms "alkyl", "hydroxyalkyl" and "alkoxyalkyl", used alone or as part of a larger moiety, unless otherwise indicated, include both straight and branched saturated hydrocarbon chains containing one to twelve carbon atoms.

The term "alkenyl" used alone or as part of a larger moiety shall include both straight and branched hydrocarbon chains containing two to twelve carbon atoms and having at least one carbon-carbon double bond. The term "alkynyl" used alone or as part of a larger moiety shall include both straight and branched hydrocarbon chains containing two to twelve carbon atoms and having at least one carbon-carbon triple bond. The term "alkoxy" used alone or as part of a larger moiety refers to an —O-alkyl, —O-alkenyl, or —O-alkynyl radical.

The term "carbocycle", "carbocyclyl", "carbocyclo" or "carbocyclic" also includes hydrocarbon rings that are fused to one or more aromatic or nonaromatic rings, such as in a decahydronaphthyl or tetrahydronaphthyl, where the radical or point of attachment is on the aliphatic ring.

The terms "haloalkyl", "haloalkenyl" and "haloalkoxy" mean alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen. As an example, in a saturated or partially saturated ring having 0-3 heteroatoms selected from oxygen, sulfur or nitrogen, the nitrogen may be N (as in 3,4-dihydro-2H-pyrrolyl), NH (as in pyrrolidinyl) or NR+(as in N-substituted pyrrolidinyl).

The term "aryl" used alone or as part of a larger moiety as in "aralkyl", "aralkoxy", or "aryloxyalkyl", refers to monocyclic, bicyclic or tricyclic aromatic hydrocarbon ring systems having a total of five to fourteen ring members, such as phenyl, benzyl, phenethyl, 1-naphthyl, 2-naphthyl, 1-anthracyl and 2-anthracyl. The term "aryl" may be used interchangeably with the term "aryl ring". The term "aryl" also refers to rings that are optionally substituted. "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "aralkyl" refers to an alkyl, alkenyl or alkynyl group substituted by an aryl. Examples of aralkyl groups include, but are not limited to, benzyl and phenethyl. The term "aralkoxy" refers to an alkoxy group substituted by an aryl. The term "aryloxyalkyl" refers to an alkyl, alkenyl or alkynyl group substituted by an —O-aryl.

The term "heterocycle", "heterocyclyl", or "heterocyclic" as used herein includes non-aromatic monocyclic, bicyclic or tricyclic ring systems having five to fourteen ring members, preferably five to ten, in which one or more ring members is a heteroatom, wherein each ring in the system contains 3 to 7 ring members.

Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially saturated, also refers to rings that are optionally substituted. The term "heterocyclylalkyl" refers to an alkyl, alkenyl or alkynyl group substituted by a heterocyclyl.

The term "heteroaryl", used alone or as part of a larger moiety as in "heteroaralkyl" or "heteroarylalkoxy", refers to monocyclic, bicyclic or tricyclic heteroaromatic ring systems having five to fourteen members, preferably five to ten, wherein each ring in the system contains 3 to 7 ring members in which one or more ring carbons, preferably one to four, are each replaced by a heteroatom. The term "heteroaryl" may be used interchangeably with the term "heteroaryl ring" or the term "heteroaromatic". The term "heteroaryl" also refers to rings that are optionally substituted.

Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl.

Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaralkyl" refers to an alkyl, alkenyl or alkynyl group substituted by a heteroaryl. The term "heteroarylalkoxy" refers to an alkoxy group substituted by a heteroaryl.

An aryl (including the aryl moiety in aralkyl, aralkoxy, aryloxyalkyl and the like) or heteroaryl (including the heteroaryl moiety in heteroaralkyl and heteroarylalkoxy and the like) group may contain one or more substituents. Determination of a suitable number of substituents on any given moiety is within the understanding of the skilled artisan. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, phenyl (Ph) optionally substituted with R°, —O(Ph) optionally substituted with R°, —CH$_2$(Ph) optionally substituted with R°, —CH$_2$CH$_2$(Ph) optionally substituted with R°, —NO$_2$, —CN, —N(R°)$_2$, —NR°C(O)R°, —NR°C(O)N(R°)$_2$, —NR'CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —OC(O)R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C (=S)N (R°)$_2$, —C (=NH)—N(R°)$_2$, or —(CH$_2$)$_y$NHC(O)R°, wherein y is 1-4 and each R° is independently selected from hydrogen, optionally substituted C$_{1-6}$ aliphatic, an unsubstituted 5-6 membered heteroaryl or heterocyclic ring, phenyl, —O(Ph), or —CH$_2$(Ph). Optional substituents on the aliphatic group of R° are selected from —NH$_2$, —NH(C$_{1-4}$ unsubstituted aliphatic), —N(C$_{1-4}$ unsubstituted aliphatic)$_2$, halogen, —C$_{1-4}$ unsubstituted aliphatic, —OH, —O(C$_{1-4}$ unsubstituted aliphatic), —NO$_2$, —CN, —CO$_2$H, —CO$_2$(C$_{1-4}$ unsubstituted aliphatic), —O(halo C$_{1-4}$ unsubstituted aliphatic), or halo C$_{1-4}$ unsubstituted aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from —NH$_2$, —NH(C$_{1-4}$ unsubstituted aliphatic), —N(C$_{1-4}$ unsubstituted aliphatic)$_2$, halogen, C$_{1-4}$ unsubstituted aliphatic, —OH, —O(C$_{1-4}$ unsubstituted aliphatic), —NO$_2$, —CN, —CO$_2$H, —CO$_2$(C$_{1-4}$ unsubstituted aliphatic), —O(halo C$_{1-4}$ unsubstituted aliphatic), or halo(C$_{1-4}$ unsubstituted aliphatic).

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —CH$_2$CH$_2$(Ph), or an unsubstituted 5-6 membered heteroaryl or heterocyclic ring. Optional substituents on the aliphatic group or the phenyl ring of R$^+$ are selected from —NH$_2$, —NH(C$_{1-4}$ unsubstituted aliphatic), N(C$_{1-4}$ unsubstituted aliphatic)$_2$, halogen, C$_{1-4}$ unsubstituted aliphatic, —OH, —O(C$_{1-4}$ unsubstituted aliphatic), —NO$_2$, —CN, —CO$_2$H, —CO$_2$(C$_{1-4}$ unsubstituted aliphatic), —O(halo C$_{1-4}$ unsubstituted aliphatic), or halo(C$_{1-4}$ unsubstituted aliphatic).

The term "alkylidene chain" refers to a straight or branched carbon chain that may be fully saturated or have one or more units of unsaturation.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Preferred R$^1$ groups of formula I are selected from hydrogen, Ar$^1$ or -T-Ar$^1$ wherein T is a C$_{1-4}$ alkylidene chain and Ar$^1$ is an optionally substituted 6-membered saturated, partially saturated, or aryl ring having zero to two heteroatoms independently selected from nitrogen, oxygen, or sulfur. More preferred R$^1$ groups of formula I are selected from phenyl, benzyl, pyridyl, piperidinyl, or cyclohexyl. Preferred substituents on R$^1$ are selected from —CO$_2$R, —OR, -Z-R$^3$, halogen, —NRSO$_2$R, —SO$_2$N(R)$_2$, —NRCON(R)$_2$, —NO$_2$, or —N(R)$_2$. More preferred substituents of R$^1$ are selected from benzyloxy, phenoxy, —SO$_2$NH$_2$, —OH, —NO$_2$, —NH$_2$, —OMe, —Br, —Cl, —CO$_2$Me, —NHSO$_2$Me, —NHSO$_2$Et, —NHCON(Me)$_2$, —NHCON(Et)$_2$, —NHCOpyrrolidin-1-yl, or —NHCOmorpholin-4-yl.

Most preferred R$^1$ groups of formula I are those wherein R$^1$ is —CH$_2$—Ar$^1$ or Ar$^1$. Preferred -Z-R$^3$ groups of the Ar$^1$ group of formula I are those wherein Z is a C$_{1-4}$ alkylidene chain wherein one methylene unit of Z is optionally replaced by —O—, —NH—, —NHC(O)—, —NHC(O)O—, —NHSO$_2$—, —C(O)NH—, and wherein R$^3$ is selected from —N(R)$_2$, —NHC(O)R, or Ar$^3$ wherein Ar$^3$ is a 5-6 membered heterocyclic or heteroaryl ring having one to two heteroatoms independently selected from nitrogen, oxygen, or sulfur. The Ar$^3$ group is optionally substituted with —R', —OR', —N(R')$_2$, or oxo. More preferred Z-R$^3$ groups of the Ar$^1$ group of formula I are selected from —O—CH$_2$-phenyl, —O(CH$_2$)$_3$OH, —O(CH$_2$)$_3$NH(CH$_2$)$_2$OH, —O(CH$_2$)$_2$NH(CH$_2$)$_2$OH, —O(CH$_2$)$_3$N(hydroxyethyl) (methyl), —O(CH$_2$)$_3$pyrrolidin-1-yl, —O(CH$_2$)$_2$morpholin-4-yl, —O(CH$_2$)$_3$N(Me)$_2$, —O(CH$_2$)$_3$N(Et)$_2$, —O(CH$_2$)$_3$(4-hydroxyethyl piperazin-1-yl), —O(CH$_2$)$_3$piperazin-1-yl, —O(CH$_2$)$_3$ (4-hydroxymethylpiperidin-1-yl), —O(CH$_2$)$_3$(4-hydroxypiperidin-1-yl), —NHCO(CH$_2$)$_3$N(Me)$_2$, —NHCO(CH$_2$)$_3$NCOCH$_3$, —NHCOCH$_2$pyridin-2-yl, —NHCOCH$_2$(2-aminothiazol-4-yl), —NHCOCH$_2$cyclopropyl, —NHCO(CH$_2$)$_2$N(Et)$_2$, —NHCO(CH$_2$)$_2$-(piperazin-2,5-dione-3-yl), —NHC(O)-pyrrolidin-1-yl, —NHCOmorpholin-4-yl, —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl.

Preferred R$^2$ groups of formula I are selected from Ar$^2$ or —CH$_2$—Ar$^2$ wherein Ar$^2$ is selected from 5-6 membered ring selected from carbocyclic, aryl, or a heterocyclyl or heteroaryl ring having one to two heteroatoms independently selected from nitrogen, oxygen or sulfur, wherein Ar$^2$ is optionally substituted with one to five groups independently selected from -Z-R$^3$, —R, halogen, —NO$_2$, —CN, —OR, —SR, —N(R)$_2$, —NRC(O)R, —NRC(O)N(R)$_2$, —NRCO$_2$R, —C(O)R, —CO$_2$R, —C(O)N(R)$_2$, —OC(O)N(R)$_2$, —S(O)R, —SO$_2$R, —SO$_2$N(R)$_2$, —N(R)SO$_2$R, —N(R)SO$_2$N(R)$_2$, —C(O)C(O)R, or —C(O)CH$_2$C(O)R. More preferred R$^2$ groups of formula I are selected from phenyl, pyridyl, pyrimidinyl, cyclohexyl, piperidinyl, furanyl, or benzyl. Preferred Z is a C$_{1-4}$ alkylidene chain and wherein one methylene unit of Z is optionally replaced by —S—, —O—, —N(R)—, or —C(O)O—. Preferred substituents on Ar$^2$ are selected from -Z-Ar$^3$, —R, halogen, —OR, —N(R)$_2$, or —CO$_2$R, wherein Ar$^3$ is an optionally substituted 5-6 membered aryl ring having zero to two heteroatoms independently selected from nitrogen, oxygen, or sulfur. More preferred substituents on Ar$^2$ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen such as chloro, bromo, and fluoro, haloalkyl such as trifluoromethyl, —OH, —NH$_2$, alkyl such as methyl, or alkoxy such as methoxy and ethoxy.

Preferred G is hydrogen, $C_{1-3}$ aliphatic, or $C_1$-$C_3$ aliphatic wherein one methylene unit of G is replaced by —C(O)—. More preferred G is hydrogen.

Preferred A is —NH, —N—$CH_3$, —N—$CH_2$—$OCH_3$, oxygen, or sulfur.

One embodiment of this invention relates to compounds of formula Ia:

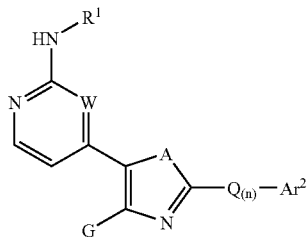

Ia or a pharmaceutically acceptable derivative thereof, wherein $R^1$, R, T, W, A, Q, $Ar^2$ and G are as described above. Preferred $R^1$, $Ar^2$, A, and G are as described above for formula. I.

Preferred Q is a $C_1$-$C_3$ alkylidene chain; or a $C_1$-$C_3$ alklyidene chain with one methylene unit replaced by —O—.

Another embodiment of this invention relates to compounds of formula IIa:

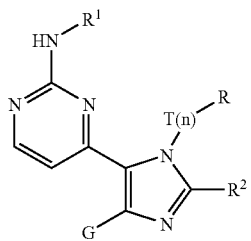

IIa or a pharmaceutically acceptable derivative thereof, wherein $R^1$, $R^2$, R, T, and G are as described above.

Preferred $R^1$ groups of formula IIa are selected from hydrogen, $Ar^1$ or -T-$Ar^1$ wherein T is a $C_{1-4}$ alkylidene chain wherein one —$CH_2$— unit of T is optionally replaced by —C(O)—, —C(O)O—, —C(O)NH—, —$SO_2$— or —$SO_2$NH—, and $Ar^1$ is an optionally substituted 6-membered saturated, partially saturated, or aryl ring having zero to two heteroatoms independently selected from nitrogen, oxygen, or sulfur. More preferred $R^1$ groups of formula IIa are selected from phenyl, benzyl, pyridyl, piperidinyl, or cyclohexyl. Preferred substituents on $R^1$ are selected from —$CO_2R$, —OR, -Z-$R^3$, halogen, —$NRSO_2R$, —$SO_2N(R)_2$, —$NRCON(R)_2$, —$NO_2$, or —$N(R)_2$. More preferred substituents of $R^1$ are selected from benzyloxy, phenoxy, —$SO_2NH_2$, —OH, —$NO^2$, —$NH_2$, —OMe, —Br, —Cl, —$CO_2Me$, —$NHSO_2Me$, —$NHSO_2Et$, —$NHCON(Me)_2$, —$NHCON(Et)_2$, —NHCOpyrrolidin-1-yl, or —NHCOmorpholin-4-yl.

Preferred $R^2$ groups of formula IIa are selected from $Ar^2$ or —$CH_2$—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, wherein $Ar^2$ is optionally substituted with one to five groups independently selected from -Z-$R^3$, —R, halogen, —$NO_2$, —CN, —OR, —SR, —$N(R)_2$, —NRC(O)R, —NRC(O)N($R)_2$, —$NRCO_2R$, —C(O)R, —$CO_2R$, —C(O)N($R)_2$, —OC(O)N(R)$_2$, —S(O)R, —$SO_2R$, —$SO_2N(R)_2$, —N(R)$SO_2R$, —N(R)$SO_2N(R)_2$, —C(O)C(O)R, or —C(O)$CH_2$C(O)R. More preferred $R^2$ groups of formula IIa are selected from phenyl, pyridyl, pyrimidinyl, cyclohexyl, piperidinyl, furanyl, or benzyl. Preferred Z is a $C_{1-4}$ alkylidene chain and wherein one methylene unit of Z is optionally replaced by —S—, —O—, —N(R)—, or —C(O)O—. Preferred substituents on $Ar^2$ are selected from -Z-$Ar^3$, —R, halogen, —OR, —$N(R)_2$, or —$CO_2R$, wherein $Ar^3$ is an optionally substituted 5-6 membered aryl ring having zero to two heteroatoms independently selected from nitrogen, oxygen, or sulfur. More preferred substituents on $Ar^2$ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen such as chloro, bromo, and fluoro, haloalkyl such as trifluoromethyl, —OH, —$NH_2$, alkyl such as methyl, or alkoxy such as methoxy and ethoxy.

Preferred G is hydrogen, $C_{1-3}$ aliphatic, or $C_1$-$C_3$ aliphatic wherein one methylene unit of G is replaced by —C(O)—. More preferred G is hydrogen.

Preferred compounds of formula IIa are those having one or more, more preferably more than one, and most preferably all, of the features selected from the group consisting of:

(a) $R^1$ is hydrogen, $Ar^1$ or -T-$Ar^1$ wherein T is a $C_{1-4}$ alkylidene chain and $Ar^1$ is a 6-membered saturated, partially saturated, or aryl ring having zero to two heteroatoms independently selected from nitrogen, oxygen, or sulfur, and wherein each member of $R^1$ is optionally substituted with one -Z-$R^3$ and one to three additional groups independently selected from —$CO_2R$, —OR, halogen, —$NRSO_2R$, —$SO_2N(R)_2$, —$NRCON(R)_2$, —$NO_2$, or —$N(R)_2$;

(b) $R^2$ is $Ar^2$ or —$CH_2$—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted with one to five groups independently selected from -Z-$R^3$, —R, halogen, —$NO_2$, —CN, —OR, —SR, —$N(R)_2$, —NRC(O)R, —NRC(O)N($R)_2$, —$NRCO_2R$, —C(O)R, —$CO_2R$, —C(O)N($R)_2$, —OC(O)N($R)_2$, —S(O)R, —$SO_2R$, —$SO_2N(R)_2$, —N(R)$SO_2R$, —N(R)$SO_2N(R)_2$, —C(O)C(O)R, or —C(O)$CH_2$C(O)R; and (c) G is hydrogen.

More preferred compounds of formula IIa are those having one or more, more preferably more than one, and most preferably all, of the features selected from the group consisting of:

(a) $R^1$ is selected from a phenyl, benzyl, pyridyl, piperidinyl, or cyclohexyl ring, wherein said ring is optionally substituted with benzyloxy, phenoxy, —$SO_2NH_2$, —OH, —$NO_2$, —$NH_2$, —OMe, —Br, —Cl, —$CO_2Me$, —$NHSO_2Me$, —$NHSO_2Et$, —NHCON(Me)$_2$, —NHCON(Et)$_2$, —NHCOpyrrolidin-1-yl, —NHCOmorpholin-4-yl, —O—$CH_2$-phenyl, —O($CH_2)_3$OH, —O($CH_2)_3$NH($CH_2)_2$OH, —O($CH_2)_2$NH($CH_2)_2$OH, —O($CH_2)_3$N(hydroxyethyl) (methyl), —O(CH$_2$)$_3$pyrrolidin-1-yl, —O(CH$_2$)$_2$morpholin-4-yl, —O(CH$_2$)$_3$N(Me)$_2$, —O(CH$_2$)$_3$N(Et)$_2$, —O(CH$_2$)$_3$(4-hydroxyethyl piperazin-1-yl), —O(CH$_2$)$_3$piperazin-1-yl, —O(CH$_2$)$_3$(4-hydroxymethylpiperidin-1-yl), —O(CH$_2$)$_3$(4-hydroxypiperidin-1-yl), —NHCO(CH$_2$)$_3$N(Me)$_2$, —NHCO(CH$_2$)$_3$NCOCH$_3$, —NHCOCH$_2$pyridin-2-yl, —NHCOCH$_2$(2-aminothiazol-4-yl), —NHCOCH$_2$cyclopropyl, —NHCO(CH$_2$)$_2$N(Et)$_2$, —NHCO(CH$_2$)$_2$-(piperazin-2,5-dione-3-yl), —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl;

(b) R$^2$ is selected from phenyl, pyridyl, pyrimidinyl, cyclohexyl, piperidinyl, furanyl, or benzyl, wherein R$^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —NH$_2$, methyl, methoxy, or ethoxy; and (c) G is hydrogen.

Exemplary compounds of formula IIa are shown below in Table 1.

TABLE 1

Compounds of Formula IIa

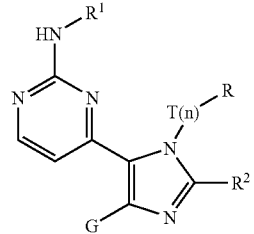

IIa

| No. IIa- | G | —T$_{(n)}$—R | R$^1$ | R$^2$ |
|---|---|---|---|---|
| 1 | H | H | 4-Cl-phenyl | Ph |
| 2 | H | H | 4-F-phenyl | Ph |
| 3 | H | H | 3-OMe-Ph | Ph |
| 4 | H | H | 3,5-(OMe)$_2$-Ph | Ph |
| 5 | H | CH$_3$ | 4-Cl-phenyl | pyridin-3-yl |
| 6 | H | CH$_3$ | 4-F-phenyl | pyridin-3-yl |
| 7 | H | CH$_3$ | Ph | pyridin-3-yl |
| 8 | H | CH$_3$ | 3-BnO-Ph | pyridin-3-yl |
| 9 | H | CH$_3$ | 6-Cl-pyridin-3-yl | pyridin-3-yl |
| 10 | H | CH$_2$OCH$_3$ | 4-Cl-phenyl | Ph |
| 11 | H | CH$_2$OCH$_3$ | 4-F-phenyl | Ph |
| 12 | H | CH$_2$OCH$_3$ | Ph | Ph |
| 13 | H | CH$_2$OCH$_3$ | 4-NO$_2$-Ph | Ph |
| 14 | H | CH$_2$OCH$_3$ | 3-OMe-Ph | Ph |
| 15 | H | CH$_2$OCH$_3$ | 3,5-(OMe)$_2$-Ph | Ph |
| 16 | H | CH$_2$OCH$_3$ | 3-Br-Ph | Ph |
| 17 | H | CH$_2$OCH$_3$ | 3-BnO-Ph | Ph |
| 18 | H | CH$_3$ | 3-OMe-Ph | pyridin-3-yl |
| 19 | H | CH$_3$ | 3,5-(OMe)$_2$-Ph | pyridin-3-yl |
| 20 | H | CH$_3$ | 3-Br-Ph | pyridin-3-yl |
| 21 | H | CH$_3$ | 4-NO$_2$-Ph | pyridin-3-yl |
| 22 | H | CH$_3$ | 3-CO$_2$CH$_3$-Ph | pyridin-3-yl |
| 23 | H | H | 4-Cl-Ph | —CH$_2$-(2,6-di-Cl)-Ph |
| 24 | H | H | 4-F-Ph | —CH$_2$-(2,6-di-Cl)-Ph |
| 25 | H | H | 3-OMe-Ph | —CH$_2$-(2,6-di-Cl)-Ph |
| 26 | H | H | 3,5-(OMe)$_2$-Ph | —CH$_2$-(2,6-di-Cl)-Ph |
| 27 | H | H | 3-Br-Ph | —CH$_2$-(2,6-di-Cl)-Ph |
| 28 | H | H | Ph | —CH$_2$-(2,6-di-Cl)-Ph |
| 29 | H | H | 3-BnO-Ph | —CH$_2$-(2,6-di-Cl)-Ph |
| 30 | H | H | 4-NO$_2$-Ph | —CH$_2$-(2,6-di-Cl)-Ph |
| 31 | H | H | 3-CO$_2$CH$_3$-Ph | —CH$_2$-(2,6-di-Cl)-Ph |
| 32 | H | H | 6-Cl-pyridin-3-yl | —CH$_2$-(2,6-di-Cl)-Ph |
| 33 | H | H | cyclohexyl | —CH$_2$-(2,6-di-Cl)-Ph |
| 34 | H | CH$_2$OCH$_3$ | 3-Cl-Ph | Ph |
| 35 | H | CH$_3$ | 3-Cl-Ph | pyridin-3-yl |
| 36 | H | H | H | 4-CO$_2$H-phenyl |
| 37 | H | H | H | 4-Cl-phenyl |
| 38 | H | H | H | 4-CF$_3$-phenyl |
| 39 | H | H | H | 4-CH$_3$-phenyl |
| 40 | H | H | H | 2-Cl-phenyl |
| 41 | H | H | H | 4-OCH$_3$-phenyl |
| 42 | H | H | Ph | 4-Cl-phenyl |
| 43 | H | H | Ph | 4-CF$_3$-phenyl |

TABLE 1-continued

Compounds of Formula IIa

IIa

| No. IIa- | G | —T$_{(n)}$—R | R$^1$ | R$^2$ |
|---|---|---|---|---|
| 44 | H | H | Ph | 4-CH$_3$-phenyl |
| 45 | H | H | CH$_2$Ph | pyridin-3-yl |
| 46 | H | H | COPh | 4-Cl-phenyl |
| 47 | H | H | COPh | 4-CF$_3$-phenyl |
| 48 | H | H | COPh | 4-CH$_3$-phenyl |
| 49 | H | H | CONHCH$_2$Ph | 4-Cl-phenyl |
| 50 | H | H | CONHCH$_2$Ph | 4-CF$_3$-phenyl |
| 51 | H | H | CONHCH$_2$Ph | 4-CH$_3$-phenyl |
| 52 | H | H | SO$_2$Me | CH$_2$Ph |
| 53 | H | H | Ph | thiazol-2-yl |
| 54 | H | H | cyclohexyl | piperidin-1-yl |
| 55 | H | H | cyclohexyl | 4-CONHMe-phenyl |
| 56 | H | H | Ph | Ph |
| 57 | H | H | CH$_2$Ph | CH$_2$Ph |
| 58 | H | H | H | CH$_2$Ph |
| 59 | H | H | H | Ph |
| 60 | H | H | 3-OBn-Ph | Ph |
| 61 | H | H | 3-SO$_2$NH$_2$-Ph | Ph |
| 62 | H | H | 3-OH-Ph | Ph |
| 63 | H | H | 4-OBn-Ph | Ph |
| 64 | H | H | 3-NO$_2$-Ph | 3-OMe-Ph |
| 65 | H | H | 3-NH$_2$-Ph | 3-OMe-Ph |
| 66 | H | H | 3-NO$_2$-Ph | 3-OH-Ph |
| 67 | H | H | Ph | 3-OBn-Ph |
| 68 | H | H | 3-NO$_2$-Ph | 3-OBn-Ph |
| 69 | H | H | 3-NO$_2$-Ph | 3-OBn-Ph |
| 70 | H | H | 3-OBn-Ph | 3-pyridyl |
| 71 | H | H | 3-OH-Ph | 3-pyridyl |
| 72 | H | H | 3-NH$_2$-Ph | 3-Br-Ph |
| 73 | H | H | 3-NH$_2$-Ph | 3-OPh-Ph |
| 74 | H | H | 3-OBn-Ph | 5-Br-3-pyridyl |
| 75 | H | H | Ph | 3-OPh-Ph |
| 76 | H | H | 3-OH-Ph | 3-OBn-Ph |
| 77 | H | H | 3-OH-Ph | 3-OPh-Ph |
| 78 | H | H | 3-OH-Ph | 3-OH-Ph |
| 79 | H | H | 3-OH-Ph | 3-Br-Ph |
| 80 | H | H | 3-OBn-Ph | 3-Br-Ph |
| 81 | H | H | 3-OH-Ph | 3-(3-OH-Ph)-Ph |
| 82 | H | H | 3-OH-Ph | 3-(3-OEt-Ph)-Ph |
| 83 | H | H | 3-OH-Ph | 3-(3-pyridyl)-Ph |
| 84 | H | H | 3-OBn-Ph | 5-Ph-pyridin-3-yl |
| 85 | H | H | 3-OBn-Ph | 5-Br-3-pyridyl |
| 86 | H | H | 3-OBn-Ph | 5-Ph-3-pyridyl |
| 87 | H | H | 4-OH-Ph | Ph |
| 88 | H | H | 3-OH-Ph | 5-Ph-pyridin-3-yl |
| 89 | H | H | 3-OH-Ph | 3-(3-NH$_2$-Ph)-Ph |
| 90 | H | H | 3-OH-Ph | 3-(3-Cl,4-F-Ph)-Ph |
| 91 | H | H | 3-OH-Ph | 3-(4-iPr-Ph)-Ph |
| 92 | H | H | 3-NO$_2$-Ph | 5-Ph-pyridin-3-yl |
| 93 | H | H | 3-OH-Ph | 3-(3-N-Boc-pyrrol-2-yl)-Ph |
| 94 | H | H | 3-NHSO$_2$Me-Ph | 3-pyridyl |
| 95 | H | H | 3-NHSO$_2$Et-Ph | 3-pyridyl |
| 96 | H | H | 3-SO$_2$NH$_2$-Ph | 3-pyridyl |
| 97 | H | H | 3-OH-Ph | 3-(2-OH-Ph)-Ph |
| 98 | H | H | 3-OH-Ph | 3-(3-pyrrol-2-yl)-Ph |
| 99 | H | H | 3-OH-Ph | 3-(6-OMe-pyridin-2-yl)-Ph |
| 100 | H | H | 3-OH-Ph | 3-(5-OMe-pyridin-2-yl)-Ph |
| 101 | H | H | 3-OH-Ph | 3-(2,5-Me$_2$-isoxazol-4-yl)-Ph |
| 102 | H | H | 3-OH-Ph | 3-(pyridin-4-yl)-Ph |
| 103 | H | CH$_3$ | H | 4-CO$_2$H-phenyl |

TABLE 1-continued

Compounds of Formula IIa

IIa

| No. IIa- | G | —T$_{(n)}$—R | R$^1$ | R$^2$ |
|---|---|---|---|---|
| 104 | H | CH$_3$ | H | 4-Cl-phenyl |
| 105 | H | CH$_3$ | H | 4-CF$_3$-phenyl |
| 106 | H | CH$_3$ | H | 4-CH$_3$-phenyl |
| 107 | H | CH$_3$ | H | 2-Cl-phenyl |
| 108 | H | CH$_3$ | H | 4-OCH$_3$-phenyl |
| 109 | H | CH$_3$ | Ph | 4-Cl-phenyl |
| 110 | H | CH$_3$ | Ph | 4-CF$_3$-phenyl |
| 111 | H | CH$_3$ | Ph | 4-CH$_3$-phenyl |
| 112 | H | CH$_3$ | CH$_2$Ph | pyridin-3-yl |
| 113 | H | CH$_3$ | COPh | 4-Cl-phenyl |
| 114 | H | CH$_3$ | COPh | 4-CF$_3$-phenyl |
| 115 | H | CH$_3$ | COPh | 4-CH$_3$-phenyl |
| 116 | H | CH$_3$ | CONHCH$_2$Ph | 4-Cl-phenyl |
| 117 | H | CH$_3$ | CONHCH$_2$Ph | 4-CF$_3$-phenyl |
| 118 | H | CH$_3$ | CONHCH$_2$Ph | 4-CH$_3$-phenyl |
| 119 | H | CH$_3$ | SO$_2$Me | CH$_2$Ph |
| 120 | H | CH$_3$ | Ph | thiazol-2-yl |
| 121 | H | CH$_3$ | cyclohexyl | piperidin-1-yl |
| 122 | H | CH$_3$ | cyclohexyl | 4-CONHMe-phenyl |
| 123 | H | CH$_3$ | Ph | Ph |
| 124 | H | CH$_3$ | CH$_2$Ph | CH$_2$Ph |
| 125 | H | CH$_3$ | H | CH$_2$Ph |
| 126 | H | CH$_3$ | H | Ph |
| 127 | H | CH$_3$ | 3-OBn-Ph | Ph |
| 128 | H | CH$_3$ | 3-SO$_2$NH$_2$-Ph | Ph |
| 129 | H | CH$_3$ | 3-OH-Ph | Ph |
| 130 | H | CH$_3$ | 4-OBn-Ph | Ph |
| 131 | H | CH$_3$ | 3-NO$_2$-Ph | 3-OMe-Ph |
| 132 | H | CH$_3$ | 3-NH$_2$-Ph | 3-OMe-Ph |
| 133 | H | CH$_3$ | 3-NO$_2$-Ph | 3-OH-Ph |
| 134 | H | CH$_3$ | Ph | 3-OBn-Ph |
| 135 | H | CH$_3$ | 3-NO$_2$-Ph | 3-OBn-Ph |
| 136 | H | CH$_3$ | 3-NO$_2$-Ph | 3-OBn-Ph |
| 137 | H | CH$_3$ | 3-OH-Ph | 3-pyridyl |
| 138 | H | CH$_3$ | 3-NH$_2$-Ph | 3-Br-Ph |
| 139 | H | CH$_3$ | 3-NH$_2$-Ph | 3-OPh-Ph |
| 140 | H | CH$_3$ | 3-OBn-Ph | 5-Br-3-pyridyl |
| 141 | H | CH$_3$ | Ph | 3-OPh-Ph |
| 142 | H | CH$_3$ | 3-OH-Ph | 3-OBn-Ph |
| 143 | H | CH$_3$ | 3-OH-Ph | 3-OPh-Ph |
| 144 | H | CH$_3$ | 3-OH-Ph | 3-OH-Ph |
| 145 | H | CH$_3$ | 3-OH-Ph | 3-Br-Ph |
| 146 | H | CH$_3$ | 3-OBn-Ph | 3-Br-Ph |
| 147 | H | CH$_3$ | 3-OH-Ph | 3-(3-OH-Ph)-Ph |
| 148 | H | CH$_3$ | 3-OH-Ph | 3-(3-OEt-Ph)-Ph |
| 149 | H | CH$_3$ | 3-OH-Ph | 3-(3-pyridyl)-Ph |
| 150 | H | CH$_3$ | 3-OBn-Ph | 5-Ph-pyridin-3-yl |
| 151 | H | CH$_3$ | 3-OBn-Ph | 5-Br-3-pyridyl |
| 152 | H | CH$_3$ | 3-OBn-Ph | 5-Ph-3-pyridyl |
| 153 | H | CH$_3$ | 4-OH-Ph | Ph |
| 154 | H | CH$_3$ | 3-OH-Ph | 5-Ph-pyridin-3-yl |
| 155 | H | CH$_3$ | 3-OH-Ph | 3-(3-NH$_2$-Ph)-Ph |
| 156 | H | CH$_3$ | 3-OH-Ph | 3-(3-Cl,4-F-Ph)-Ph |
| 157 | H | CH$_3$ | 3-OH-Ph | 3-(4-iPr-Ph)-Ph |
| 158 | H | CH$_3$ | 3-NO$_2$-Ph | 5-Ph-pyridin-3-yl |
| 159 | H | CH$_3$ | 3-OH-Ph | 3-(3-N-Boc-pyrrol-2-yl)-Ph |
| 160 | H | CH$_3$ | 3-NHSO$_2$Me-Ph | 3-pyridyl |
| 161 | H | CH$_3$ | 3-NHSO$_2$Et-Ph | 3-pyridyl |
| 162 | H | CH$_3$ | 3-OMe-Ph | Ph |
| 163 | H | CH$_3$ | 3-SO$_2$NH$_2$-Ph | 3-pyridyl |

TABLE 1-continued

Compounds of Formula IIa

| No. IIa- | G | —T$_{(n)}$—R | R$^1$ | R$^2$ |
|---|---|---|---|---|
| 164 | H | CH$_3$ | 3-OH-Ph | 3-(2-OH-Ph)-Ph |
| 165 | H | CH$_3$ | 3-OH-Ph | 3-(3-pyrrol-2-yl)-Ph |
| 166 | H | CH$_3$ | 3-OH-Ph | 3-(6-OMe-pyridin-2-yl)-Ph |
| 167 | H | CH$_3$ | 3-OH-Ph | 3-(5-OMe-pyridin-2-yl)-Ph |
| 168 | H | CH$_3$ | 3-OH-Ph | 3-(2,5-Me$_2$-isoxazol-4-yl)-Ph |
| 169 | H | CH$_3$ | 3-OH-Ph | 3-(pyridin-4-yl)-Ph |
| 170 | H | CH$_2$OCH$_3$ | H | 4-CO$_2$H-phenyl |
| 171 | H | CH$_2$OCH$_3$ | H | 4-Cl-phenyl |
| 172 | H | CH$_2$OCH$_3$ | H | 4-CF$_3$-phenyl |
| 173 | H | CH$_2$OCH$_3$ | H | 4-CH$_3$-phenyl |
| 174 | H | CH$_2$OCH$_3$ | H | 2-Cl-phenyl |
| 175 | H | CH$_2$OCH$_3$ | H | 4-OCH$_3$-phenyl |
| 176 | H | CH$_2$OCH$_3$ | Ph | 4-Cl-phenyl |
| 177 | H | CH$_2$OCH$_3$ | Ph | 4-CF$_3$-phenyl |
| 178 | H | CH$_2$OCH$_3$ | Ph | 4-CH$_3$-phenyl |
| 179 | H | CH$_2$OCH$_3$ | CH$_2$Ph | pyridin-3-yl |
| 180 | H | CH$_2$OCH$_3$ | COPh | 4-Cl-phenyl |
| 181 | H | CH$_2$OCH$_3$ | COPh | 4-CF$_3$-phenyl |
| 182 | H | CH$_2$OCH$_3$ | COPh | 4-CH$_3$-phenyl |
| 183 | H | CH$_2$OCH$_3$ | CONHCH$_2$Ph | 4-Cl-phenyl |
| 184 | H | CH$_2$OCH$_3$ | CONHCH$_2$Ph | 4-CF$_3$-phenyl |
| 185 | H | CH$_2$OCH$_3$ | CONHCH$_2$Ph | 4-CH$_3$-phenyl |
| 186 | H | CH$_2$OCH$_3$ | SO$_2$Me | CH$_2$Ph |
| 187 | H | CH$_2$OCH$_3$ | Ph | thiazol-2-yl |
| 188 | H | CH$_2$OCH$_3$ | cyclohexyl | piperidin-1-yl |
| 189 | H | CH$_2$OCH$_3$ | cyclohexyl | 4-CONHMe-phenyl |
| 190 | H | CH$_2$OCH$_3$ | CH$_2$Ph | CH$_2$Ph |
| 191 | H | CH$_2$OCH$_3$ | H | CH$_2$Ph |
| 192 | H | CH$_2$OCH$_3$ | H | Ph |
| 193 | H | CH$_2$OCH$_3$ | 3-SO$_2$NH$_2$-Ph | Ph |
| 194 | H | CH$_2$OCH$_3$ | 3-OH-Ph | Ph |
| 195 | H | CH$_2$OCH$_3$ | 4-OBn-Ph | Ph |
| 196 | H | CH$_2$OCH$_3$ | 3-NO$_2$-Ph | 3-OMe-Ph |
| 197 | H | CH$_2$OCH$_3$ | 3-NH$_2$-Ph | 3-OMe-Ph |
| 198 | H | CH$_2$OCH$_3$ | 3-NO$_2$-Ph | 3-OH-Ph |
| 199 | H | CH$_2$OCH$_3$ | Ph | 3-OBn-Ph |
| 200 | H | CH$_2$OCH$_3$ | 3-NO$_2$-Ph | 3-OBn-Ph |
| 201 | H | CH$_2$OCH$_3$ | 3-NO$_2$-Ph | 3-OBn-Ph |
| 202 | H | CH$_2$OCH$_3$ | 3-OBn-Ph | 3-pyridyl |
| 203 | H | CH$_2$OCH$_3$ | 3-OH-Ph | 3-pyridyl |
| 204 | H | CH$_2$OCH$_3$ | 3-NH$_2$-Ph | 3-Br-Ph |
| 205 | H | CH$_2$OCH$_3$ | 3-NH$_2$-Ph | 3-OPh-Ph |
| 206 | H | CH$_2$OCH$_3$ | 3-OBn-Ph | 5-Br-3-pyridyl |
| 207 | H | CH$_2$OCH$_3$ | Ph | 3-OPh-Ph |
| 208 | H | CH$_2$OCH$_3$ | 3-OH-Ph | 3-OBn-Ph |
| 209 | H | CH$_2$OCH$_3$ | 3-OH-Ph | 3-OPh-Ph |
| 210 | H | CH$_2$OCH$_3$ | 3-OH-Ph | 3-OH-Ph |
| 211 | H | CH$_2$OCH$_3$ | 3-OH-Ph | 3-Br-Ph |
| 212 | H | CH$_2$OCH$_3$ | 3-OBn-Ph | 3-Br-Ph |
| 213 | H | CH$_2$OCH$_3$ | 3-OH-Ph | 3-(3-OH-Ph)-Ph |
| 214 | H | CH$_2$OCH$_3$ | 3-OH-Ph | 3-(3-OEt-Ph)-Ph |
| 215 | H | CH$_2$OCH$_3$ | 3-OH-Ph | 3-(3-pyridyl)-Ph |
| 216 | H | CH$_2$OCH$_3$ | 3-OBn-Ph | 5-Ph-pyridin-3-yl |
| 217 | H | CH$_2$OCH$_3$ | 3-OBn-Ph | 5-Br-3-pyridyl |
| 218 | H | CH$_2$OCH$_3$ | 3-OBn-Ph | 5-Ph-3-pyridyl |
| 219 | H | CH$_2$OCH$_3$ | 4-OH-Ph | Ph |
| 220 | H | CH$_2$OCH$_3$ | 3-OH-Ph | 5-Ph-pyridin-3-yl |
| 221 | H | CH$_2$OCH$_3$ | 3-OH-Ph | 3-(3-NH$_2$-Ph)-Ph |
| 222 | H | CH$_2$OCH$_3$ | 3-OH-Ph | 3-(3-Cl,4-F-Ph)-Ph |
| 223 | H | CH$_2$OCH$_3$ | 3-OH-Ph | 3-(4-iPr-Ph)-Ph |

TABLE 1-continued

Compounds of Formula IIa

IIa

| No. IIa- | G | —T(n)—R | R¹ | R² |
|---|---|---|---|---|
| 224 | H | CH₂OCH₃ | 3-NO₂-Ph | 5-Ph-pyridin-3-yl |
| 225 | H | CH₂OCH₃ | 3-OH-Ph | 3-(3-N-Boc-pyrrol-2-yl)-Ph |
| 226 | H | CH₂OCH₃ | 3-NHSO₂Me-Ph | 3-pyridyl |
| 227 | H | CH₂OCH₃ | 3-NHSO₂Et-Ph | 3-pyridyl |
| 228 | H | CH₂OCH₃ | 3-SO₂NH₂-Ph | 3-pyridyl |
| 229 | H | CH₂OCH₃ | 3-OH-Ph | 3-(2-OH-Ph)-Ph |
| 230 | H | CH₂OCH₃ | 3-OH-Ph | 3-(3-pyrrol-2-yl)-Ph |
| 231 | H | CH₂OCH₃ | 3-OH-Ph | 3-(6-OMe-pyridin-2-yl)-Ph |
| 232 | H | CH₂OCH₃ | 3-OH-Ph | 3-(5-OMe-pyridin-2-yl)-Ph |
| 233 | H | CH₂OCH₃ | 3-OH-Ph | 3-(2,5-Me₂-isoxazol-4-yl)-Ph |
| 234 | H | CH₂OCH₃ | 3-OH-Ph | 3-(pyridin-4-yl)-Ph |

Another embodiment related to compounds of formula IIb:

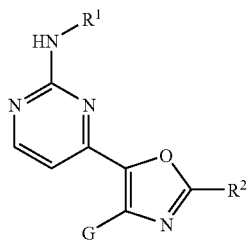

or a pharmaceutically acceptable derivative thereof, wherein $R^1$, $R^2$, and G are as described above.

Preferred $R^1$ groups of formula IIb are selected from hydrogen, $Ar^1$ or -T-$Ar^1$ wherein T is a $C_{1-4}$ alkylidene chain and $Ar^1$ is an optionally substituted 6-membered saturated, partially saturated, or aryl ring having zero to two heteroatoms independently selected from nitrogen, oxygen, or sulfur. More preferred $R^1$ groups of formula IIa are selected from phenyl, benzyl, pyridyl, piperidinyl, or cyclohexyl. Preferred substituents on $R^1$ are selected from —CO₂R, —OR, -Z-$R^3$, halogen, —NRSO₂R, —SO₂N(R)₂, —NRCON(R)₂, —NO₂, or —N(R)₂. More preferred substituents of $R^1$ are selected from benzyloxy, phenoxy, —SO₂NH₂, —OH, —NO₂, —NH₂, —OMe, —Br, —Cl, —CO₂Me, —NHSO₂Me, —NHSO₂Et, —NHCON(Me)₂, —NHCON(Et)₂, —NHCOpyrrolidin-1-yl, or —NHCOmorpholin-4-yl.

Preferred $R^2$ groups of formula IIb are selected from $Ar^2$ or —CH₂—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, wherein $Ar^2$ is optionally substituted with one to five groups independently selected from -Z-$R^3$, —R, halogen, —NO₂, —CN, —OR, —SR, —N(R)₂, —NRC(O)R, —NRC(O)N(R)₂, —NRCO₂R, —C(O)R, —CO₂R, —C(O)N(R)₂, —OC(O)N(R)₂, —S(O)R, —SO₂R, —SO₂N(R)₂, —N(R)SO₂R, —N(R)SO₂N(R)₂, —C(O)C(O)R, or —C(O)CH₂C(O)R. More preferred $R^2$ groups of formula IIb are selected from phenyl, pyridyl, pyrimidinyl, cyclohexyl, piperidinyl, furanyl, or benzyl. Preferred Z is a $C_{1-4}$ alkylidene chain and wherein one methylene unit of Z is optionally replaced by —S—, —O—, —N(R)—, or —C(O)O—. Preferred substituents on $Ar^2$ are selected from -Z-$Ar^3$, —R, halogen, —OR, —N(R)₂, or —CO₂R, wherein $Ar^3$ is an optionally substituted 5-6 membered aryl ring having zero to two heteroatoms independently selected from nitrogen, oxygen, or sulfur. More preferred substituents on $Ar^2$ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen such as chloro, bromo, and fluoro, haloalkyl such as trifluoromethyl, —OH, —NH₂, alkyl such as methyl, or alkoxy such as methoxy and ethoxy.

Preferred G is hydrogen, $C_{1-3}$ aliphatic, or $C_1$-$C_3$ aliphatic wherein one methylene unit of G is replaced by —C(O)—. More preferred G is hydrogen.

Preferred compounds of formula IIb are those having one or more, more preferably more than one, and most preferably all, of the features selected from the group consisting of:

(a) $R^1$ is hydrogen, $Ar^1$ or -T-$Ar^1$ wherein T is a $C_{1-4}$ alkylidene chain and $Ar^1$ is a 6-membered saturated, partially saturated, or aryl ring having zero to two heteroatoms independently selected from nitrogen, oxygen, or sulfur, and wherein each member of $R^1$ is optionally substituted with one -Z-$R^3$ and one to three additional groups independently selected from —$CO_2R$, —OR, halogen, —$NRSO_2R$, —$SO_2N(R)_2$, —$NRCON(R)_2$, —$NO_2$, or —$N(R)_2$;

(b) $R^2$ is $Ar^2$ or —$CH_2$—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted with one to five groups independently selected from -Z-$R^3$, —R, halogen, —$NO_2$, —CN, —OR, —SR, —$N(R)_2$, —NRC(O)R, —NRC(O)N(R)_2, —$NRCO_2R$, —C(O)R, —$CO_2R$, —C(O)N(R)_2, —OC(O)N(R)_2, —S(O)R, —$SO_2R$, —$SO_2N(R)_2$, —N(R)$SO_2R$, —N(R)$SO_2N(R)_2$, —C(O)C(O)R, or —C(O)$CH_2$C(O)R; and (c) G is hydrogen.

More preferred compounds of formula IIb are those having one or more, more preferably more than one, and most preferably all, of the features selected from the group consisting of:

(a) $R^1$ is selected from a phenyl, benzyl, pyridyl, piperidinyl, or cyclohexyl ring, wherein said ring is optionally substituted with benzyloxy, phenoxy, —$SO_2NH_2$, —OH, —$NO_2$, —$NH_2$, —OMe, —Br, —Cl, —$CO_2Me$, —$NHSO_2Me$, —$NHSO_2Et$, —NHCON(Me)_2, —NHCON(Et)_2, —NHCOpyrrolidin-1-yl, —NHCOmorpholin-4-yl, —O—$CH_2$-phenyl, —O(CH_2)_3OH, —O(CH_2)_3NH(CH_2)_2OH, —O(CH_2)_2NH(CH_2)_2OH, —O(CH_2)_3N (hydroxyethyl) (methyl), —O(CH_2)_3pyrrolidin-1-yl, —O(CH_2)_2morpholin-4-yl, —O(CH_2)_3N(Me)_2, —O(CH_2)_3N(Et)_2, —O(CH_2)_3(4-hydroxyethyl piperazin-1-yl), —O(CH_2)_3piperazin-1-yl, —O(CH_2)_3(4-hydroxymethylpiperidin-1-yl), —O(CH_2)_3(4-hydroxypiperidin-1-yl), —NHCO(CH_2)_3 N(Me)_2, —NHCO(CH_2)_3NCOCH_3, —NHCOCH_2pyridin2-yl, —NHCOCH_2(2-aminothiazol-4-yl), —NHCOCH_2cyclopropyl, —NHCO(CH_2)_2N(Et)_2, —NHCO(CH_2)_2-(piperazin-2,5-dione-3-yl), —NHCO_2CH_2tetrahydrofuran-2-yl, —NHCO_2tetrahydrofuran-2-yl, —NHCO_2tetrahydropyran-4-yl, or —NHCO_2CH_2tetrahydropyran-2-yl;

(b) $R^2$ is selected from phenyl, pyridyl, pyrimidinyl, cyclohexyl, piperidinyl, furanyl, or benzyl, wherein $R^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —$NH_2$, methyl, methoxy, or ethoxy; and (c) G is hydrogen.

Exemplary compounds of formula IIb are shown below in Table 2.

TABLE 2

Compounds of Formula IIb

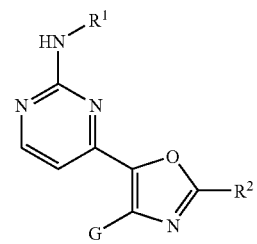

IIb

| No. IIb- | G | $R^1$ | $R^2$ |
|---|---|---|---|
| 1 | H | 4-Cl-phenyl | Ph |
| 2 | H | 4-F-phenyl | Ph |
| 3 | H | 3-OMe-Ph | Ph |
| 4 | H | 3,5-(OMe)_2-Ph | Ph |
| 5 | H | Ph | Ph |
| 6 | H | 3-BnO-Ph | Ph |
| 7 | H | 4-NO_2-Ph | Ph |
| 8 | H | 3-Br-Ph | Ph |
| 9 | H | 3-CO_2CH_3-Ph | Ph |
| 10 | H | cyclohexyl | Ph |
| 11 | H | 4-Cl-phenyl | 2-OBn-Ph |
| 12 | H | 3-NO_2-Ph | 2-OBn-Ph |
| 13 | H | CH_2-phenyl | 2-OBn-Ph |
| 14 | H | cyclohexyl | 2-OBn-Ph |
| 15 | H | 3-OMe-Ph | 2-OBn-Ph |
| 16 | H | 3,5-(OMe)_2-Ph | 2-OBn-Ph |
| 17 | H | 4-Cl-phenyl | cyclohexyl |
| 18 | H | 3-Cl-phenyl | Ph |
| 19 | H | H | 4-CO_2H-phenyl |
| 20 | H | H | 4-Cl-phenyl |
| 21 | H | H | 4-CF_3-phenyl |
| 22 | H | H | 4-CH_3-phenyl |
| 23 | H | H | 2-Cl-phenyl |
| 24 | H | H | 4-OCH_3-phenyl |
| 25 | H | Ph | 4-Cl-phenyl |
| 26 | H | Ph | 4-CF_3-phenyl |
| 27 | H | Ph | 4-CH_3-phenyl |
| 28 | H | CH_2Ph | pyridin-3-yl |
| 29 | H | COPh | 4-Cl-phenyl |
| 30 | H | COPh | 4-CF_3-phenyl |
| 31 | H | COPh | 4-CH_3-phenyl |
| 32 | H | CONHCH_2Ph | 4-Cl-phenyl |
| 33 | H | CONHCH_2Ph | 4-CF_3-phenyl |
| 34 | H | CONHCH_2Ph | 4-CH_3-phenyl |
| 35 | H | SO_2Me | CH_2Ph |
| 36 | H | Ph | thiazol-2-yl |
| 37 | H | cyclohexyl | piperidin-1-yl |
| 38 | H | cyclohexyl | 4-CONHMe-phenyl |
| 39 | H | CH_2Ph | CH_2Ph |
| 40 | H | H | CH_2Ph |
| 41 | H | H | Ph |
| 42 | H | 3-SO_2NH_2-Ph | Ph |
| 43 | H | 3-OH-Ph | Ph |
| 44 | H | 4-OBn-Ph | Ph |
| 45 | H | 3,5-(OMe)_2-Ph | cyclohexyl |
| 46 | H | 3-SO_2NH_2-Ph | cyclohexyl |
| 47 | H | 3-OBn-Ph | cyclohexyl |
| 48 | H | Ph | cyclohexyl |
| 49 | H | 4-CO_2Et-Ph | cyclohexyl |
| 50 | H | 3-OH-Ph | cyclohexyl |
| 51 | H | 3-NO_2-Ph | 3-OMe-Ph |
| 52 | H | 3-NH_2-Ph | 3-OMe-Ph |
| 53 | H | 3-NO_2-Ph | 3-OH-Ph |
| 54 | H | Ph | 3-OBn-Ph |
| 55 | H | 3-NO_2-Ph | 3-OBn-Ph |
| 56 | H | 3-NO_2-Ph | 3-OBn-Ph |
| 57 | H | 3-OBn-Ph | 3-pyridyl |
| 58 | H | 3-OH-Ph | 3-pyridyl |

TABLE 2-continued

Compounds of Formula IIb

IIb

| No. IIb- | G | R¹ | R² |
|---|---|---|---|
| 59 | H | 3-NH₂-Ph | 3-Br-Ph |
| 60 | H | 3-NH₂-Ph | 3-OPh-Ph |
| 61 | H | 3-OBn-Ph | 5-Br-3-pyridyl |
| 62 | H | Ph | 3-OPh-Ph |
| 63 | H | 3-OH-Ph | 3-OBn-Ph |
| 64 | H | 3-OH-Ph | 3-OPh-Ph |
| 65 | H | 3-OH-Ph | 3-OH-Ph |
| 66 | H | 3-OH-Ph | 3-Br-Ph |
| 67 | H | 3-OBn-Ph | 3-Br-Ph |
| 68 | H | 3-OH-Ph | 3-(3-OH-Ph)-Ph |
| 69 | H | 3-OH-Ph | 3-(3-OEt-Ph)-Ph |
| 70 | H | 3-OH-Ph | 3-(3-pyridyl)-Ph |
| 71 | H | 3-OBn-Ph | 5-Ph-pyridin-3-yl |
| 72 | H | 3-OBn-Ph | 5-Br-3-pyridyl |
| 73 | H | 3-OBn-Ph | 5-Ph-3-pyridyl |
| 74 | H | 4-OH-Ph | Ph |
| 75 | H | 3-OH-Ph | 5-Ph-pyridin-3-yl |
| 76 | H | 3-OH-Ph | 3-(3-NH₂-Ph)-Ph |
| 77 | H | 3-OH-Ph | 3-(3-Cl,4-F-Ph)-Ph |
| 78 | H | 3-OH-Ph | 3-(4-iPr-Ph)-Ph |
| 79 | H | 3-NO₂-Ph | 5-Ph-pyridin-3-yl |
| 80 | H | 3-OH-Ph | 3-(3-N-Boc-pyrrol-2-yl)-Ph |
| 81 | H | 3-NHSO₂Me-Ph | 3-pyridyl |
| 82 | H | 3-NHSO₂Et-Ph | 3-pyridyl |
| 83 | H | 3-SO₂NH₂-Ph | 3-pyridyl |
| 84 | H | 3-OH-Ph | 3-(2-OH-Ph)-Ph |
| 85 | H | 3-OH-Ph | 3-(3-pyrrol-2-yl)-Ph |
| 86 | H | 3-OH-Ph | 3-(6-OMe-pyridin-2-yl)-Ph |
| 87 | H | 3-OH-Ph | 3-(5-OMe-pyridin-2-yl)-Ph |
| 88 | H | 3-OH-Ph | 3-(2,5-Me₂-isoxazol-4-yl)-Ph |
| 89 | H | 3-OH-Ph | 3-(pyridin-4-yl)-Ph |

Another embodiment related to compounds of formula IIc:

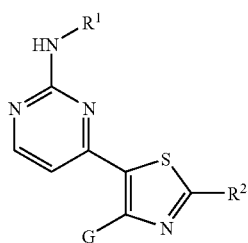

IIc or a pharmaceutically acceptable derivative thereof, wherein $R^1$, $R^2$, and G are as described above.

Preferred $R^1$ groups of formula IIc are selected from hydrogen, $Ar^1$ or -T-$Ar^1$ wherein T is a $C_{1-4}$ alkylidene chain and $Ar^1$ is an optionally substituted 6-membered saturated, partially saturated, or aryl ring having zero to two heteroatoms independently selected from nitrogen, oxygen, or sulfur. More preferred $R^1$ groups of formula IIc are selected from phenyl, benzyl, pyridyl, piperidinyl, or cyclohexyl. Preferred substituents on $R^1$ are selected from —CO₂R, —OR, -Z-R³, halogen, —NRSO₂R, —SO₂N(R)₂, —NRCON(R)₂, —NO₂, or —N(R)₂. More preferred substituents of $R^1$ are selected from benzyloxy, phenoxy, —SO₂NH₂, —OH, —NO₂, —NH₂, —OMe, —Br, —Cl, —CO₂Me, —NHSO₂Me, —NHSO₂Et, —NHCON(Me)₂, —NHCON(Et)₂, —NHCOpyrrolidin-1-yl, or —NHCOmorpholin-4-yl.

Preferred $R^2$ groups of formula IIc are selected from $Ar^2$ or —CH₂—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, wherein $Ar^2$ is optionally substituted with one to five groups independently selected from -Z-R³, —R, halogen, —NO₂, —CN, —OR, —SR, —N(R)₂, —NRC(O)R, —NRC(O)N(R)₂, —NRCO₂R, —C(O)R, —CO₂R, —C(O)N(R)₂, —OC(O)N (R)₂, —S(O)R, —SO₂R, —SO₂N(R)₂, —N(R)SO₂R, —N(R)SO₂N(R)₂, —C(O)C(O)R, or —C(O)CH₂C(O)R. More preferred $R^2$ groups of formula IIc are selected from phenyl, pyridyl, pyrimidinyl, cyclohexyl, piperidinyl, furanyl, or benzyl. Preferred Z is a $C_{1-4}$ alkylidene chain and wherein one methylene unit of Z is optionally replaced by —S—, —O—, —N(R)—, or —C(O)O—. Preferred substituents on $Ar^2$ are selected from -Z-$Ar^3$, —R, halogen, —OR, —N(R)₂, or —CO₂R, wherein $Ar^3$ is an optionally substituted 5-6 membered aryl ring having zero to two heteroatoms independently selected from nitrogen, oxygen, or sulfur. More preferred substituents on $Ar^2$ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen such as chloro, bromo, and fluoro, haloalkyl such as trifluoromethyl, —OH, —NH₂, alkyl such as methyl, or alkoxy such as methoxy and ethoxy.

Preferred G is hydrogen, $C_{1-3}$ aliphatic, or $C_1$-$C_3$ aliphatic wherein one methylene unit of G is replaced by —C(O)—. More preferred G is hydrogen.

Preferred compounds of formula IIc are those having one or more, more preferably more than one, and most preferably all, of the features selected from the group consisting of:

(a) $R^1$ is hydrogen, $Ar^1$ or -T-$Ar^1$ wherein T is a $C_{1-4}$ alkylidene chain and $Ar^1$ is a 6-membered saturated, partially saturated, or aryl ring having zero to two heteroatoms independently selected from nitrogen, oxygen, or sulfur, and wherein each member of $R^1$ is optionally substituted with one -Z-R³ and one to three additional groups independently selected from —CO₂R, —OR, halogen, —NRSO₂R, —SO₂N(R)₂, —NRCON(R)₂, —NO₂, or —N(R)₂;

(b) $R^2$ is $Ar^2$ or —CH₂—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted with one to five groups independently selected from -Z-R³, —R, halogen, —NO₂, —CN, —OR, —SR, —N(R)₂, —NRC(O)R, —NRC(O)N(R)₂, —NRCO₂R, —C(O)R, —CO₂R, —C(O)N(R)₂, —OC(O)N(R)₂, —S(O)R, —SO₂R, —SO₂N(R)₂, —N(R)SO₂R, —N(R)SO₂N(R)₂, —C(O)C(O)R, or —C(O)CH₂C(O)R; and (c) G is hydrogen.

More preferred compounds of formula IIc are those having one or more, more preferably more than one, and most preferably all, of the features selected from the group consisting of:

(a) $R^1$ is selected from a phenyl, benzyl, pyridyl, piperidinyl, or cyclohexyl ring, wherein said ring is optionally substituted with benzyloxy, phenoxy, —SO$_2$NH$_2$, —OH, —NO$_2$, —NH$_2$, —OMe, —Br, —Cl, —CO$_2$Me, —NHSO$_2$Me, —NHSO$_2$Et, —NHCON(Me)$_2$, —NHCON(Et)$_2$, —NHCOpyrrolidin-1-yl, —NHCOmorpholin-4-yl, —O—CH$_2$-phenyl, —O(CH$_2$)$_3$OH, —O(CH$_2$)$_3$NH(CH$_2$)$_2$OH, —O(CH$_2$)$_2$NH(CH$_2$)$_2$OH, —O(CH$_2$)$_3$N(hydroxyethyl) (methyl), —O(CH$_2$)$_3$pyrrolidin-1-yl, —O(CH$_2$)$_2$morpholin-4-yl, —O(CH$_2$)$_3$N(Me)$_2$, —O(CH$_2$)$_3$N(Et)$_2$, —O(CH$_2$)$_3$(4-hydroxyethyl piperazin-1-yl), —O(CH$_2$)$_3$piperazin-1-yl, —O(CH$_2$)$_3$(4-hydroxymethylpiperidin-1-yl), —O(CH$_2$)$_3$(4-hydroxypiperidin-1-yl), —NHCO(CH$_2$)$_3$N(Me)$_2$, —NHCO(CH$_2$)$_3$NCOCH$_3$, —NHCOCH$_2$pyridin-2-yl, —NHCOCH$_2$(2-aminothiazol-4-yl), —NHCOCH$_2$cyclopropyl, —NHCO(CH$_2$)$_2$N(Et)$_2$, —NHCO(CH$_2$)2-(piperazin-2,5-dione-3-yl), —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl;

(b) $R^2$ is selected from phenyl, pyridyl, pyrimidinyl, cyclohexyl, piperidinyl, furanyl, or benzyl, wherein $R^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —NH$_2$, methyl, methoxy, or ethoxy; and (c) G is hydrogen.

Exemplary compounds of formula IIc are shown below in Table 3.

TABLE 3

Compounds of Formula IIc

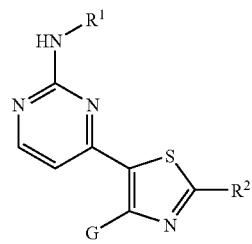

IIc

| No. IIc- | G | $R^1$ | $R^2$ |
|---|---|---|---|
| 1 | H | cyclohexyl | Ph |
| 2 | H | cyclohexyl | 2-OBn-Ph |
| 3 | H | H | 4-CO$_2$H-phenyl |
| 4 | H | H | 4-Cl-phenyl |
| 5 | H | H | 4-CF$_3$-phenyl |
| 6 | H | H | 4-CH$_3$-phenyl |
| 7 | H | H | 2-Cl-phenyl |
| 8 | H | H | 4-OCH$_3$-phenyl |
| 9 | H | CH$_2$Ph | pyridin-3-yl |
| 10 | H | COPh | 4-Cl-phenyl |
| 11 | H | COPh | 4-CF$_3$-phenyl |
| 12 | H | COPh | 4-CH$_3$-phenyl |
| 13 | H | CONHCH$_2$Ph | 4-Cl-phenyl |
| 14 | H | CONHCH$_2$Ph | 4-CF$_3$-phenyl |
| 15 | H | CONHCH$_2$Ph | 4-CH$_3$-phenyl |
| 16 | H | SO$_2$Me | CH$_2$Ph |
| 17 | H | cyclohexyl | piperidin-1-yl |
| 18 | H | cyclohexyl | 4-CONHMe-phenyl |
| 19 | H | CH$_2$Ph | CH$_2$Ph |
| 20 | H | H | CH$_2$Ph |
| 21 | H | H | Ph |
| 22 | CH$_3$ | 4-SO$_2$NH$_2$-Ph | thiophen-2-yl |
| 23 | CH$_3$ | 4-F-Ph | thiophen-2-yl |
| 24 | CH$_3$ | 4-Cl-Ph | thiophen-2-yl |
| 25 | CH$_3$ | 4-NO$_2$-Ph | thiophen-2-yl |
| 26 | CH$_3$ | H | 2-Cl-phenoxymethyl |
| 27 | CH$_3$ | Ph | Ph |
| 28 | CH$_3$ | 4-F-Ph | Ph |
| 29 | CH$_3$ | 4-Cl-Ph | Ph |
| 30 | CH$_3$ | 3-Cl-Ph | Ph |
| 31 | CH$_3$ | 4-NO$_2$-Ph | Ph |
| 32 | CH$_3$ | 3-OBn-Ph | Ph |
| 33 | CH$_3$ | Ph | 4-Cl-Ph |
| 34 | CH$_3$ | 4-F-Ph | 4-Cl-Ph |
| 35 | CH$_3$ | 4-Cl-Ph | 4-Cl-Ph |
| 36 | CH$_3$ | 3-Cl-Ph | 4-Cl-Ph |
| 37 | CH$_3$ | 3-BnO-Ph | 4-Cl-Ph |
| 38 | CO$_2$Et | 4-NO$_2$-Ph | Ph |
| 39 | CH$_3$ | Ph | 2-Cl-phenoxymethyl |
| 40 | CH$_3$ | 4-F-Ph | 2-Cl-phenoxymethyl |
| 41 | CH$_3$ | 4-Cl-Ph | 2-Cl-phenoxymethyl |

TABLE 3-continued

Compounds of Formula IIc

IIc

| No. IIc- | G | R¹ | R² |
|---|---|---|---|
| 42 | CH₃ | 3-Cl-Ph | (2-Cl-phenoxymethyl) |
| 43 | CH₃ | 3-BnO-Ph | (2-Cl-phenoxymethyl) |

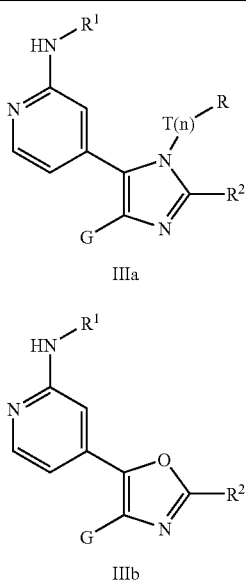

The above formulae IIa, IIb, and IIc compounds are those having a pyrimidine ring. Compounds of formula I having a pyridine ring are represented by the following general formulae IIIa, IIIb, and IIIc shown below in Table 4.

TABLE 4

Formulae IIIa, IIIb, and IIIc

IIIa

IIIb

TABLE 4-continued

Formulae IIIa, IIIb, and IIIc

IIIc

The compounds shown above in Table 4 are structurally similar to compounds of formula IIa, IIb, and IIc where the pyrimidine ring of formula IIa is replaced by a pyridine (IIIa, IIIb, and IIIc). Accordingly, preferred $R^1$, $R^2$, n, T, R, and G groups of the compounds shown above in Table 4 are as described above for the formula IIa, IIb or IIc compounds.

Exemplary structures of formulae IIIa, IIIb and IIIc are set forth in Table 5 below.

TABLE 5

Compounds of Formulae IIIa, IIIb, and IIIc

| No. | G | —T$_{(n)}$—R | R¹ | R² |
|---|---|---|---|---|
| IIIa-1 | H | H | 4-Cl-phenyl | Ph |
| IIIa-2 | H | H | 4-F-phenyl | Ph |
| IIIa-3 | H | H | 3-OMe-Ph | Ph |
| IIIa-4 | H | H | 3,5-(OMe)₂-Ph | Ph |
| IIIa-5 | H | CH₃ | 4-Cl-phenyl | pyridin-3-yl |
| IIIa-6 | H | CH₃ | 4-F-phenyl | pyridin-3-yl |
| IIIa-7 | H | CH₃ | Ph | pyridin-3-yl |
| IIIa-8 | H | CH₃ | 3-BnO-Ph | pyridin-3-yl |
| IIIa-9 | H | CH₃ | 6-Cl-pyridin-3-yl | pyridin-3-yl |
| IIIa-10 | H | CH₂OCH₃ | 4-Cl-phenyl | Ph |
| IIIa-11 | H | CH₂OCH₃ | 4-F-phenyl | Ph |
| IIIa-12 | H | CH₂OCH₃ | Ph | Ph |
| IIIa-13 | H | CH₂OCH₃ | 4-NO₂-Ph | Ph |
| IIIa-14 | H | CH₂OCH₃ | 3-OMe-Ph | Ph |
| IIIa-15 | H | CH₂OCH₃ | 3,5-(OMe)₂-Ph | Ph |
| IIIa-16 | H | CH₂OCH₃ | 3-Br-Ph | Ph |
| IIIa-17 | H | CH₂OCH₃ | 3-BnO-Ph | Ph |
| IIIa-18 | H | CH₃ | 3-OMe-Ph | pyridin-3-yl |
| IIIa-19 | H | CH₃ | 3,5-(OMe)₂-Ph | pyridin-3-yl |
| IIIa-20 | H | CH₃ | 3-Br-Ph | pyridin-3-yl |
| IIIa-21 | H | CH₃ | 4-NO₂-Ph | pyridin-3-yl |
| IIIa-22 | H | CH₃ | 3-CO₂CH₃-Ph | pyridin-3-yl |
| IIIa-23 | H | H | 4-Cl-Ph | —CH₂-(2,6-di-Cl)-Ph |
| IIIa-24 | H | H | 4-F-Ph | —CH₂-(2,6-di-Cl)-Ph |
| IIIa-25 | H | H | 3-OMe-Ph | —CH₂-(2,6-di-Cl)-Ph |
| IIIa-26 | H | H | 3,5-(OMe)₂-Ph | —CH₂-(2,6-di-Cl)-Ph |
| IIIa-27 | H | H | 3-Br-Ph | —CH₂-(2,6-di-Cl)-Ph |
| IIIa-28 | H | H | Ph | —CH₂-(2,6-di-Cl)-Ph |
| IIIa-29 | H | H | 3-BnO-Ph | —CH₂-(2,6-di-Cl)-Ph |
| IIIa-30 | H | H | 4-NO₂-Ph | —CH₂-(2,6-di-Cl)-Ph |
| IIIa-31 | H | H | 3-CO₂CH₃-Ph | —CH₂-(2,6-di-Cl)-Ph |
| IIIa-32 | H | H | 6-Cl-pyridin-3-yl | —CH₂-(2,6-di-Cl)-Ph |
| IIIa-33 | H | H | cyclohexyl | —CH₂-(2,6-di-Cl)-Ph |
| IIIa-34 | H | CH₂OCH₃ | 3-Cl-Ph | Ph |
| IIIa-35 | H | CH₃ | 3-Cl-Ph | pyridin-3-yl |
| IIIa-36 | H | H | H | 4-CO₂H-phenyl |
| IIIa-37 | H | H | H | 4-Cl-phenyl |
| IIIa-38 | H | H | H | 4-CF₃-phenyl |
| IIIa-39 | H | H | H | 4-CH₃-phenyl |
| IIIa-40 | H | H | H | 2-Cl-phenyl |
| IIIa-41 | H | H | H | 4-OCH₃-phenyl |
| IIIa-42 | H | H | H | 4-CF₃-phenyl |
| IIIa-43 | H | H | H | 2-Cl-phenyl |
| IIIa-44 | H | H | H | 4-OCH₃-phenyl |

TABLE 5-continued

Compounds of Formulae IIIa, IIIb, and IIIc

| No. | G | —T$_{(n)}$—R | R$^1$ | R$^2$ |
|---|---|---|---|---|
| IIIa-45 | H | H | Ph | 4-Cl-phenyl |
| IIIa-46 | H | H | Ph | 4-Cl-phenyl |
| IIIa-47 | H | H | Ph | 4-CF$_3$-phenyl |
| IIIa-48 | H | H | Ph | 4-CF$_3$-phenyl |
| IIIa-49 | H | H | Ph | 4-CH$_3$-phenyl |
| IIIa-50 | H | H | Ph | 4-CH$_3$-phenyl |
| IIIa-51 | H | H | CH$_2$Ph | pyridin-3-yl |
| IIIa-52 | H | H | COPh | CONHCH$_2$Ph |
| IIIa-53 | H | H | SO$_2$Me | CH$_2$Ph |
| IIIa-54 | H | H | Ph | thiazol-2-yl |
| IIIa-55 | H | H | cyclohexyl | piperidin-1-yl |
| IIIa-56 | H | H | cyclohexyl | 4-CONHMe-phenyl |
| IIIa-57 | H | CH$_3$ | H | 4-CO$_2$H-phenyl |
| IIIa-58 | H | CH$_3$ | H | 4-Cl-phenyl |
| IIIa-59 | H | CH$_3$ | H | 4-CF$_3$-phenyl |
| IIIa-60 | H | CH$_3$ | H | 4-CH$_3$-phenyl |
| IIIa-61 | H | CH$_3$ | H | 2-Cl-phenyl |
| IIIa-62 | H | CH$_3$ | H | 4-OCH$_3$-phenyl |
| IIIa-63 | H | CH$_3$ | H | 4-CF$_3$-phenyl |
| IIIa-64 | H | CH$_3$ | H | 2-Cl-phenyl |
| IIIa-65 | H | CH$_3$ | H | 4-OCH$_3$-phenyl |
| IIIa-66 | H | CH$_3$ | Ph | 4-Cl-phenyl |
| IIIa-67 | H | CH$_3$ | Ph | 4-Cl-phenyl |
| IIIa-68 | H | CH$_3$ | Ph | 4-CF$_3$-phenyl |
| IIIa-69 | H | CH$_3$ | Ph | 4-CF$_3$-phenyl |
| IIIa-70 | H | CH$_3$ | Ph | 4-CH$_3$-phenyl |
| IIIa-71 | H | CH$_3$ | Ph | 4-CH$_3$-phenyl |
| IIIa-72 | H | CH$_3$ | CH$_2$Ph | pyridin-3-yl |
| IIIa-73 | H | CH$_3$ | COPh | CONHCH$_2$Ph |
| IIIa-74 | H | CH$_3$ | SO$_2$Me | CH$_2$Ph |
| IIIa-75 | H | CH$_3$ | Ph | thiazol-2-yl |
| IIIa-76 | H | CH$_3$ | cyclohexyl | piperidin-1-yl |
| IIIa-77 | H | CH$_3$ | cyclohexyl | 4-CONHMe-phenyl |
| IIIa-78 | H | CH$_2$OCH$_3$ | H | 4-CO$_2$H-phenyl |
| IIIa-79 | H | CH$_2$OCH$_3$ | H | 4-Cl-phenyl |
| IIIa-80 | H | CH$_2$OCH$_3$ | H | 4-CF$_3$-phenyl |
| IIIa-81 | H | CH$_2$OCH$_3$ | H | 4-CH$_3$-phenyl |
| IIIa-82 | H | CH$_2$OCH$_3$ | H | 2-Cl-phenyl |
| IIIa-83 | H | CH$_2$OCH$_3$ | H | 4-OCH$_3$-phenyl |
| IIIa-84 | H | CH$_2$OCH$_3$ | H | 4-CF$_3$-phenyl |
| IIIa-85 | H | CH$_2$OCH$_3$ | H | 2-Cl-phenyl |
| IIIa-86 | H | CH$_2$OCH$_3$ | H | 4-OCH$_3$-phenyl |
| IIIa-87 | H | CH$_2$OCH$_3$ | Ph | 4-Cl-phenyl |
| IIIa-88 | H | CH$_2$OCH$_3$ | Ph | 4-Cl-phenyl |
| IIIa-89 | H | CH$_2$OCH$_3$ | Ph | 4-CF$_3$-phenyl |
| IIIa-90 | H | CH$_2$OCH$_3$ | Ph | 4-CF$_3$-phenyl |
| IIIa-91 | H | CH$_2$OCH$_3$ | Ph | 4-CH$_3$-phenyl |
| IIIa-92 | H | CH$_2$OCH$_3$ | Ph | 4-CH$_3$-phenyl |
| IIIa-93 | H | CH$_2$OCH$_3$ | CH$_2$Ph | pyridin-3-yl |
| IIIa-94 | H | CH$_2$OCH$_3$ | COPh | CONHCH$_2$Ph |
| IIIa-95 | H | CH$_2$OCH$_3$ | SO$_2$Me | CH$_2$Ph |
| IIIa-96 | H | CH$_2$OCH$_3$ | Ph | thiazol-2-yl |
| IIIa-97 | H | CH$_2$OCH$_3$ | cyclohexyl | piperidin-1-yl |
| IIIa-98 | H | CH$_2$OCH$_3$ | cyclohexyl | 4-CONHMe-phenyl |
| IIIb-1 | H | — | 4-Cl-phenyl | Ph |
| IIIb-2 | H | — | 4-F-phenyl | Ph |
| IIIb-3 | H | — | 3-OMe-Ph | Ph |
| IIIb-4 | H | — | 3,5-(OMe)$_2$-Ph | Ph |
| IIIb-5 | H | — | Ph | Ph |
| IIIb-6 | H | — | 3-BnO-Ph | Ph |
| IIIb-7 | H | — | 4-NO$_2$-Ph | Ph |
| IIIb-8 | H | — | 3-Br-Ph | Ph |
| IIIb-9 | H | — | 3-CO$_2$CH$_3$-Ph | Ph |
| IIIb-10 | H | — | cyclohexyl | Ph |
| IIIb-11 | H | — | 4-Cl-phenyl | 2-OBn-Ph |
| IIIb-12 | H | — | 3-NO$_2$-Ph | 2-OBn-Ph |
| IIIb-13 | H | — | CH$_2$-phenyl | 2-OBn-Ph |
| IIIb-14 | H | — | cyclohexyl | 2-OBn-Ph |
| IIIb-15 | H | — | 3-OMe-Ph | 2-OBn-Ph |
| IIIb-16 | H | — | 3,5-(OMe)$_2$-Ph | 2-OBn-Ph |
| IIIb-17 | H | — | 4-Cl-phenyl | cyclohexyl |
| IIIb-18 | H | — | 3-Cl-phenyl | Ph |
| IIIb-19 | H | — | H | 4-CO$_2$H-phenyl |
| IIIb-20 | H | — | H | 4-Cl-phenyl |
| IIIb-21 | H | — | H | 4-CF$_3$-phenyl |
| IIIb-22 | H | — | H | 4-CH$_3$-phenyl |
| IIIb-23 | H | — | H | 2-Cl-phenyl |
| IIIb-24 | H | — | H | 4-OCH$_3$-phenyl |
| IIIb-25 | H | — | H | 4-CF$_3$-phenyl |
| IIIb-26 | H | — | H | 2-Cl-phenyl |
| IIIb-27 | H | — | H | 4-OCH$_3$-phenyl |
| IIIb-28 | H | — | Ph | 4-Cl-phenyl |
| IIIb-29 | H | — | Ph | 4-Cl-phenyl |
| IIIb-30 | H | — | Ph | 4-CF$_3$-phenyl |
| IIIb-31 | H | — | Ph | 4-CF$_3$-phenyl |
| IIIb-32 | H | — | Ph | 4-CH$_3$-phenyl |
| IIIb-33 | H | — | Ph | 4-CH$_3$-phenyl |
| IIIb-34 | H | — | CH$_2$Ph | pyridin-3-yl |
| IIIb-35 | H | — | COPh | CONHCH$_2$Ph |
| IIIb-36 | H | — | SO$_2$Me | CH$_2$Ph |
| IIIb-37 | H | — | Ph | thiazol-2-yl |
| IIIb-38 | H | — | cyclohexyl | piperidin-1-yl |
| IIIb-39 | H | — | cyclohexyl | 4-CONHMe-phenyl |
| IIIc-1 | H | — | 4-Cl-phenyl | Ph |
| IIIc-2 | H | — | 4-F-phenyl | Ph |
| IIIc-3 | H | — | 3-OMe-Ph | Ph |
| IIIc-4 | H | — | 3,5-(OMe)$_2$-Ph | Ph |
| IIIc-5 | H | — | Ph | Ph |
| IIIc-6 | H | — | 3-BnO-Ph | Ph |
| IIIc-7 | H | — | 4-NO$_2$-Ph | Ph |
| IIIc-8 | H | — | 3-Br-Ph | Ph |
| IIIc-9 | H | — | 3-CO$_2$CH$_3$-Ph | Ph |
| IIIc-10 | H | — | cyclohexyl | Ph |
| IIIc-11 | H | — | 4-Cl-phenyl | 2-OBn-Ph |
| IIIc-12 | H | — | 3-NO$_2$-Ph | 2-OBn-Ph |
| IIIc-13 | H | — | CH$_2$-phenyl | 2-OBn-Ph |
| IIIc-14 | H | — | cyclohexyl | 2-OBn-Ph |
| IIIc-15 | H | — | 3-OMe-Ph | 2-OBn-Ph |
| IIIc-16 | H | — | 3,5-(OMe)$_2$-Ph | 2-OBn-Ph |
| IIIc-17 | H | — | 4-Cl-phenyl | cyclohexyl |
| IIIc-18 | H | — | 3-Cl-phenyl | Ph |
| IIIc-19 | H | — | H | 4-CO$_2$H-phenyl |
| IIIc-20 | H | — | H | 4-Cl-phenyl |
| IIIc-21 | H | — | H | 4-CF$_3$-phenyl |
| IIIc-22 | H | — | H | 4-CH$_3$-phenyl |
| IIIc-23 | H | — | H | 2-Cl-phenyl |
| IIIc-24 | H | — | H | 4-OCH$_3$-phenyl |
| IIIc-25 | H | — | H | 4-CF$_3$-phenyl |
| IIIc-26 | H | — | H | 2-Cl-phenyl |
| IIIc-27 | H | — | H | 4-OCH$_3$-phenyl |
| IIIc-28 | H | — | Ph | 4-Cl-phenyl |
| IIIc-29 | H | — | Ph | 4-Cl-phenyl |
| IIIc-30 | H | — | Ph | 4-CF$_3$-phenyl |
| IIIc-31 | H | — | Ph | 4-CF$_3$-phenyl |
| IIIc-32 | H | — | Ph | 4-CH$_3$-phenyl |
| IIIc-33 | H | — | Ph | 4-CH$_3$-phenyl |
| IIIc-34 | H | — | CH$_2$Ph | pyridin-3-yl |
| IIIc-35 | H | — | COPh | CONHCH$_2$Ph |
| IIIc-36 | H | — | SO$_2$Me | CH$_2$Ph |
| IIIc-37 | H | — | Ph | thiazol-2-yl |
| IIIc-38 | H | — | cyclohexyl | piperidin-1-yl |
| IIIc-39 | H | — | cyclohexyl | 4-CONHMe-phenyl |

A more preferred embodiment relates to compounds of formula IVa:

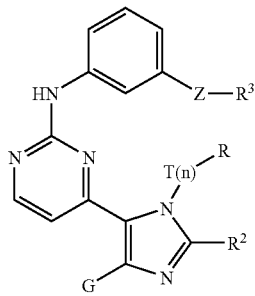

IVa or a pharmaceutically acceptable derivative thereof, wherein $R^2$, $R^3$, n, T, R, and G are as defined above.

Preferred $R^2$, $R^3$, n, T, R and G groups of formula IVa are those described above for formula IIa.

Preferred -Z-$R^3$ groups of the $Ar^1$ group of formula I are those wherein Z is a $C_{1-4}$ alkylidene chain wherein one methylene unit of Z is optionally replaced by —O—, —NH—, —NHC(O)—, —NHC(O)O—, —NHSO$_2$—, —C(O)NH—, or wherein $R^3$ is selected from —N(R)$_2$, —NHC(O)R, or $Ar^3$ wherein $Ar^3$ is a 5-6 membered heterocyclic or heteroaryl ring having one to two heteroatoms independently selected from nitrogen, oxygen, or sulfur. The $Ar^3$ group is optionally substituted with —R', —OR', —N(R')$_2$, or oxo. More preferred Z-$R^3$ groups of the $Ar^1$ group of formula IVa are selected from —O—CH$_2$-phenyl, —O(CH$_2$)$_3$OH, —O(CH$_2$)$_3$NH(CH$_2$)$_2$OH, —O(CH$_2$)$_2$NH (CH$_2$)$_2$OH, —O(CH$_2$)$_3$N(hydroxyethyl) (methyl), —O(CH$_2$)$_3$pyrrolidin-1-yl, —O(CH$_2$)$_2$morpholin-4-yl, —O(CH$_2$)$_3$N(Me)$_2$, —O(CH$_2$)$_3$N(Et)$_2$, —O(CH$_2$)$_3$(4-hydroxyethyl piperazin-1-yl), —O(CH$_2$)$_3$piperazin-1-yl, —O(CH$_2$)$_3$(4-hydroxymethylpiperidin-1-yl), —O(CH$_2$)$_3$(4-hydroxypiperidin-1-yl), —NHCO(CH$_2$)$_3$N(Me)$_2$, —NHCO (CH$_2$)$_3$NCOCH$_3$, —NHCOCH$_2$pyridin-2-yl, —NHCOCH$_2$ (2-aminothiazol-4-yl), NHCOCH$_2$cyclopropyl, —NHCO (CH$_2$)$_2$N(Et)$_2$, —NHCO(CH$_2$)$_2$-(piperazin-2,5-dione-3-yl), —NHC(O)-pyrrolidin-1-yl, —NHCOmorpholin-4-yl, —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl.

Preferred compounds of formula IVa are those having one or more, more preferably more than one, and most preferably all, of the features selected from the group consisting of:

(a) $R^2$ is $Ar^2$ or —CH$_2$—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted by wherein $Ar^2$ is optionally substituted with one to five groups independently selected from -Z-$R^3$, —R, halogen, —NO$_2$, —CN, —OR, —SR, —N(R)$_2$, —NRC(O)R, —NRC(O)N(R)$_2$, —NRCO$_2$R, —C(O)R, —CO$_2$R, —C(O)N(R)$_2$, —OC(O)N(R)$_2$, —S(O)R, —SO$_2$R, —SO$_2$N(R)$_2$, —N(R)SO$_2$R, —N(R)SO$_2$N(R)$_2$, —C(O)C(O)R, or —C(O)CH$_2$C(O)R;

(b) G is hydrogen;

(c) Z is a $C_{1-4}$ alkylidene chain wherein one methylene unit of Z is optionally replaced by —O—, —NH—, —NHC(O)—, —NHC(O)O—, —NHSO$_2$—, —C(O)NH—; and (d) $R^3$ is selected from —N(R)$_2$, —NHC(O)R, or $Ar^3$ wherein $Ar^3$ is a 5-6 membered heterocyclic or heteroaryl ring having one to two heteroatoms independently selected from nitrogen, oxygen, or sulfur and $Ar^3$ is optionally substituted with —R', —OR', —N(R')$_2$, or oxo.

More preferred compounds of formula IVa are those having one or more, more preferably more than one, and most preferably all, of the features selected from the group consisting of:

(a) $R^2$ is selected from phenyl, pyridyl, pyrimidinyl, cyclohexyl, piperidinyl, furanyl, or benzyl, wherein each member of $R^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —NH$_2$, methyl, methoxy, or ethoxy;

(b) G is hydrogen; and (c)-Z-$R^3$ is selected from —O—CH$_2$-phenyl, —O(CH$_2$)$_3$OH, —O(CH$_2$)$_3$NH(CH$_2$)$_2$OH, —O(CH$_2$)$_2$NH(CH$_2$)$_2$OH, —O(CH$_2$)$_3$N (hydroxyethyl) (methyl), —O(CH$_2$)$_3$ pyrrolidin-1-yl, —O(CH$_2$)$_2$morpholin-4-yl, —O(CH$_2$)$_3$N(Me)$_2$, —O(CH$_2$)$_3$N(Et)$_2$, —O(CH$_2$)$_3$ (4-hydroxyethyl piperazin-1-yl), —O(CH$_2$)$_3$piperazin-1-yl, —O(CH$_2$)$_3$(4-hydroxymethylpiperidin-1-yl), —O(CH$_2$)$_3$(4-hydroxypiperidin-1-yl), —NHCO (CH$_2$)$_3$ N(Me)$_2$, —NHCO(CH$_2$)$_3$NCOCH$_3$, —NHCOCH$_2$pyridin-2-yl, —NHCOCH$_2$(2-aminothiazol-4-yl), —NHCOCH$_2$cyclopropyl, —NHCO(CH$_2$)$_2$ N(Et)$_2$, —NHCO(CH$_2$)$_2$-(piperazin-2,5-dione-3-yl), —NHC(O)pyrrolidin-1-yl, —NHCOmorpholin-4-yl, —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl.

Exemplary structures of formula IVa are set forth in Table 6 below.

TABLE 5

Compounds of Formula IVa

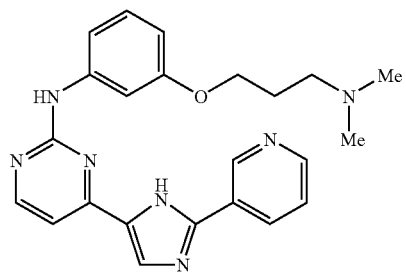

IVa-1

TABLE 5-continued
Compounds of Formula IVa
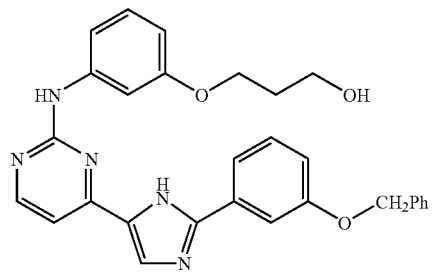
IVa-2
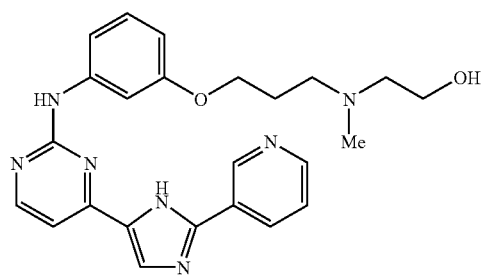
IVa-3
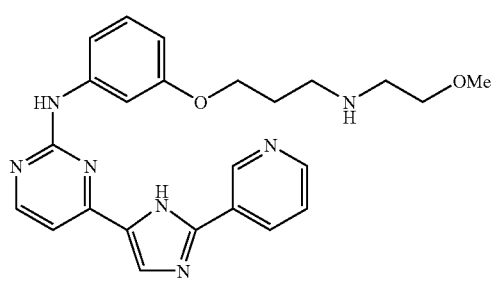
IVa-4
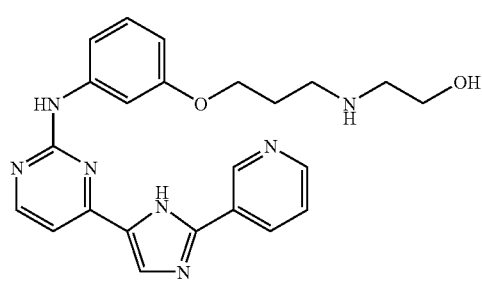
IVa-5
TABLE 5-continued
Compounds of Formula IVa
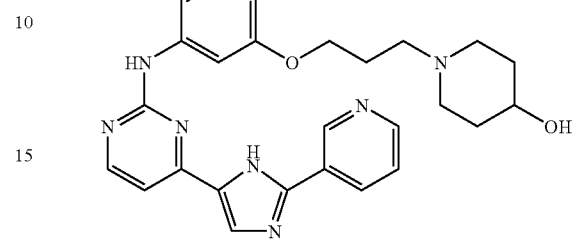
IVa-6
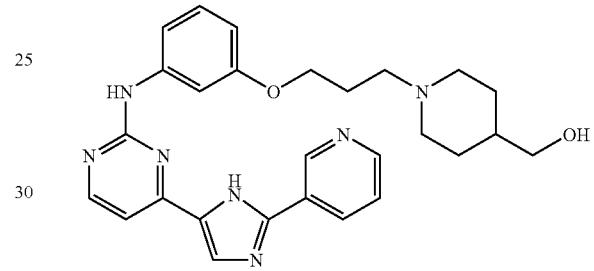
IVa-7
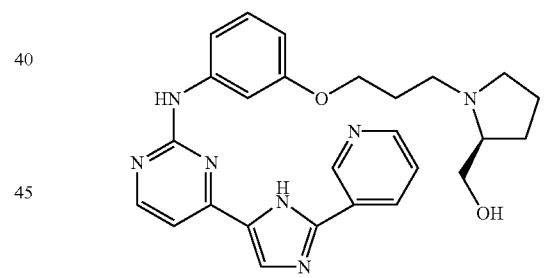
IVa-8
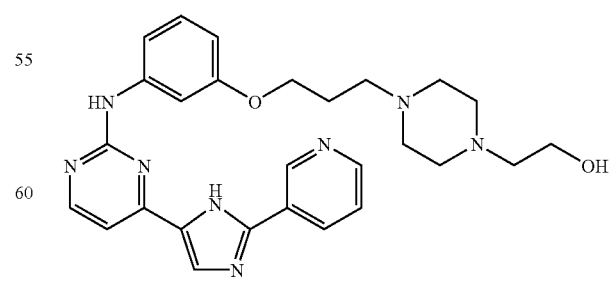
IVa-9

TABLE 5-continued
Compounds of Formula IVa
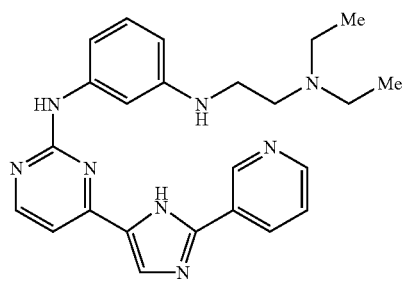
IVa-10
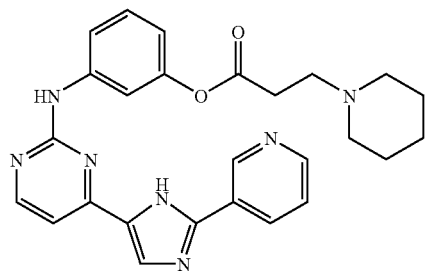
IVa-11
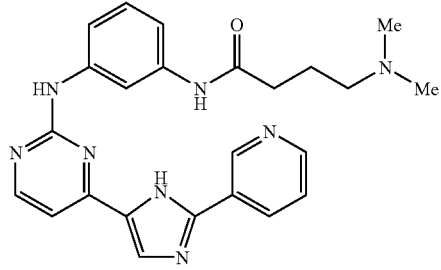
IVa-12
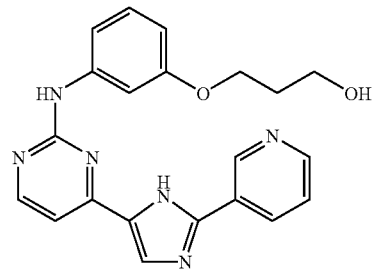
IVa-13
TABLE 5-continued
Compounds of Formula IVa
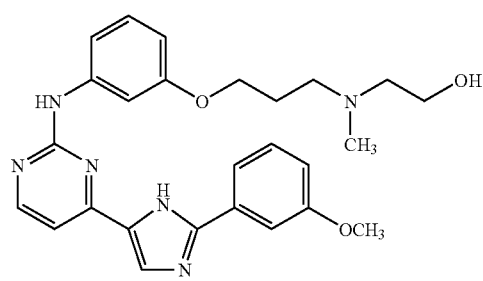
IVa-14
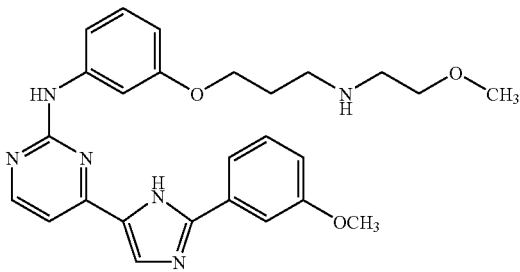
IVa-15
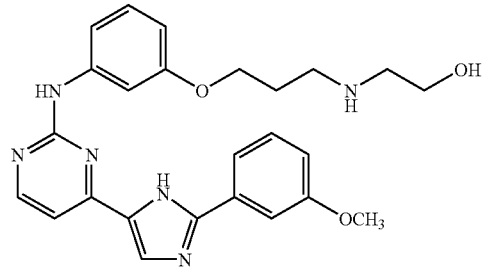
IVa-16
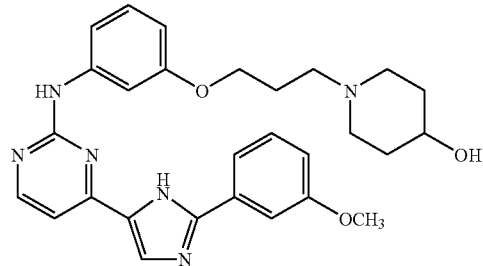
IVa-17

TABLE 5-continued
Compounds of Formula IVa
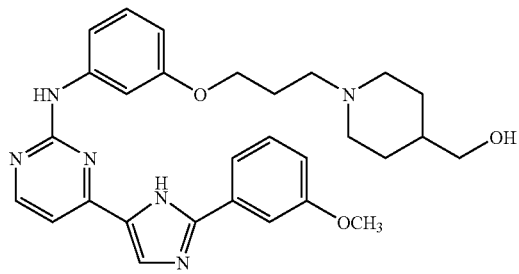
IVa-18
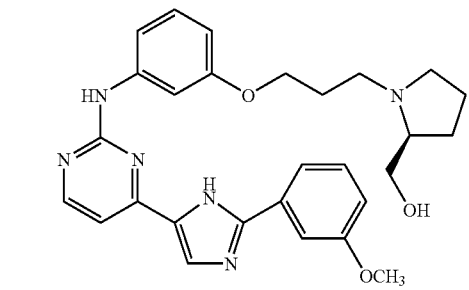
IVa-19
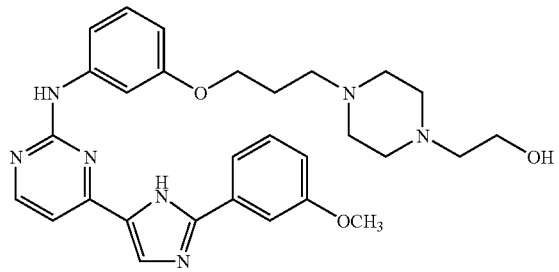
IVa-20
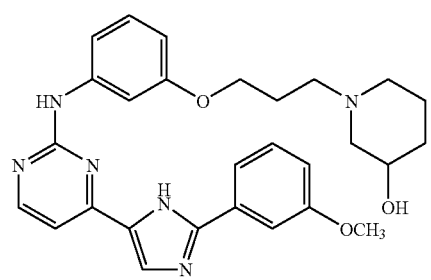
IVa-21
TABLE 5-continued
Compounds of Formula IVa
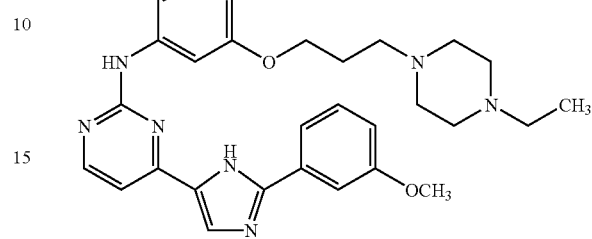
IVa-22
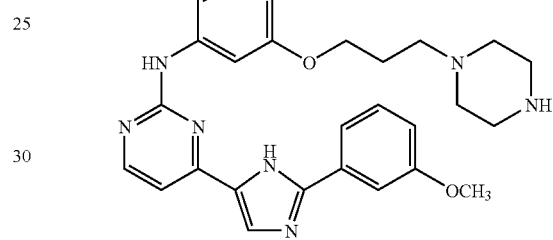
IVa-23
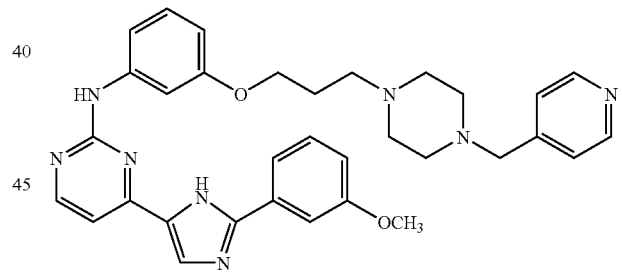
IVa-24
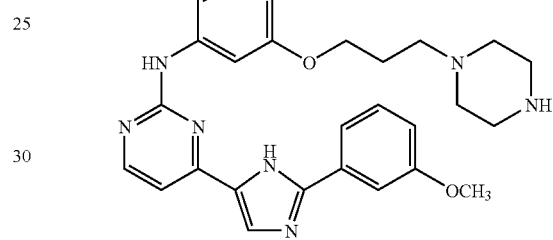
IVa-25

TABLE 5-continued
Compounds of Formula IVa
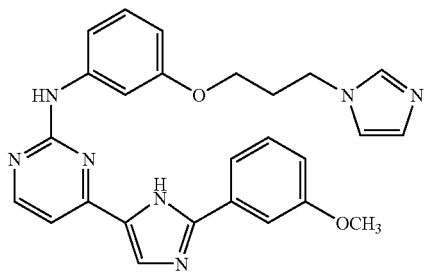
IVa-26
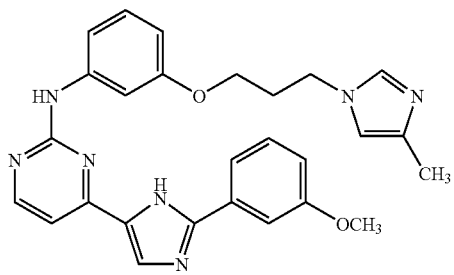
IVa-27
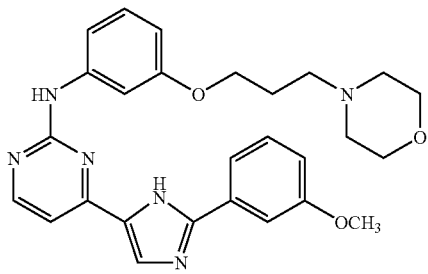
IVa-28
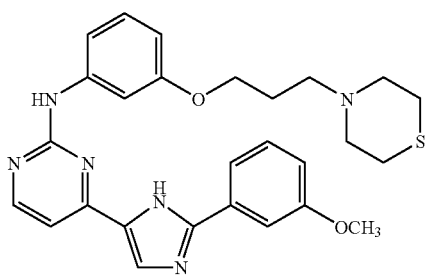
IVa-29
TABLE 5-continued
Compounds of Formula IVa
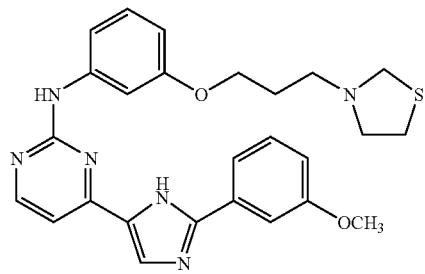
IVa-30
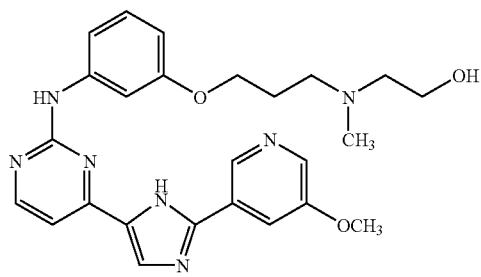
IVa-31
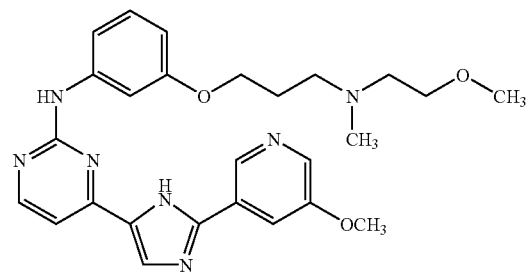
IVa-32
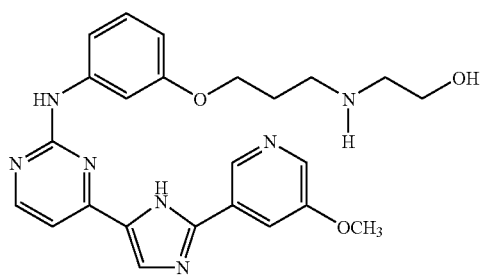
IVa-33

TABLE 5-continued
Compounds of Formula IVa
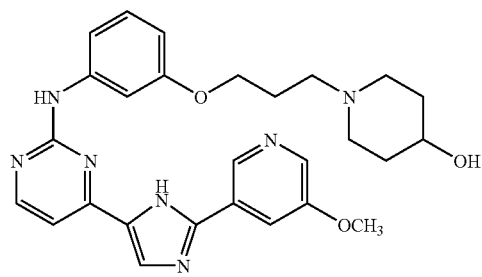
IVa-34
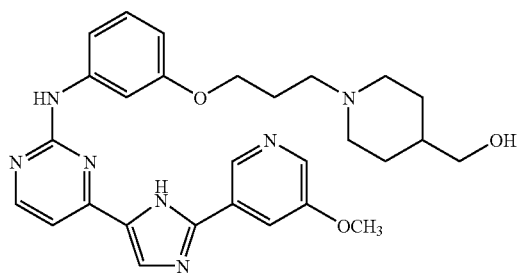
IVa-35
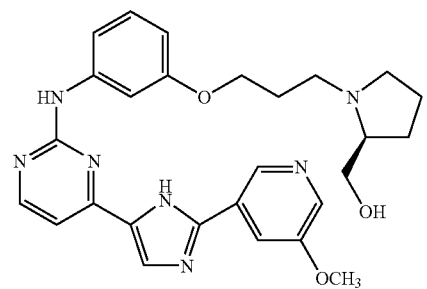
IVa-36
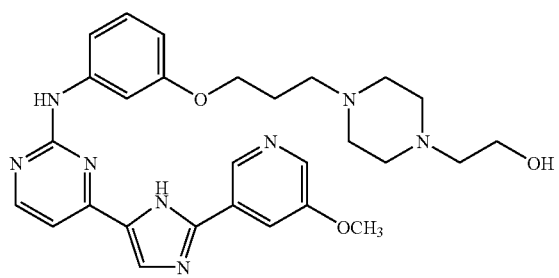
IVa-37
TABLE 5-continued
Compounds of Formula IVa
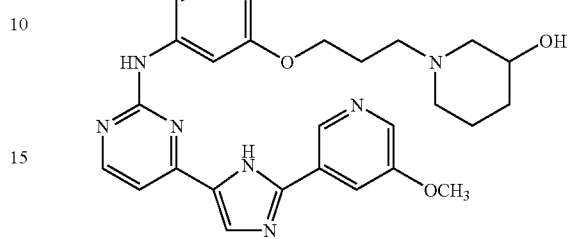
IVa-38
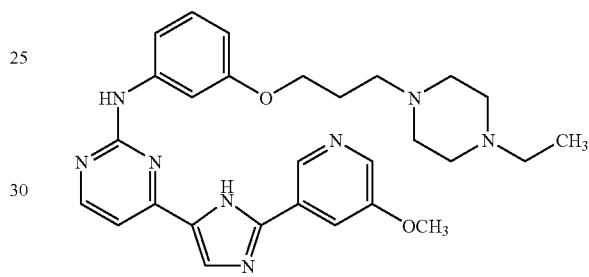
IVa-39
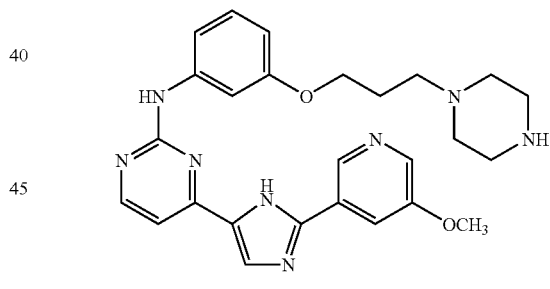
IVa-40
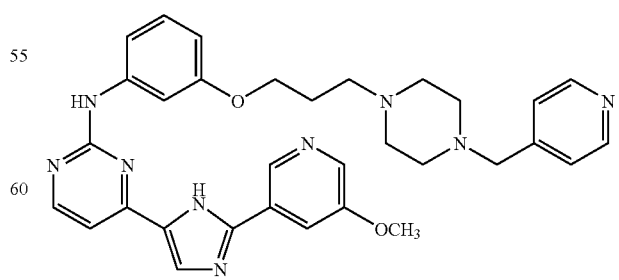
IVa-41

TABLE 5-continued
Compounds of Formula IVa
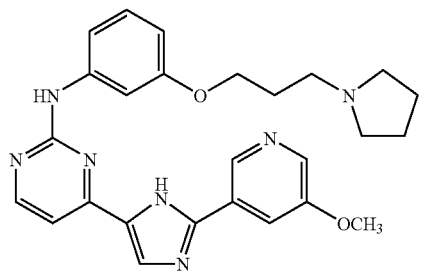
IVa-42
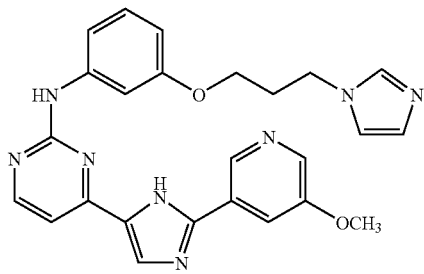
IVa-43
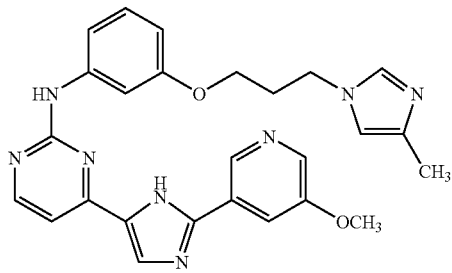
IVa-44
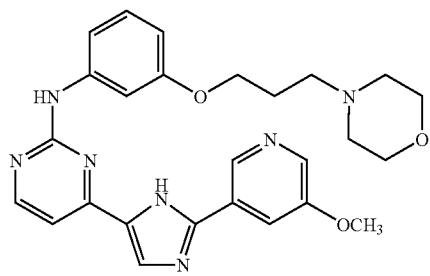
IVa-45
TABLE 5-continued
Compounds of Formula IVa
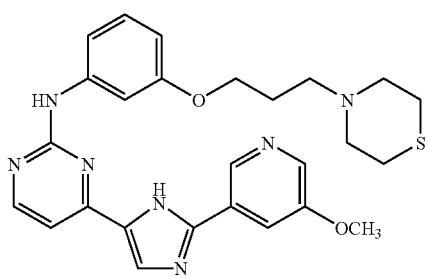
IVa-46
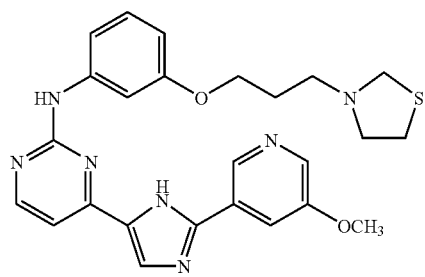
IVa-47
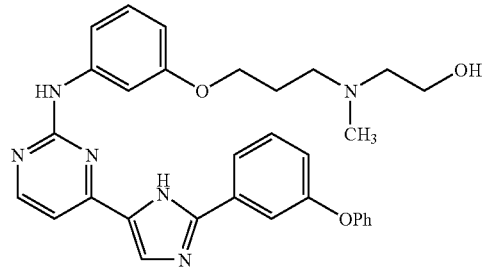
IVa-48
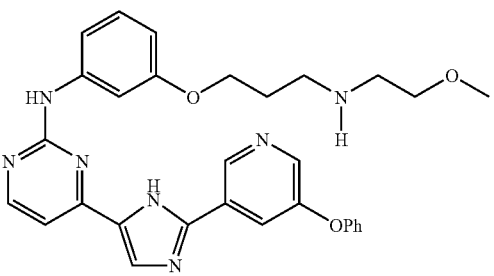
IVa-49

TABLE 5-continued
Compounds of Formula IVa
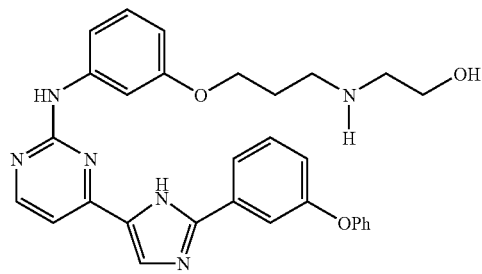
IVa-50
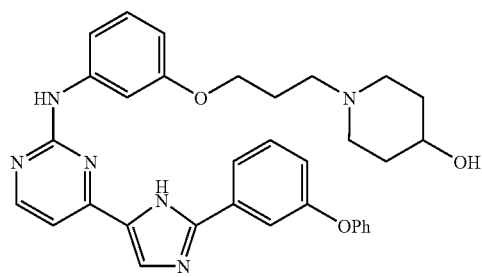
IVa-51
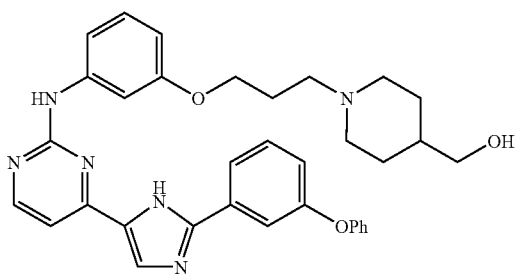
IVa-52
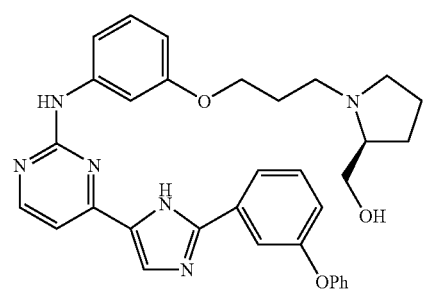
IVa-53
TABLE 5-continued
Compounds of Formula IVa
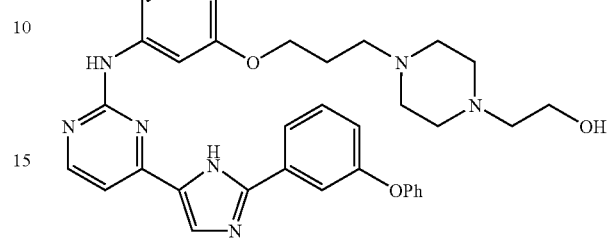
IVa-54
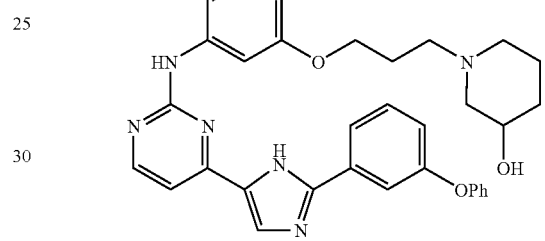
IVa-55
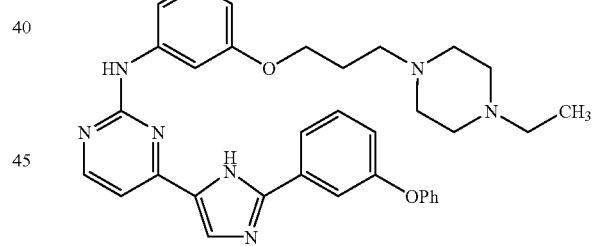
IVa-56
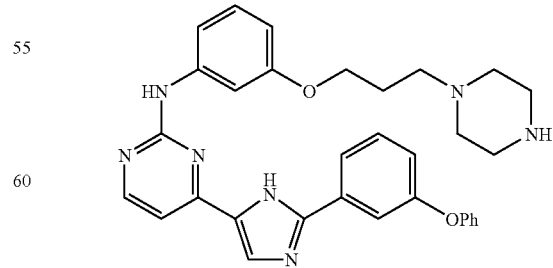
IVa-57

TABLE 5-continued
Compounds of Formula IVa
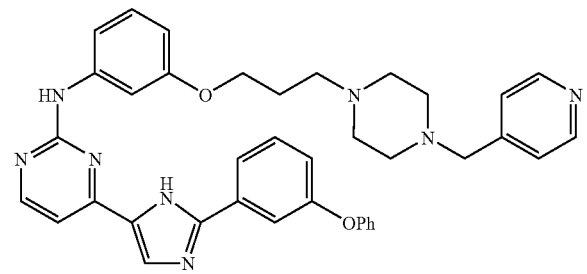
IVa-58
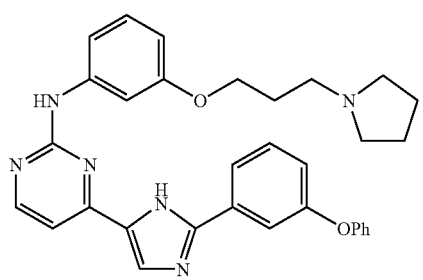
IVa-59
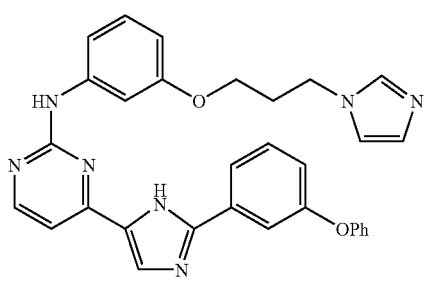
IVa-60
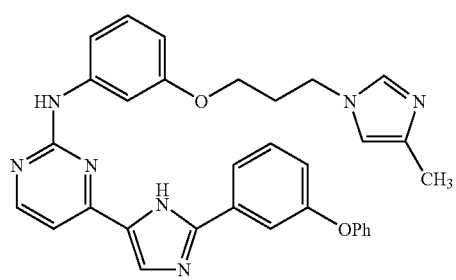
IVa-61
TABLE 5-continued
Compounds of Formula IVa
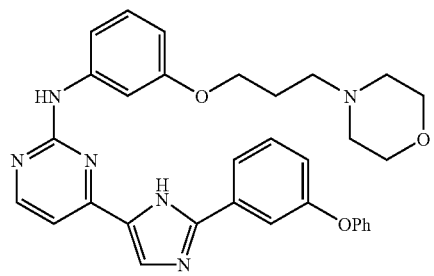
IVa-62
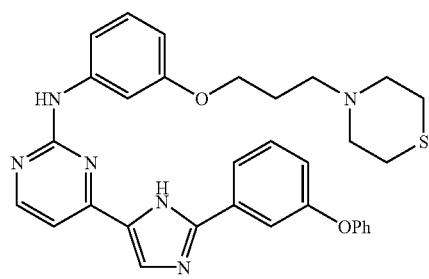
IVa-63
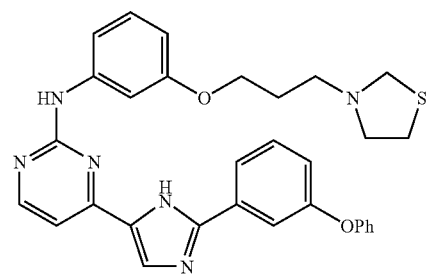
IVa-64
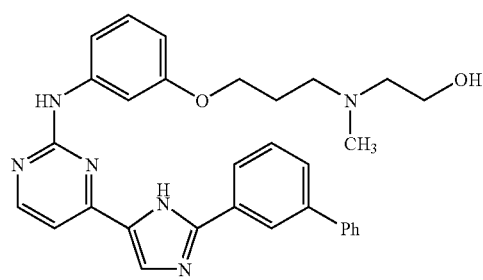
IVa-65

TABLE 5-continued
Compounds of Formula IVa
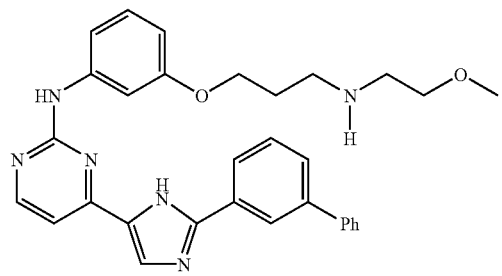
IVa-66
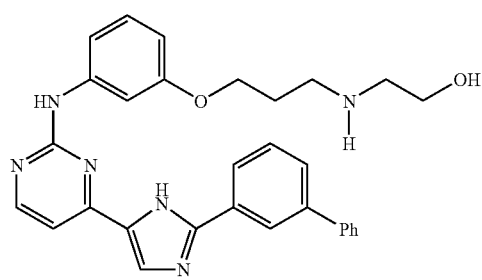
IVa-67
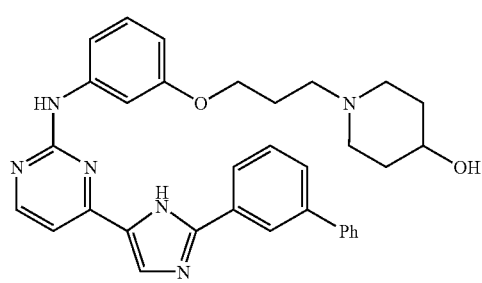
IVa-68
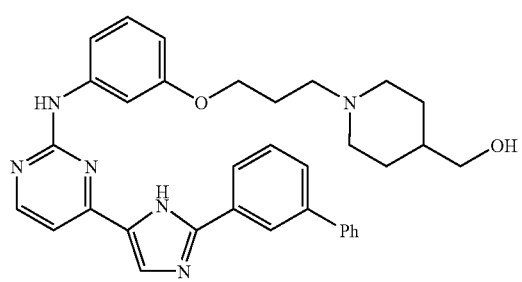
IVa-69
TABLE 5-continued
Compounds of Formula IVa
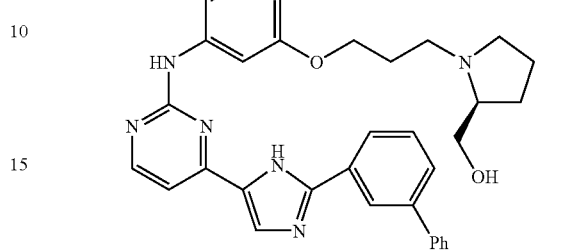
IVa-70
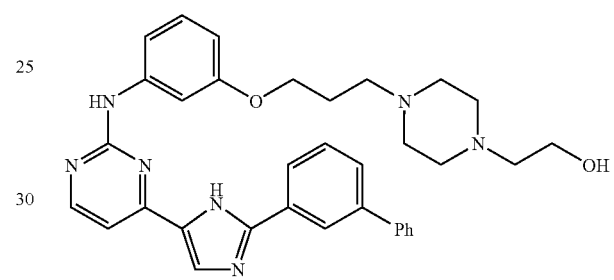
IVa-71
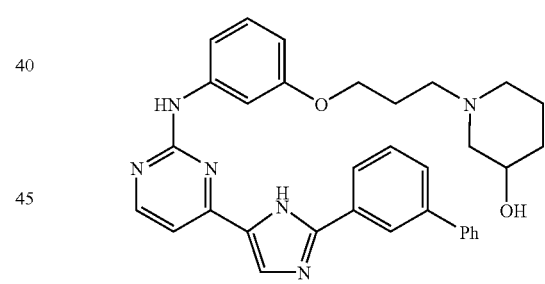
IVa-72
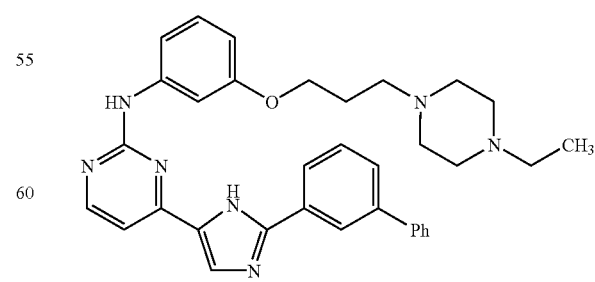
IVa-73

TABLE 5-continued

Compounds of Formula IVa

IVa-74

IVa-75

IVa-76

IVa-77

TABLE 5-continued

Compounds of Formula IVa

IVa-78

IVa-79

IVa-80

IVa-81

TABLE 5-continued
Compounds of Formula IVa
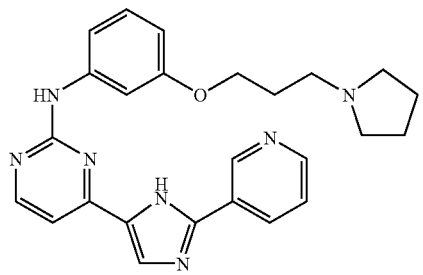
IVa-82
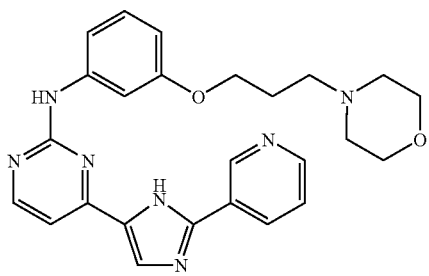
IVa-83
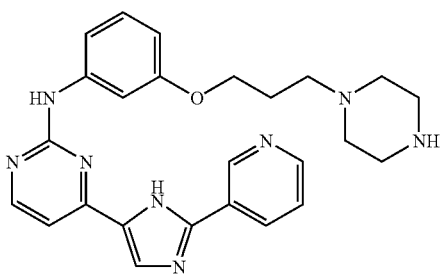
IVa-84
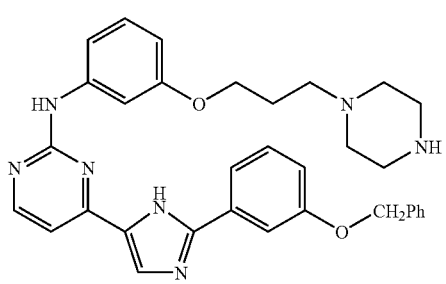
IVa-85
TABLE 5-continued
Compounds of Formula IVa
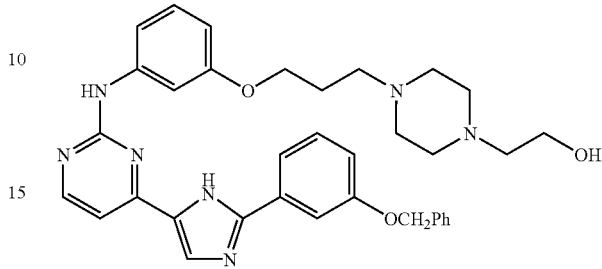
IVa-86
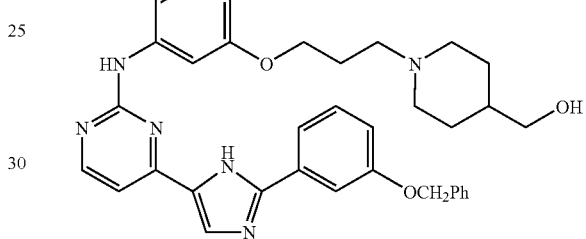
IVa-87
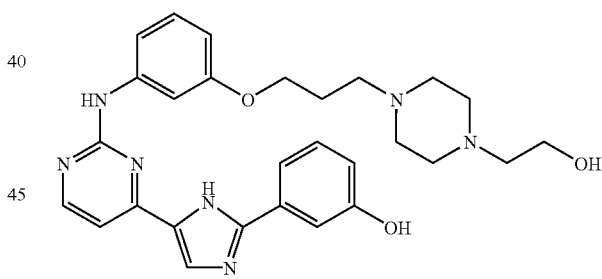
IVa-88
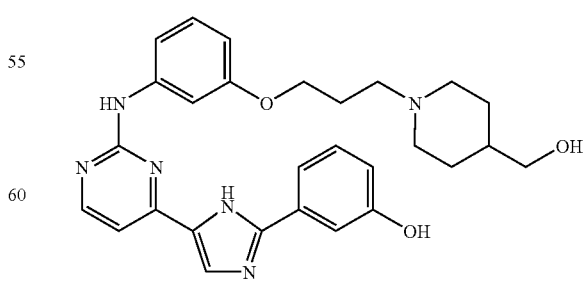
IVa-89

TABLE 5-continued
Compounds of Formula IVa
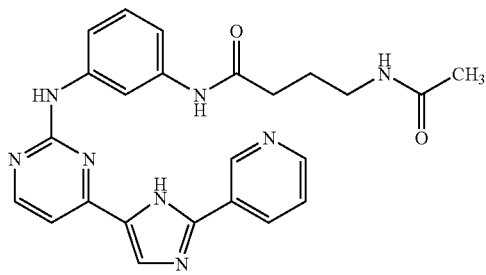
IVa-90
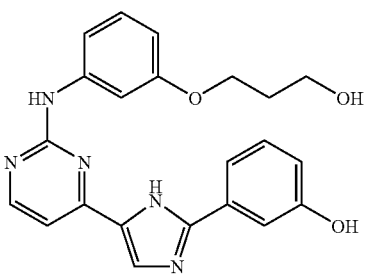
IVa-91
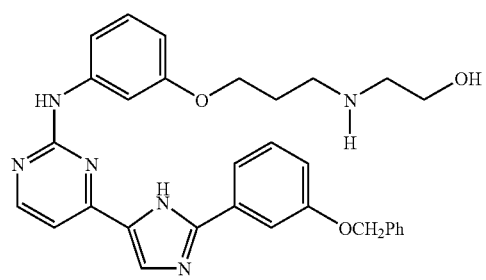
IVa-92
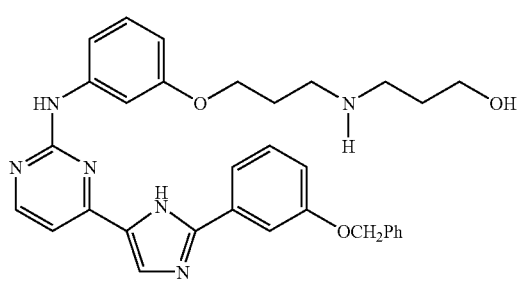
IVa-93
TABLE 5-continued
Compounds of Formula IVa
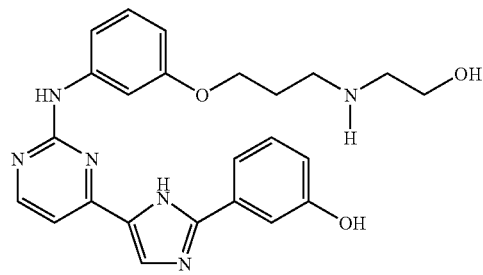
IVa-94
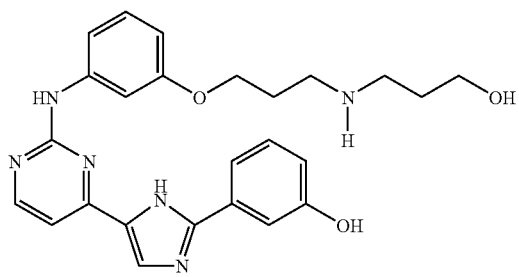
IVa-95
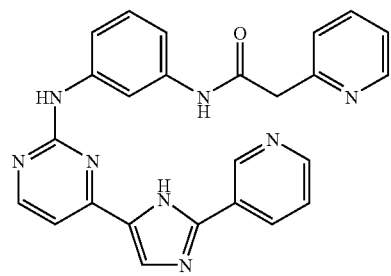
IVa-96
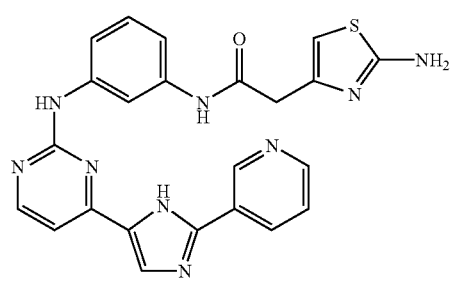
IVa-97

TABLE 5-continued
Compounds of Formula IVa
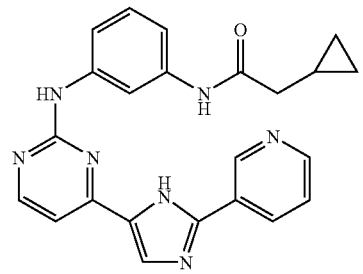
IVa-98
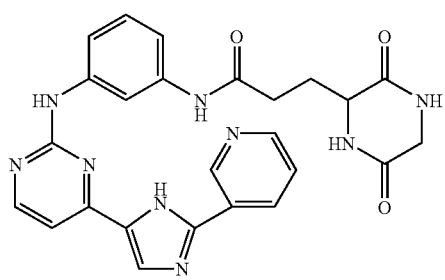
IVa-99
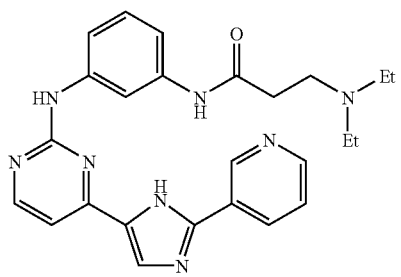
IVa-100
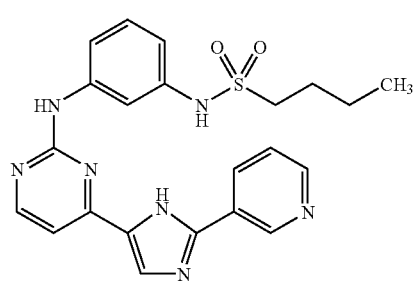
IVa-101
TABLE 5-continued
Compounds of Formula IVa
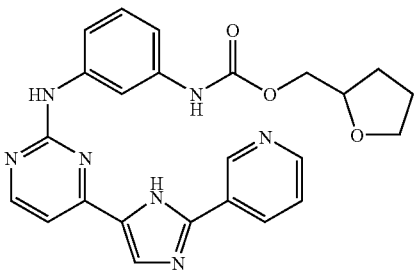
IVa-102
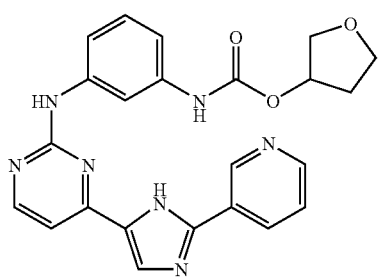
IVa-103
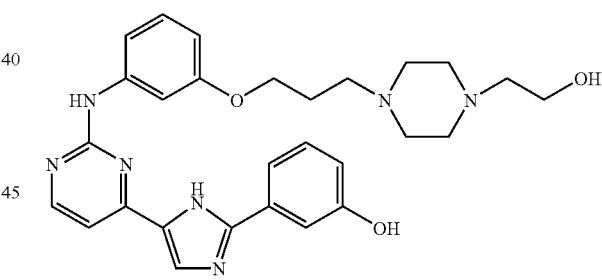
IVa-104
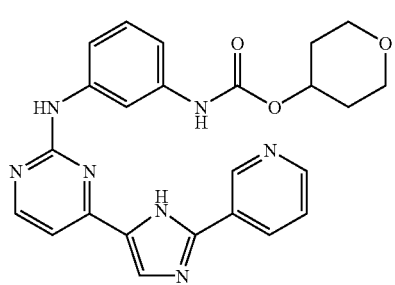
IVa-105

TABLE 5-continued
Compounds of Formula IVa
IVa-106
IVa-107
Other more preferred embodiments relate to compounds of formulae IVb and IVc:
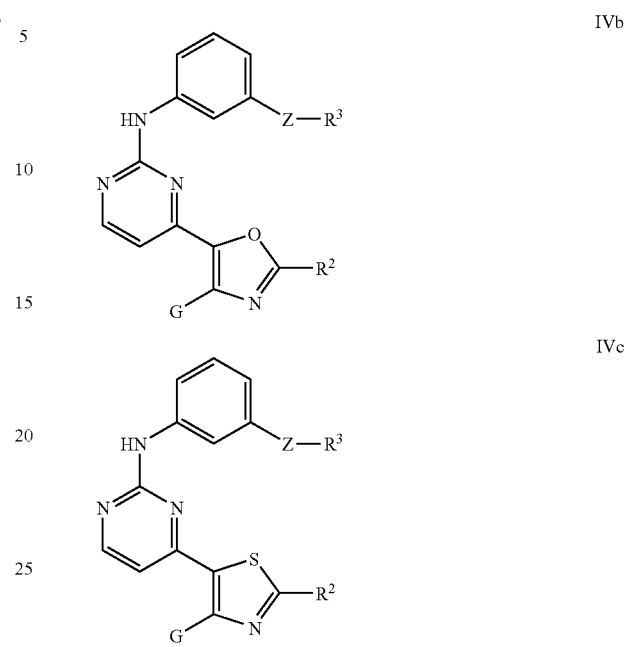
Preferred $R^2$, -Z-$R^3$, and G groups of the compounds of formulae IVb and IVc are as described above for the formula IVa compounds.
Scheme I
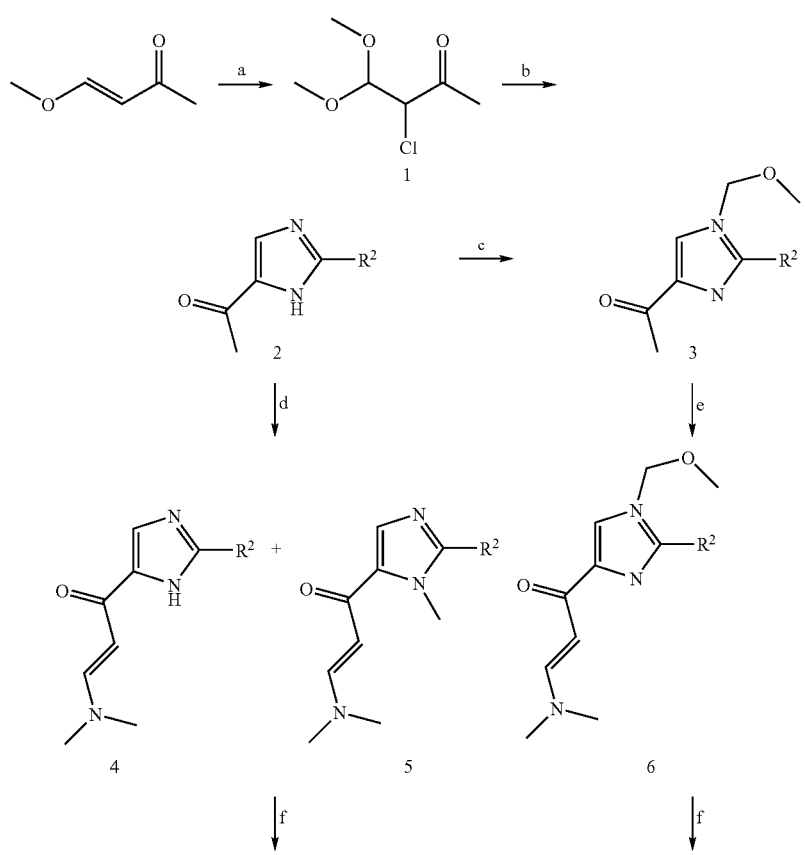

-continued

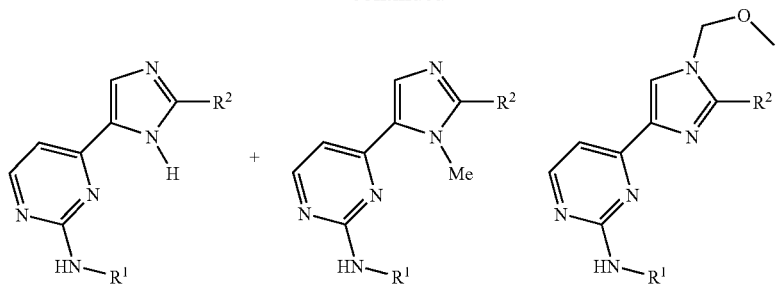

IIa    IIa    IIa

Reagents and conditions:
(a) Cl$_2$ (gas), MeOH, pyridine, r.t.;
(b) 1,4-dioxane, CH$_3$COONa, amidines, reflux;
(c) LDA, -78° C. to r.t., THF, then MOMCl;
(d) (CH$_3$)$_2$NCH(OCH$_3$), toluene, 90° C. ;
(e) (CH$_3$)$_2$NCH(OCH$_3$), CH$_3$CN, dimethylamine, reflux; and
(f) MeONa, MeOH, guanidines, reflux.

Scheme I above shows a general synthetic route that is used for preparing the compounds of formula I where A is —N-T$_{(n)}$—R (formula IIa). The details of the conditions used for producing these compounds are set forth in the Examples.

Scheme II

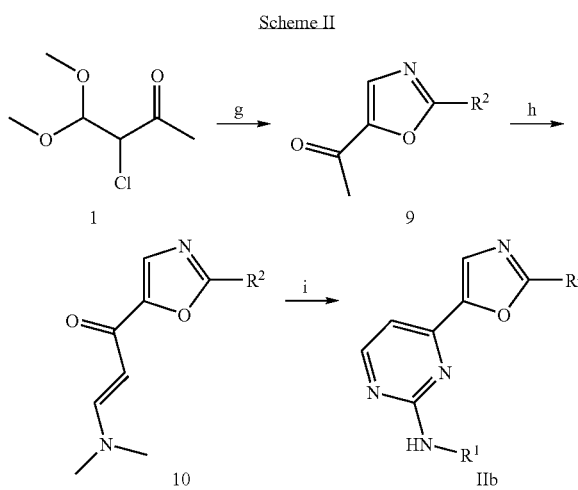

Reagents and conditions:
(g) CH$_3$COOH, amides, 120° C.;
(h) (CH$_3$)$_2$NCH(OCH$_3$), toluene, 90° C.; and
(i) MeONa, MeOH, guanidines, reflux.

Scheme II above shows a general synthetic route that is used for preparing the compounds of formula I where A is oxygen (formula IIb). Scheme II can also be used to prepare compounds of formula I where A is sulfur (formula IIc) when amides in step (g) are replaced by thioamides. The details of the conditions used for producing these compounds are set forth in the Examples.

One of skill in the art may synthesize other compounds of the present invention following the teachings of the specification using reagents that are readily synthesized or commerically available.

According to another embodiment, the invention provides a method of inhibiting JNK, Src, Lck, or Aurora-2 kinase activity in a biological sample. This method comprises the step of contacting said biological sample with a compound of formula I. According to a preferred embodiment, the invention relates to a method of inhibiting JNK, Src, Lck, or Aurora-2 kinase activity in a biological sample comprising the step of contacting said biological sample with a compound of formula IIa, IIb, IVa, or IVb.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JNK, Src, Lck, or Aurora-2 kinase activity in a biological sample is useful for a variety of purposes which are known to one of skill in the art. Examples of such purposes include, but are not limited to, blood transfusion, organ-translplantation, biological specimen storage, and biological assays.

Compounds of formula I or derivatives (e.g., salts) thereof may be formulated into compositions. In a preferred embodiment, the composition is a pharmaceutically acceptable composition. In one embodiment, the composition comprises an amount of a compound effective to inhibit a protein kinase, particularly JNK, Src, Lck, or Aurora-2, in a biological sample or in a patient. In another embodiment, compounds of this invention and pharmaceutical compositions thereof, which comprise an amount of the compound effective to treat or prevent an JNK, Src, Lck, or Aurora-2-mediated condition and a pharmaceutically acceptable carrier, adjuvant, or vehicle, may be formulated for administration to a patient.

The amount effective to inhibit protein kinase, for example, JNK, Src, Lck, or Aurora-2, is one that measurably inhibits the kinase activity where compared to the activity of the enzyme in the absence of an inhibitor. "Measurable inhibition" means a measurable change in activity between a sample containing said inhibitor and a sample containing said protein kinase only. Any method may be used to determine inhibition, such as, for example, the biological testing examples described below.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

Pharmaceutically acceptable carriers that may be used in these pharmaceutical compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, favoring or coloring agents may also be added.

Alternatively, the pharmaceutical compositions of this invention may be administered in the form of suppositories for rectal administration. These can be prepared by mixing the agent with a suitable nonirritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to a preferred embodiment, the pharmaceutical compositions of this invention are orally administered.

According to another embodiment, the present invention relates to a pharmaceutically acceptable derivative of a compound of formula I. In a preferred embodiment, said pharmaceutically acceptable derivative is of a compound of formula IIa, IIb, IVa, or IVb.

In addition to the compounds of this invention, pharmaceutically acceptable derivatives of the compounds of this invention may also be employed in compositions to treat or prevent the diseases or disorders identified herein.

A "pharmaceutically acceptable derivative" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. The methods for preparing salts or esters of a compound of this invention are known to one of skill in the art. Particularly favored derivatives are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable derivatives of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The dosage of compound will also depend upon which particular compound is in the composition.

The compounds of this invention are inhibitors of JNK, Src, Lck, or Aurora-2 kinase as determined by enzymatic assay. Accordingly, these compounds are useful for treating JNK-, Src-, Lck-, or Aurora-2-mediated diseases or conditions.

Another aspect of this invention relates to a method for treating a JNK-, Src-, Lck-, or Aurora-2-mediated disease in a patient, which method comprises administering to a patient in need thereof, a therapeutically effective amount of a compound of formula I, or a pharmaceutically acceptable composition comprising said compound. According to a preferred embodiment, the invention relates to administering a compound of formula Ia, IIa, IIb, IIc, IIIa, IIIb, IIIc, IVa, IVb, IVc, Va, Vb, or Vc, or a pharmaceutically acceptable composition comprising said compound. A more preferred embodiment relates to administering a compound of formula IIa, IIb, IVa, or IVb, or a pharmaceutically acceptable composition comprising said compound.

Yet another aspect of this invention relates to a method for lessening the severity of a JNK-, Src-, Lck-, or Aurora-2-mediated disease in a patient, which method comprises administering to a patient in need thereof, a therapeutically effective amount of a compound of formula I, or a pharmaceutically acceptable composition comprising said compound. According to a preferred embodiment, the invention relates to administering a compound of formula Ia, IIa, IIb, IIc, IIIa, IIIb, IIIc, IVa, IVb, IVc, Va, Vb, or Vc, or a pharmaceutically acceptable composition comprising said compound. A more preferred embodiment relates to administering a compound of formula IIa, IIb, IVa, or IVb, or a pharmaceutically acceptable composition comprising said compound.

The activity of the compounds of this invention as kinase inhibitors may be assayed in vitro, in vivo or in a cell line. In vitro assays include assays that determine inhibition of either the kinase activity or ATPase activity of activated enzyme, for example JNK, Lck, Src or Aurora-2. Alternate in vitro assays quantitate the ability of the inhibitor to bind to JNK, Lck, Src, or Aurora-2 and may be measured either by radiolabelling the inhibitor prior to binding, isolating the inhibitor/JNK, inhibitor/Lck, or inhibitor/Src complex and determining the amount of radiolabel bound, or by running a competition experiment where new compounds are incubated with JNK, Lck, Src, or Aurora-2 bound to known radioligands. One may use any type or isoform of JNK, Lck, Src, or Aurora-2, depending upon which JNK, Lck, Src, or Aurora-2 type or isoform is to be inhibited. The details of the conditions used for the enzymatic assays are set forth in the Examples hereinbelow.

The term "JNK-mediated disease", "disorder", or "condition", as used herein means any disease, disorder or other deleterious condition in which JNK is known to play a role. Such conditions, diseases or disorders include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated or prevented by the compounds of this invention include solid tumors, ocular neovasculization, infantile haemangiomas. Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease caused by traumatic injury, acute hypoxia, ischemia or glutamate neurotoxicity.

"JNK-mediated disease", "disorder" or "condition" also includes ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, JNK inhibitors of the present invention may be capable of inhibiting the expression of inducible pro-inflammatory proteins. Therefore, other "JNK-mediated diseases", "disorder" or "conditions" which may be treated by the compounds of this invention include edema, analgesia, fever and pain such as neuromuscular pain, headache, cancer pain, dental pain and arthritis pain.

The compounds of this invention are also useful as inhibitors of Src-family kinases, especially Src. For a general review of these kinases see Thomas and Brugge, *Annu. Rev. Cell Dev. Biol.* 13:513 (1997); Lawrence and Niu, *Pharmacol. Ther.* 77:81 (1998); and Tatosyan and Mizenina, *Biochemistry* (Moscow) 65:49 (2000). Accordingly, these compounds are useful for treating Src-mediated diseases, disorders or conditions.

The term "Src-mediated disease", "disorder" or "condition" as used herein means any disease, disorder or other deleterious condition that is known to be affected by the activity of one or more Src-family kinases. Such diseases, disorders or conditions include hypercalcemia, restenosis, hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease.

The term "Lck-mediated disease", "disorder" or "condition" as used herein means any disease, disorder or other deleterious condition that is known to be affected by the activity of Lck kinase. Such diseases, disorders or conditions include autoimmune diseases, allergies, rheumatoid arthritis, and leukemia.

The term "Aurora-mediated disease", "disorder", or "condition" as used herein, means any disease or other deleterious condition or disease in which an Aurora family protein kinase is known to play a role. Such diseases or conditions include, without limitation, melanoma, leukemia, or a cancer selected from colon, breast, gastric, ovarian, cervical, melanoma, renal, prostate, lymphoma, neuroblastoma, pancreatic, leukemia and bladder.

A preferred embodiment relates to the method used to treat or prevent a JNK-mediated disease selected from inflammatory diseases, autoimmune diseases, destructive bone disorders, neurodegenerative diseases, allergies, reperfusion/ischemia in stroke, heart attacks, angiogenic disorders, organ hypoxia, vascular hyperplasia, cardiac hypertrophy, or thrombin-induced platelet aggregation.

Another preferred embodiment relates to the method used to treat or prevent a Src-mediated disease selected from hypercalcemia, osteoperosis, osteoarthritis, or sympomatic treatment of bone metastasis.

Another preferred embodiment relates to the method used to treat or prevent a Lck-mediated disease selected from autoimmune diseases, rheumatoid arthritis, or leukemia.

Another preferred embodiment relates to the method used to treat or prevent an Aurora-mediated disease selected from melanoma, leukemia, or a cancer selected from colon, breast, gastric, ovarian, cervical, melanoma, renal, prostate, lymphoma, neuroblastoma, pancreatic, leukemia and bladder Depending upon the particular protein kinase-mediated condition to be treated or prevented, additional therapeutic agents, which are normally administered to treat or prevent that condition, may be administered together with the compounds of this invention. For example, in the treatment of cancer, other chemotherapeutic or anti-proliferative agents may be combined with the compounds of this invention to treat cancer. These agents include, without limitation, adriamycin, dexamethasone, vincristine, cyclophosphamide, fluorouracil, topotecan, taxol, interferons, and platinum derivatives.

Other examples of agents the compounds of this invention may also be combined with include, without limitation, anti-diabetic agents including insulin or insulin analogues in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121, the contents of which are incorporated herein by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

Each of the aforementioned methods directed to the inhibition of JNK, Lck, Src, or Aurora-2, or the treatment of a disease alleviated thereby, is preferably carried out with a preferred compound of formula I, IIa, IIb, IVa, or IVb, as described above. More preferably, each of the aforementioned methods is carried out with a preferred compound of formula IIa, IIb, IVa, or IVb.

In order that the invention described herein may be more fully understood, the following examples are set forth. It should be understood that these examples are for illustrative purposes only and are not to be construed as limiting this invention in any manner.

EXAMPLES

As used herein, the term "$R_t$(min)" refers to the HPLC retention time, in minutes, associated with the compound using the HPLC method specified. Unless otherwise indicated, the HPLC methods utilized to obtain the reported retention times are as follows:

Method-A: Column: YMC ODS-AQ, 2×50 mm Gradient: 10%→90% $CH_3CN$/water (0.1% TFA) over 5 minutes; 90% $CH_3CN$/water (0.1% TFA) for 0.7 minutes; 90%→10% $CH_3CN$/water (0.1% TFA) over 0.1 minutes; and then 10% $CH_3CN$/water (0.1% TFA) for 1.2 minutes Flow rate: 1 mL/minute;

Method-B: Column: YMC C18, 3×150 mm Gradient: 10%→90% $CH_3CN$/water (0.1% TFA) over 7 minutes; 90% $CH_3CN$/water (0.1% TFA) for 2.0 minutes; 90%→10% $CH_3CN$/water (0.1% TFA) over 1.0 minutes; and then 10% $CH_3CN$/water (0.1% TFA) for 2.0 minutes Flow rate: 1 mL/minute.

Example 1

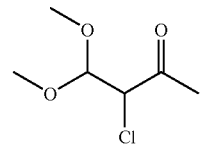

3-Chloro-4,4-dimethoxy-butan-2-one (1)

To a solution of 4-methoxy-but-3-en-2-one (9.0 g, 90.0 mmol) in 100 ml MeOH was added pyridine (14.2 g, 180 mmol). Gaseous $Cl_2$ was introduced into the above mixture under vigorous stirring at room temperature. After 5 minutes, $Cl_2$ source was removed and the reaction was cooled to room temperature. The resultant reaction mixture was concentrated to yellow oil under vacuo. and was then partitioned between $CH_2Cl_2$ and aqueous $NaHCO_3$. The aqueous layer was extracted with $CH_2Cl_2$ (150 ml×3), and the combined organic layers were dried over $Na_2SO_4$. Removal of the solvent afforded a crude material in which desired product (1) was the major product. The resulting crude material was used without further purification. $^1H$ NMR ($CDCl_3$, ppm) δ: 4.45 (d, 1H), 4.12 (d, 1H), 3.25 (s, 3H), 3.22 (s, 3H) and 2.20 (s, 3H).

Example 2

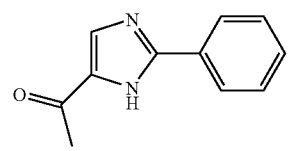

1-(2-Phenyl-3-H-imidazol-4-yl)-ethanone (2')

To a solution of 1 (2.2 g, 13.3 mmol) in 20 ml 1,4-dioxane was added benzamidine (3.24 g, 20.0 mmol) and sodium acetate (2.83 g, 33.3 mmol). The reaction was refluxed in an oil bath at 110° C. over 60 hours. After the reaction was cooled to room temperature, the salt was removed through a plug of celite and the filtrate was concentrated to a red oil. This oil was then taken up in ethyl acetate (50 ml) and extracted with 1N HCl (17 ml×3). The combined aqueous layers were basified with aqueous $Na_2CO_3$ and then were extracted with ethyl acetate (50 ml×3). The combined organic layers were dried over $Na_2SO_4$ and the solvent was removed. Purification by chromatography using $CH_2Cl_2$/MeOH (95:5/v:v) afforded 2' (1.02 g) as the desired product in 41% yield. $^1H$ NMR (acetone-$d_6$, ppm) δ: 7.4-8.1 (m, 7H) and 2.42 (s, 3H).

Example 3

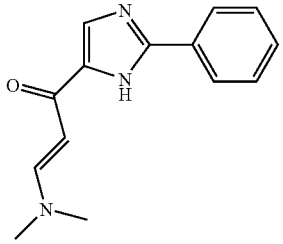

3-Dimethylamino-1-(2-phenyl-3H-imidazol-4-yl)-propenone (4')

To a solution of 2' (186 mg, 1.0 mmol) in 5 ml toluene was added dimethoxymethyldimethylamine (595 mg, 5.0 mmol). The reaction was heated in a sealed tube at 98° C. overnight. The reaction was cooled to room temperature and was then concentrated to an oil under vacuo. Purification of the crude oil by chromatography using 3% MeOH in $CH_2Cl_2$ afforded the desired product 4' in 30% yield. $^1$H NMR ($CDCl_3$, ppm) δ: 8.05 (d, 2H), 7.7 (d, 1H), 7.6 (s, 1H), 7.3 (m, 3H), 5.6 (d, 2H), 3.1 (bs, 3H) and 2.8 (bs, 3H).

Example 4

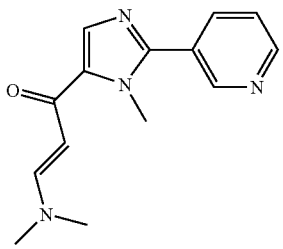

3-Dimethylamino-1-(3-methyl-2-pyridin-3-yl-3H-imidazol-4-yl)-propenone (5')

1-(2-Pyridin-3-yl-3H-imidazol-4-yl)-ethanone (2.0 g, 7.4 mmol) was added to dimethoxymethyl-dimethylamine (7.15 g, 60.0 mmol). The mixture was heated at 75° C. for 2 hours in a sealed tube. The reaction mixture was cooled to room temperature and was then concentrated to an oil under vacuo. Purification of the crude oil by chromatography using 5% MeOH in $CH_2Cl_2$ afforded desired product 5' (832 mg) in 43.9% yield. $^1$H NMR ($CD_3OD$, ppm) δ: 8.85 (s, 1H), 8.70 (d, 1H), 8.16 (d, 1H), 7.80 (s, 1H), 7.75 (d, 1H), 7.62 (dd, 1H), 5.75 (d, 1H), 3.98 (s, 3H), 3.23 (bs, 3H) and 2.96 (bs, 3H).

Example 5

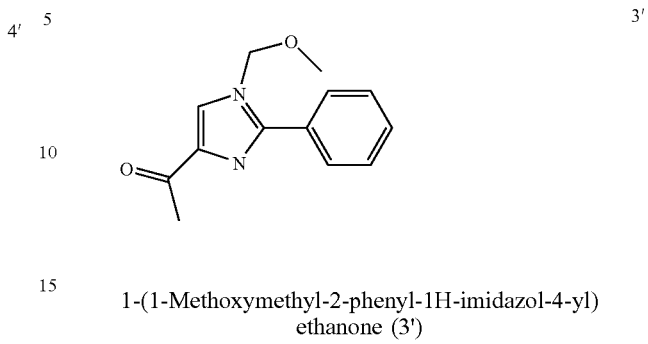

1-(1-Methoxymethyl-2-phenyl-1H-imidazol-4-yl)-ethanone (3')

To a solution of 2' (696 mg, 3.74 mmol) in 30 ml anhydrous THF was added lithium bis(trimethylsilyl)-amide (1M in THF, 3.74 ml, 3.74 mmol) at −78° C. After 10 minutes, the reaction mixture was warmed to room temperature and maintained at this temperature for 10 minutes and then was cooled to −78° C. again. MOMCl (284 uL, 3.74 mmol) was added to the reaction mixture. The reaction was allowed to warm to room temperature and stirred overnight. The reaction mixture was then poured into aqueous $NaHCO_3$ and extracted with ethyl acetate (50 ml×3). The combined organic layers were dried over anhydrous $Na_2SO_4$. The solvent was removed and the crude material was purified by chromatography using 2% MeOH in $CH_2Cl_2$ to afford 630 mg of 3' as the desired product in 73.6% yield. $^1$H NMR ($CDCl_3$, ppm) δ: 7.88 (s, 1H), 7.75 (m, 2H), 7.45 (m, 3H), 5.25 (s, 2H), 3.38 (s, 3H) and 2.55 (s, 3H).

Example 6

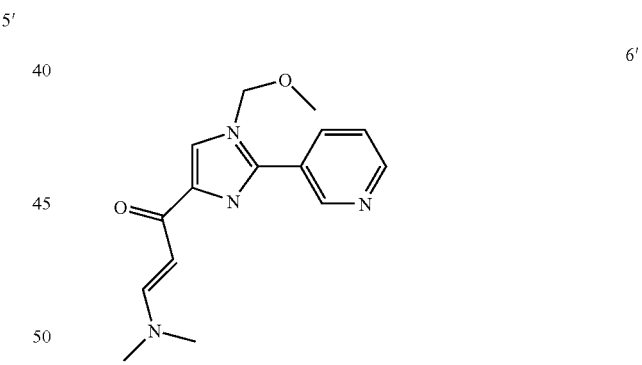

3-Dimethylamino-1-(1-methoxymethyl-2-phenyl-1H-imidazol-4-yl)-propenone (6')

To a solution of 3' (630 mg, 2.73 mmol) in 5 ml $CH_3CN$ was added dimethoxymethyldimethyl-amine (586 mg, 4.93 mmol) and dimethylamine in THF (0.5 M, 1.4 ml, 0.7 mmol). The reaction was refluxed in a sealed tube for 48 hours. The reaction was cooled to room temperature and the solvent was removed in vacuo. The crude material was purified by chromatography using 2% MeOH in $CH_2Cl_2$ to afford 397 mg of 6' as the desired product in 51.2% yield. $^1$H NMR ($CDCl_3$, ppm) δ: 7.90 (d, 1H), 7.80 (m, 3H), 7.40 (m, 3H), 6.12 (d, 1H), 5.22 (d, 2H), 3.36 (s, 3H), 3.20 (bs, 3H) and 2.92 (bs, 3H).

Example 7

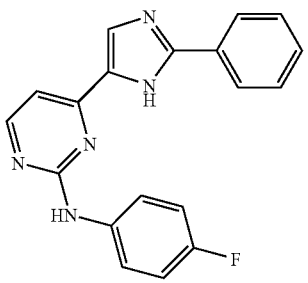

(4-Fluoro-phenyl)-[4-(2-phenyl-3H-imidazol-4-yl)pyrimidin-2-yl]-amine (IIa-2)

To a solution of 4' (50.0 mg, 0.21 mmol) in 4 ml anhydrous MeOH was added N-(4-fluoro-phenyl)-guanidine (36.8 mg, 0.24 mmol) and MeONa in MeOH (0.5M, 0.2 ml, 0.1 mmol). The reaction was refluxed in a sealed tube overnight. The crude material was subjected to preparative HPLC to afford the desired product IIa-2 in 56% yield. $^1$H NMR (MeOH-$d_4$, ppm) δ: 8.50 (d, 1H), 8.30 (s, 1H), 8.02 (d, 2H), 7.70 (m, 5H), 7.32 (d, 1H) and 7.12 (m, 2H); MS (M+1): 332.2; and HPLC (method B) Rt: 6.27 minutes.

Example 8

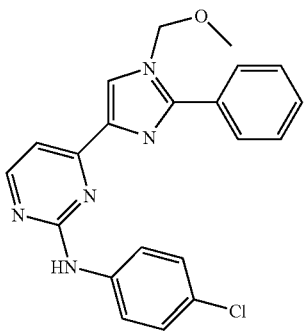

(4-Chloro-phenyl)-[4-(1-methoxymethyl-2-phenyl-1H-imidazol-4-yl)-pyrimidin-2-yl]-amine (IIa-10)

Compound IIa-10 was prepared in the same way as compound IIa-2 in 52% yield. $^1$H NMR (CDCl$_3$, ppm) δ: 8.45 (d, 1H), 7.84 (s, 1H), 7.80 (d, 2H), 7.62 (d, 2H), 7.48 (m, 4H), 7.20 (m, 3H), 5.28 (s, 2H) and 3.42 (s, 3H); MS (M+1): 392; and HPLC (method B) Rt: 6.77 minutes.

Example 9

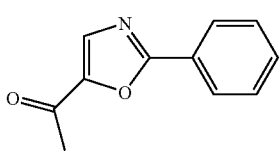

1-(2-phenyl-oxazol-5-yl)-ethanone (9')

To a solution of 1 (3.32 g, 20.0 mmol) in 10 ml acetic acid was added benzamide (3.63 g, 30.0 mmol). The reaction was heated in a sealed tube at 120° C. overnight. The reaction mixture was cooled to room temperature and poured into 100 ml water. The aqueous layer was extracted with CH$_2$Cl$_2$ (100 ml×3) and the combined organic layers were dried over Na$_2$SO$_4$. The solvent was then removed in vacuo. and the crude material was purified by chromatography using hexane:ethyl acetate (3:1/v:v) to afford 1.2 g of 9' as the desired product in 32% yield. $^1$H NMR (CDCl$_3$, ppm) δ: 8.22 (d, 2H), 7.82 (s, 1H), 7.50 (m, 3H) and 2.60 (s, 3H).

Example 10

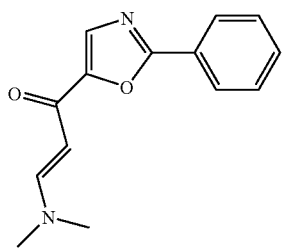

3-Dimethylamino-1-(2-phenyl-oxazol-5-yl)-propenone (10')

To a solution of 9' (800 mg, 4.27 mmol) in 5 ml CH$_3$CN was added dimethoxymethyldimethylamine (916 mg, 7.70 mmol) and dimethylamine in THF (0.5M, 4.28 ml, 2.14 mmol). The reaction was refluxed in a sealed tube for over 2 days. After the reaction was cooled to room temperature, the solvent was removed in vacuo. The crude material was purified by chromatography using 3% MeOH in CH$_2$Cl$_2$ to afford 700 mg of 10' as the desired product in 67.7% yield. $^1$H NMR (CDCl$_3$, ppm) δ: 8.15 (d, 2H), 7.80 (d, 1H), 7.70 (s, 1H), 7.45 (m, 3H), 5.60 (d, 1H), 3.24 (bs, 3H) and 2.96 (bs, 3H).

Example 11

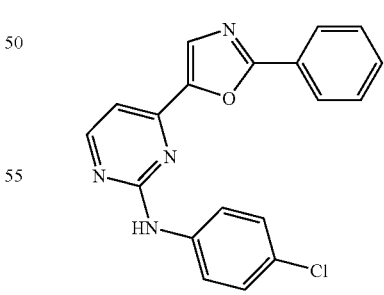

(4-Chloro-phenyl)-[4-(2-phenyl-oxazol-5-yl)-pyrimidin-2yl]-amine (IIb-1)

Compound IIb-1 was prepared in the same manner as compound IIa-2 in 62% yield. $^1$H NMR (CDCl$_3$, ppm) δ:

8.45 (d, 1H), 8.16 (d, 1H), 7.80 (s, 1H), 7.62 (d, 2H), 7.48 (m, 3H), 7.30 (d, 3H), 7.16 (s, 1H) and 7.12 (d, 1H); MS (M+1): 349; and HPLC (method B) Rt: 8.44 minutes.

Example 12

Other compounds of formula IIa were prepared by methods substantially similar to those described in the above Examples 7 and 8 and those illustrated in Scheme I. The characterization data for these compounds is summarized in Table 6 below. "Y" designates $^1$H NMR data was obtained and found to be consistent with the assigned structure. Compound numbers in Table 7 correspond to the compound numbers listed in Table 1.

TABLE 7

Characterization Data for Selected Compounds of Formula IIa

| Compound No. | MS (M + 1, obs) | Rt (min.) | Method | $^1$H NMR |
|---|---|---|---|---|
| IIa-1 | 348.1 | 2.92 | A | Y |
| IIa-2 | 332.2 | 6.27 | B | Y |
| IIa-3 | 344.2 | 6.35 | B | Y |
| IIa-4 | 374 | 6.50 | B | Y |
| IIa-5 | 363.2 | 6.35 | B | Y |
| IIa-6 | 347.2 | 5.74 | B | Y |
| IIa-7 | 329.2 | 5.57 | B | Y |
| IIa-8 | 435.2 | 6.93 | B | Y |
| IIa-9 | 364.2 | 5.69 | B | Y |
| IIa-10 | 392 | 6.77 | B | Y |
| IIa-11 | 376.1 | 6.50 | B | Y |
| IIa-12 | 358.1 | 6.60 | B | Y |
| IIa-13 | 403 | 7.01 | B | Y |
| IIa-14 | 388.2 | 3.10 | A | Y |
| IIa-15 | 418.3 | 3.22 | A | Y |
| IIa-16 | 436.1 | 3.78 | A | Y |
| IIa-17 | 464.3 | 3.98 | A | Y |
| IIa-18 | 359.2 | 2.02 | A | Y |
| IIa-19 | 389.2 | 2.15 | A | Y |
| IIa-20 | 407.1 | 2.51 | A | Y |
| IIa-21 | 374.2 | 2.35 | A | Y |
| IIa-22 | 387.2 | 2.13 | A | Y |
| IIa-23 | 430.1 | 7.01 | B | Y |
| IIa-24 | 414.1 | 6.63 | B | Y |
| IIa-25 | 426.1 | 6.61 | B | Y |
| IIa-26 | 456.2 | 6.74 | B | Y |
| IIa-27 | 474 | 7.11 | B | Y |
| IIa-28 | 396.1 | 6.51 | B | Y |
| IIa-29 | 502.2 | 7.42 | B | Y |
| IIa-30 | 441.1 | 6.84 | B | Y |
| IIa-31 | 454.1 | 6.76 | B | Y |
| IIa-32 | 431 | 6.48 | B | — |
| IIa-33 | 402.2 | 6.22 | B | Y |

Example 13

Other compounds of formula IIb were prepared by methods substantially similar to those described in the above Example 11 and those illustrated in Scheme II. The characterization data for these compounds is summarized in Table 8 below. "Y" designates $^1$H NMR data was obtained and found to be consistent with the assigned structure. Compound numbers in Table 8 correspond to the compound numbers listed in Table 2.

TABLE 8

Characterization Data for Selected Compounds of Formula IIb

| Compound No. | MS (M + 1, obs) | Rt (min.) | Method | $^1$H NMR |
|---|---|---|---|---|
| IIb-1 | 349 | 8.44 | B | Y |
| IIb-2 | 333 | 7.88 | B | Y |
| IIb-3 | 345 | 7.88 | B | Y |
| IIb-4 | 375.1 | 7.98 | B | Y |
| IIb-5 | 315 | 7.77 | B | Y |
| IIb-6 | 421.2 | 8.68 | B | Y |
| IIb-7 | 360.1 | 8.35 | B | Y |
| IIb-8 | 392.9 | 7.22 | B | Y |
| IIb-9 | 373.1 | 4.71 | B | Y |
| IIb-10 | 321.1 | 5.51 | B | Y |
| IIb-11 | 455.1 | 8.89 | B | Y |
| IIb-12 | 466.2 | 8.82 | B | Y |
| IIb-13 | 435.2 | 7.40 | B | Y |
| IIb-14 | 427.2 | 7.54 | B | Y |
| IIb-15 | 451.2 | 8.43 | B | Y |
| IIb-16 | 481.2 | 8.40 | B | Y |
| IIb-17 | 355.2 | 4.27 | A | Y |

The following examples demonstrate how the compounds of this invention may be tested as inhibitors of c-Jun-N-terminal, Src, and Lck kinases.

Example 14

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites. The protein was expressed in *E. coli*. Due to the poor solubility of the expressed full-length protein (Met 1-Gln 422), an N-terminally truncated protein starting at Ser residue at position 40 (Ser 40) was produced. This truncation corresponds to Ser 2 of JNK1 and JNK2 proteins, and is preceded by a methionine (initiation) and a glycine residue. The glycine residue was added in order to introduce an NcoI site for cloning into the expression vector. In addition, systematic C-terminal truncations were performed by PCR to identify a construct that give rise to diffraction-quality crystals. One such construct encodes amino acid residues Ser40-Glu402 of JNK3α1 and is preceded by Met and Gly residues.

The construct was prepared by PCR using deoxyoligonucleotides:

5' GCTCTAGAGCTCC ATGGGCAGCAAAAGCAAAGTTGACAA 3' (forward primer with initiation codon underlined)(SEQ ID NO:1) and 5' TAGCGGATCC TCATTCTGAATTCATTACTTCCTTGTA 3' (reverse primer with stop codon underlined)(SEQ ID NO:2) as primers and was confirmed by DNA sequencing. Control experiments indicated that the truncated JNK3 protein had an equivalent kinase activity towards myelin basic protein when activated with an upstream kinase MKK7 in vitro. *E. coli* strain BL21 (DE3) (Novagen) was transformed with the JNK3 expression construct and grown at 30° C. in LB supplemented with 100 μg/ml carbenicillin in shaker flasks until the cells were in log phase (OD$_{600}$~0.8). Isopropylthio-β-D-galactosidase (IPTG) was added to a final concentration of 0.8 mM and the cells were harvested 2 hours later by centrifugation.

E. coli cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 µg/ml Pepstatin, 1 µg/ml each of E-64 and Leupeptin). Cells were lysed on ice using a microfluidizer and centrifuged at 100,000×g for 30 min at 4° C. The 100,000×g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear gradient of 50-300 mM NaCl. JNK3 eluted between 150-200 mM NaCl.

Example 15

Activation of JNK3

Five mg of JNK3 was diluted to 0.5 mg/ml in 50 mM HEPES buffer, pH 7.5, containing 100 mM NaCl, 5 mM DTT, 20 mM MgCl2 and 1 mM ATP. GST-MKK7(DD) was added at a molar ratio of 1:2.5 GST-MKK7:JNK3. After incubation for 30 minutes at 25° C., the reaction mixture was concentrated 5-fold by ultrafiltration in a Centriprep-30 (Amicon, Beverly, Mass.), diluted to 10 ml and an additional 1 mM ATP added. This procedure was repeated three times to remove ADP and replenish ATP. The final addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphorylated JNK3 is separated from singly phosphorylated JNK. Activated JNK3 (i.e. doubly phosphorylated JNK3) was stored at −70° C. at 0.25-1 mg/ml.

Example 16

JNK Inhibition Assay

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM MgCl2, 2.5 mM phosphoenolpyruvate, 200 µM NADH, 150 µg/mL pyruvate kinase, 50 µg/mL lactate dehydrogenase, and 200 µM EGF receptor peptide. The EGF receptor peptide has the sequence KRELVEPLTPSGEAPNQALLR (SEQ ID NO: 3), and is a phosphoryl acceptor in the JNK3-catalyzed kinase reaction. The reaction was initiated by the addition of 10 µM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

Table 9 shows the results of the activity of selected compounds of this invention in the JNK inhibition assay. The compound numbers correspond to the compound numbers in Tables 1-3. Compounds having a $K_i$ less than 0.1 micromolar (µM) are rated "A", compounds having a $K_i$ between 0.1 and 1 µM are rated "B" and compounds having a $K_i$ greater than 1 µM are rated "C".

TABLE 9

JNK3 Activity of Selected Compounds

| No. | Activity | No. | Activity | No. | Activity |
|-----|----------|-----|----------|-----|----------|
| IIa-10 | C | IIa-11 | C | IIa-12 | C |
| IIa-13 | C | IIa-14 | C | IIa-15 | C |
| IIa-16 | C | IIa-17 | C | IIa-18 | B |
| IIa-19 | B | IIa-20 | B | IIa-21 | B |
| IIa-22 | B | IIa-23 | B | IIa-24 | B |
| IIa-25 | A | IIa-26 | B | IIa-27 | B |
| IIa-28 | B | IIa-29 | B | IIa-30 | B |
| IIa-31 | B | IIa-32 | B | IIa-33 | A |
| IIb-1 | C | IIb-2 | B | IIb-3 | B |
| IIb-4 | B | IIb-5 | B | IIb-6 | B |
| IIb-7 | B | IIb-17 | C | IIc-22 | A |
| IIc-23 | B | IIc-24 | C | IIc-25 | C |

Example 17

The compounds of this invention can be evaluated as inhibitors of human Src kinase using either a radioactivity-based assay or spectrophotometric assay.

Src Inhibition Assay A: Radioactivity-Based Assay

The compounds can be assayed as inhibitors of full length recombinant human Src kinase (from Upstate Biotechnology, cat. no. 14-117) expressed and purified from baculo viral cells. Src kinase activity is monitored by following the incorporation of $^{33}$P from ATP into the tyrosine of a random poly Glu-Tyr polymer substrate of composition, Glu:Tyr=4:1 (Sigma, cat. no. P-0275). The following are the final concentrations of the assay components: 0.05 M HEPES, pH 7.6, 10 mM MgCl$_2$, 2 mM DTT, 0.25 mg/ml BSA, 10 µM ATP (1-2 µCi $^{33}$P-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}$P-ATP. After 20 min of reaction, the reactions are quenched with 150 µl of 10% trichloroacetic acid (TCA) containing 20 mM Na$_3$PO$_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM Na$_3$PO$_4$ and then 4 times with methanol. 200 µl of scintillation fluid is then added to each well. The plates are sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quanitified using a coupled enzyme assay (Fox et al., Protein Sci. 7:2249(1998)]. In this assay one molecule of NADH is oxidized to NAD for every molecule of ADP produced in the kinase reaction. The disappearance of NADH can be conveniently followed at 340 nm.

The following are the final concentrations of the assay components: 0.025 M HEPES, pH 7.6, 10 mM MgCl2, 2 mM DTT, 0.25 mg/ml poly Glu-Tyr, and 25 nM of recombinant human Src kinase. Final concentrations of the components of the coupled enzyme system are 2.5 mM phosphoenol-pyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compound IIc-22 was found to have a $K_i$ of less than 0.1 µM for Src.

Example 18

The compounds of this invention can be evaluated as inhibitors of human Lck kinase using either a radioactivity-based assay or spectrophotometric assay.

Lck Inhibition Assay A: Radioactivity-based Assay

The compounds are assayed as inhibitors of full length bovine thymus Lck kinase (from Upstate Biotechnology, cat. no. 14-106) expressed and purified from baculo viral cells. Lck kinase activity is monitored by following the incorporation of $^{33}P$ from ATP into the tyrosine of a random poly Glu-Tyr polymer substrate of composition, Glu:Tyr=4:1 (Sigma, cat. no. P-0275). The following are the final concentrations of the assay components: 0.025 M HEPES, pH 7.6, 10 mM MgCl$_2$, 2 mM DTT, 0.25 mg/ml BSA, 10 µM ATP (1-2 µCi $^{33}$P-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}$P-ATP. After 20 min of reaction, the reactions are quenched with 150 µl of 10% trichloroacetic acid (TCA) containing 20 mM Na$_3$PO$_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM Na$_3$PO$_4$ and then 4 times with methanol. 200 µl of scintillation fluid is then added to each well. The plates are sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Lck Inhibition Assay B: Spectrophotometric Assay

The ADP produced from ATP by the human recombinant Lck kinase-catalyzed phosphorylation of poly Glu-Tyr substrate is quanitified using a coupled enzyme assay [Fox et al., Protein Sci., 7:2249(1998)]. In this assay one molecule of NADH is oxidized to NAD for every molecule of ADP produced in the kinase reaction. The disappearance of NADH can be conveniently followed at 340 nm.

The following are the final concentrations of the assay components: 0.025M HEPES, pH 7.6, 10 mM MgCl$_2$, 2 mM DTT, 5 mg/ml poly Glu-Tyr, and 50 nM of recombinant human Lck kinase. Final concentrations of the components of the coupled enzyme system are 2.5 mM phosphoenol pyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 150 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compound IIc-22 was found to have a $K_i$ of less than 0.1 µM for Lck. Compounds IIa-25 and IIa-31 were found to have a $K_i$ between 0.1 and 1.0 µM for Lck.

Example 19

Inhibition of Aurora Assay

Compounds are screened in the following manner for their ability to inhibit Aurora using a standard coupled enzyme assay (Fox et al (1998) Protein Sci 7, 2249). To an assay stock buffer solution containing 0.1M HEPES 7.5, 10 mM MgCl2, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 µM peptide (LRRASLG, American Peptide, Sunnyvale, Calif.) is added a DMSO solution of a compound of the present invention to a final concentration of 30 µM. The resulting mixture is incubated at 30° C. for 10 minutes. The reaction is initiated by the addition of 10 µL of Aurora stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

The following compounds were shown to have $K_i$ values less than 0.1 µM for Aurora-2: IIa-24, IIa-25, IIa-26, and IIa-31. The following compounds were shown to have $K_i$ values between 0.1 and 1.0 µM for Aurora-2: IIa-28, IIa-30, IIa-32, and IIc-23. The following compounds were shown to have $K_i$ values greater than 1.0 µM for Aurora-2: IIc-22, IIc-24, IIc-25, IIc-28, IIc-29, IIc-30, IIc-31, IIc-32, IIc-33, IIc-34, IIc-35, IIc-36, IIc-36, IIc-37, IIc-38, IIc-39, and IIc-42.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A compound of formula I:

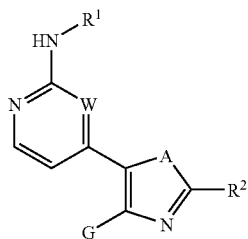

or a pharmaceutically acceptable salt thereof, wherein:
W is nitrogen;
G is hydrogen or $C_{1-3}$ aliphatic
A is $-N-T_{(n)}-R$;
$R^1$ is $-T_{(n)}-Ar^1$;
each n is independently 0 or 1;
T is a $C_{1-4}$ alkylidene chain wherein one methylene unit of T is optionally replaced by —C(O)—, —C(O)O—, —C(O)NH—, —SO$_2$—, or —SO$_2$NH—;
$Ar^1$ is a 3-7 membered monocyclic saturated, partially saturated or aromatic ring having 0-3 heteroatoms independently selected from nitrogen, oxygen, or sulfur, or a 8-10 membered bicyclic saturated, partially saturated or aromatic ring having 0-5 heteroatoms independently selected from nitrogen, oxygen, or sulfur, wherein each member of $Ar^1$ is optionally substituted with one -Z-$R^3$ and one to three additional groups independently selected from —R, halogen, oxo, —NO$_2$, —CN, —OR, —SR, —N(R)$_2$, —NRC(O)R, —NRC(O)N(R)$_2$, —NRCO$_2$R, —C(O)R, —CO$_2$R, —OC(O)R, —C(O)N(R)$_2$, —OC(O)N(R)$_2$, —S(O)R, —SO$_2$R, —SO$_2$N(R)$_2$, —NRSO$_2$R, —NRSO$_2$N(R)$_2$, —C(O)C(O)R, or —C(O)CH$_2$C(O)R;

each R is independently selected from hydrogen or a $C_{1-6}$ aliphatic, wherein said aliphatic is optionally substituted with one to three groups independently selected from oxo, —CO$_2$R', —OR', —N(R')$_2$, —SR', —NO$_2$, —NR'C(O)R', —NR'C(O)N(R')$_2$, —NR'CO$_2$R', —C(O)R', —OC(O)R', —C(O)N(R')$_2$, —OC(O)N(R')$_2$, —S(O)R', —SO$_2$R', —SO$_2$N(R')$_2$, —NR'SO$_2$R', —NR'SO$_2$N(R')$_2$, —C(O)C(O)R', —C(O)CH$_2$C(O)R', halogen, or —CN, or two R bound to the same nitrogen atom are taken together with that nitrogen atom to form a five or six membered heterocyclic or heteroaryl ring having one to two additional heteroatoms independently selected from oxygen, nitrogen, or sulfur;

each R' is independently selected from hydrogen or $C_{1-6}$ aliphatic, wherein said aliphatic is optionally substituted with one to three groups independently selected from oxo, —CO₂H, —OH, —NH₂, —SH, —NO₂, —NHC(O)H, —NHC(O)NH₂, —NHCO₂H, —C(O)H, —OC(O)H, —C(O)NH₂, —OC(O)NH₂, —S(O)H, —SO₂H, —SO₂NH₂, —NHSO₂H, —NHSO₂NH₂, —C(O)C(O)H, —C(O)CH₂C(O)H, halogen, or —CN, or two R' bound to the same nitrogen atom are taken together with that nitrogen atom to form a five or six membered heterocyclic or heteroaryl ring optionally having one or two additional heteroatoms independently selected from nitrogen, oxygen, or sulfur;

Z is a $C_1$-$C_6$ alkylidene chain wherein up to two non-adjacent methylene units of Z are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO₂—, —N(R)SO₂—, —SO₂N(R)—, —N(R)SO₂N(R)—, —O—, —S—, or —N(R)—;

$R^2$ is -$Q_{(n)}$—$Ar^2$;

$Ar^2$ is selected from a 3-7 membered monocyclic saturated, partially saturated or aromatic ring having 0-3 heteroatoms independently selected from nitrogen, oxygen, or sulfur, or a 8-10 membered bicyclic saturated, partially saturated or aromatic ring having 0-5 heteroatoms independently selected from nitrogen, oxygen, or sulfur, wherein each member of $Ar^2$ is optionally substituted with 1-5 groups independently selected from -Z-$R^3$, —R, halogen, oxo, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —S(O)R, —SO₂R, SO₂N(R)₂, —N(R)SO₂R, —N(R)SO₂N(R)₂, —C(O)C(O)R, or —C(O)CH₂C(O)R;

Q is a $C_{1-3}$ alkylidene chain;

$R^3$ is selected from —$Ar^3$, —R, halogen, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —SOR, —SO₂R, —SO₂N(R)₂, —NRSO₂R, —NRSO₂N(R)₂, —C(O)C(O)R, or —C(O)CH₂C(O)R; and $Ar^3$ is a 5-6 membered saturated, partially saturated, or aromatic ring having 0-3 heteroatoms independently selected from nitrogen, oxygen, or sulfur, wherein each member of $Ar^3$ is optionally substituted with halogen, oxo, —CN, —NO₂, —R', —OR', —N(R')₂, —N(R')C(O)R', —N(R')C(O)N(R')₂, —N(R')CO₂R', —C(O)R', —CO₂R', —OC(O)R', —C(O)N(R')₂, —OC(O)N(R')₂, or —SO₂R';

provided that when:

$R^2$ is a saturated ring, then $R^1$ is other than an optionally substituted phenyl.

2. The compound according to claim 1, wherein said compound has one or more features selected from the group consisting of:

(a) $R^1$ is hydrogen, $Ar^1$ or -T-$Ar^1$ wherein T is a $C_{1-4}$ alkylidene chain and $Ar^1$ is a 6-membered saturated, partially saturated, or aryl ring having zero to two heteroatoms independently selected from nitrogen, oxygen, or sulfur, and wherein each member of $R^1$ is optionally substituted with one -Z-$R^3$ and one to three additional groups independently selected from —CO₂R, —OR, halogen, —NRSO₂R, —SO₂N(R)₂, —NRCON(R)₂, —NO₂, or —N(R)₂;

(b) $R^2$ is $Ar^2$ or —CH₂—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted with one to five groups independently selected from -Z-$R^3$, —R, halogen, —NO₂, —CN, —OR, —SR, —N(R)₂, —NRC(O)R, —NRC(O)N(R)₂, —NRCO₂R, —C(O)R, —CO₂R, —C(O)N(R)₂, —OC(O)N(R)₂, —S(O)R, —SO₂R, —SO₂N(R)₂, —N(R)SO₂R, —N(R)SO₂N(R)₂, —C(O)C(O)R, or —C(O)CH₂C(O)R; and (c) G is hydrogen.

3. The compound according to claim 2, wherein said compound has one or more features selected from the group consisting of:

(a) $R^1$ is selected from a phenyl, benzyl, pyridyl, piperidinyl, or cyclohexyl ring, wherein said ring is optionally substituted with benzyloxy, phenoxy, —SO₂NH₂, —OH, —NO₂, —NH₂, —OMe, —Br, —Cl, —CO₂Me, —NHSO₂Me, —NHSO₂Et, —NHCON(Me)₂, —NHCON(Et)₂, —NHCOpyrrolidin-1-yl, —NHCOmorpholin-4-yl, —O—CH₂-phenyl, —O(CH₂)₃OH, —O(CH₂)₃NH(CH₂)₂OH, —O(CH₂)₂NH(CH₂)₂OH, —O(CH₂)₃N(hydroxyethyl)(methyl), —O(CH₂)₃pyrrolidin-1-yl, —O(CH₂)₂morpholin-4-yl, —O(CH₂)₃N(Me)₂, —O(CH₂)₃N(Et)₂, —O(CH₂)₃(4-hydroxyethyl piperazin-1-yl), —O(CH₂)₃piperazin-1-yl, —O(CH₂)₃(4-hydroxymethylpiperidin-1-yl), —O(CH₂)₃(4-hydroxypiperidin-1-yl), —NHCO(CH₂)₃N(Me)₂, —NHCO(CH₂)₃NCOCH₃, —NHCOCH₂pyridin-2-yl, —NHCOCH₂(2-aminothiazol-4-yl), —NHCOCH₂cyclopropyl, —NHCO(CH₂)₂N(Et)₂, —NHCO(CH₂)2-(piperazin-2,5-dione-3-yl), —NHCO₂CH₂tetrahydrofuran-2-yl, —NHCO₂tetrahydrofuran-2-yl, —NHCO₂tetrahydropyran-4-yl, or —NHCO₂CH₂tetrahydropyran-2-yl;

(b) $R^2$ is selected from phenyl, pyridyl, pyrimidinyl, cyclohexyl, piperidinyl, furanyl, or benzyl, wherein $R^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —NH₂, methyl, methoxy, or ethoxy; and (c) G is hydrogen.

4. The compound according to claim 1, wherein said compound has the formula IVa:

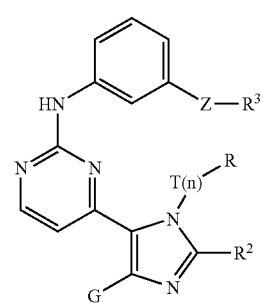

IVa or a pharmaceutically acceptable derivative thereof.

5. The compound according to claim 4, wherein said compound has one or more features selected from the group consisting of:

(a) $R^2$ is $Ar^2$ or —$CH_2$—$Ar^2$ wherein $Ar^2$ is selected from 5-6 membered ring selected from carbocyclic, aryl, or a heterocyclyl or heteroaryl ring having one to two heteroatoms independently selected from nitrogen, oxygen or sulfur, and wherein $Ar^2$ is optionally substituted by wherein $Ar^2$ is optionally substituted with one to five groups independently selected from -Z-$R^3$, —R, halogen, —$NO_2$, —CN, —OR, —SR, —N(R)$_2$, —NRC(O)R, —NRC(O)N(R)$_2$, —NRCO$_2$R, —C(O)R, —CO$_2$R, —C(O)N(R)$_2$, —OC(O)N(R)$_2$, —S(O)R, —SO$_2$R, —SO$_2$N(R)$_2$, —N(R)SO$_2$R, —N(R)SO$_2$N(R)$_2$, —C(O)C(O)R, or —C(O)CH$_2$C(O)R;

(b) G is hydrogen;

(c) Z is a $C_{1-4}$ alkylidene chain wherein one methylene unit of Z is optionally replaced by —O—, —NH—, —NHC(O)—, —NHC(O)O—, —NHSO$_2$—, —C(O)NH—; and (d) $R^3$ is selected from —N(R)$_2$, —NHC(O)R, or $Ar^3$ wherein $Ar^3$ is a 5-6 membered heterocyclic or heteroaryl ring having one to two heteroatoms independently selected from nitrogen, oxygen, or sulfur and $Ar^3$ is optionally substituted with —R', —OR', —N(R')$_2$, or oxo.

6. The compound according to claim 5, wherein said compound has one or more features selected from the group consisting of:

(a) $R^2$ is selected from phenyl, pyridyl, pyrimidinyl, cyclohexyl, piperidinyl, furanyl, or benzyl, wherein each member of $R^2$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, —OH, —NH$_2$, methyl, methoxy, or ethoxy;

(b) G is hydrogen; and (c) -Z-$R^3$ is selected from —O—CH$_2$-phenyl, —O(CH$_2$)$_3$OH, —O(CH$_2$)$_3$NH(CH$_2$)$_2$OH, —O(CH$_2$)$_2$NH(CH$_2$)$_2$OH, —O(CH$_2$)$_3$N(hydroxyethyl)(methyl), —O(CH$_2$)$_3$pyrrolidin-1-yl, —O(CH$_2$)$_2$morpholin-4-yl, —O(CH$_2$)$_3$ N(Me)$_2$, —O(CH$_2$)$_3$N(Et)$_2$, —O(CH$_2$)$_3$(4-hydroxyethyl piperazin-1-yl), —O(CH$_2$)$_3$piperazin-1-yl, —O(CH$_2$)$_3$(4-hydroxymethylpiperidin-1-yl), —O(CH$_2$)$_3$(4-hydroxypiperidin-1-yl), —NHCO(CH$_2$)$_3$ N(Me)$_2$, —NHCO(CH$_2$)$_3$NCOCH$_3$, —NHCOCH$_2$pyridin-2-yl, —NHCOCH$_2$(2-aminothiazol-4-yl), —NHCOCH$_2$cyclopropyl, —NHCO(CH$_2$)$_2$N(Et)$_2$, —NHCO(CH$_2$)$_2$-(piperazin-2,5-dione-3-yl), —NHC(O)pyrrolidin-1-yl, —NHCOmorpholin-4-yl, —NHCO$_2$CH$_2$tetrahydrofuran-2-yl, —NHCO$_2$tetrahydrofuran-2-yl, —NHCO$_2$tetrahydropyran-4-yl, or —NHCO$_2$CH$_2$tetrahydropyran-2-yl.

7. The compound according to claim 1 selected from one of the following compounds of formula IIa:

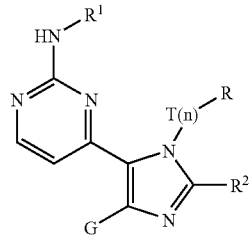

IIa

| No. IIa- | G | —T$_{(n)}$—R | $R^1$ | $R^2$ |
|---|---|---|---|---|
| 1 | H | H | 4-Cl-phenyl | Ph |
| 2 | H | H | 4-F-phenyl | Ph |
| 3 | H | H | 3-OMe-Ph | Ph |
| 4 | H | H | 3,5-(OMe)$_2$-Ph | Ph |
| 5 | H | CH$_3$ | 4-Cl-phenyl | pyridin-3-yl |
| 6 | H | CH$_3$ | 4-F-phenyl | pyridin-3-yl |
| 7 | H | CH$_3$ | Ph | pyridin-3-yl |
| 8 | H | CH$_3$ | 3-BnO-Ph | pyridin-3-yl |
| 9 | H | CH$_3$ | 6-Cl-pyridin-3-yl | pyridin-3-yl |
| 10 | H | CH$_2$OCH$_3$ | 4-Cl-phenyl | Ph |
| 11 | H | CH$_2$OCH$_3$ | 4-F-phenyl | Ph |
| 12 | H | CH$_2$OCH$_3$ | Ph | Ph |
| 13 | H | CH$_2$OCH$_3$ | 4-NO$_2$-Ph | Ph |
| 14 | H | CH$_2$OCH$_3$ | 3-OMe-Ph | Ph |
| 15 | H | CH$_2$OCH$_3$ | 3,5-(OMe)$_2$-Ph | Ph |
| 16 | H | CH$_2$OCH$_3$ | 3-Br-Ph | Ph |
| 17 | H | CH$_2$OCH$_3$ | 3-BnO-Ph | Ph |
| 18 | H | CH$_3$ | 3-OMe-Ph | pyridin-3-yl |
| 19 | H | CH$_3$ | 3,5-(OMe)$_2$-Ph | pyridin-3-yl |
| 20 | H | CH$_3$ | 3-Br-Ph | pyridin-3-yl |
| 21 | H | CH$_3$ | 4-NO$_2$-Ph | pyridin-3-yl |
| 22 | H | CH$_3$ | 3-CO$_2$CH$_3$-Ph | pyridin-3-yl |
| 23 | H | H | 4-Cl-Ph | —CH$_2$-(2,6-di-Cl)-Ph |
| 24 | H | H | 4-F-Ph | —CH$_2$-(2,6-di-Cl)-Ph |
| 25 | H | H | 3-OMe-Ph | —CH$_2$-(2,6-di-Cl)-Ph |
| 26 | H | H | 3,5-(OMe)$_2$-Ph | —CH$_2$-(2,6-di-Cl)-Ph |
| 27 | H | H | 3-Br-Ph | —CH$_2$-(2,6-di-Cl)-Ph |
| 28 | H | H | Ph | —CH$_2$-(2,6-di-Cl)-Ph |
| 29 | H | H | 3-BnO-Ph | —CH$_2$-(2,6-di-Cl)-Ph |
| 30 | H | H | 4-NO$_2$-Ph | —CH$_2$-(2,6-di-Cl)-Ph |
| 31 | H | H | 3-CO$_2$CH$_3$-Ph | —CH$_2$-(2,6-di-Cl)-Ph |
| 32 | H | H | 6-Cl-pyridin-3-yl | —CH$_2$-(2,6-di-Cl)-Ph |
| 33 | H | H | cyclohexyl | —CH$_2$-(2,6-di-Cl)-Ph |
| 34 | H | CH$_2$OCH$_3$ | 3-Cl-Ph | Ph |
| 35 | H | CH$_3$ | 3-Cl-Ph | pyridin-3-yl |
| 42 | H | H | Ph | 4-Cl-phenyl |
| 43 | H | H | Ph | 4-CF$_3$-phenyl |
| 44 | H | H | Ph | 4-CH$_3$-phenyl |
| 45 | H | H | CH$_2$Ph | pyridin-3-yl |
| 46 | H | H | COPh | 4-Cl-phenyl |
| 47 | H | H | COPh | 4-CF$_3$-phenyl |
| 48 | H | H | COPh | 4-CH$_3$-phenyl |
| 49 | H | H | CONHCH$_2$Ph | 4-Cl-phenyl |
| 50 | H | H | CONHCH$_2$Ph | 4-CF$_3$-phenyl |
| 51 | H | H | CONHCH$_2$Ph | 4-CH$_3$-phenyl |
| 53 | H | H | Ph | thiazol-2-yl |
| 54 | H | H | cyclohexyl | piperidin-1-yl |
| 55 | H | H | cyclohexyl | 4-CONHMe-phenyl |
| 56 | H | H | Ph | Ph |
| 57 | H | H | CH$_2$Ph | CH$_2$Ph |
| 60 | H | H | 3-OBn-Ph | Ph |
| 61 | H | H | 3-SO$_2$NH$_2$-Ph | Ph |
| 62 | H | H | 3-OH-Ph | Ph |
| 63 | H | H | 4-OBn-Ph | Ph |
| 64 | H | H | 3-NO$_2$-Ph | 3-OMe-Ph |
| 65 | H | H | 3-NH$_2$-Ph | 3-OMe-Ph |
| 66 | H | H | 3-NO$_2$-Ph | 3-OH-Ph |
| 67 | H | H | Ph | 3-OBn-Ph |
| 68 | H | H | 3-NO$_2$-Ph | 3-OBn-Ph |
| 69 | H | H | 3-NO$_2$-Ph | 3-OBn-Ph |

-continued

Formula IIa: 2-(R¹-amino)pyrimidine linked to imidazole bearing T(n)-R, R², and G substituents.

| No. IIa- | G | —T(n)—R | R¹ | R² |
|---|---|---|---|---|
| 70 | H | H | 3-OBn-Ph | 3-pyridyl |
| 71 | H | H | 3-OH-Ph | 3-pyridyl |
| 72 | H | H | 3-NH₂-Ph | 3-Br-Ph |
| 73 | H | H | 3-NH₂-Ph | 3-OPh-Ph |
| 74 | H | H | 3-OBn-Ph | 5-Br-3-pyridyl |
| 75 | H | H | Ph | 3-OPh-Ph |
| 76 | H | H | 3-OH-Ph | 3-OBn-Ph |
| 77 | H | H | 3-OH-Ph | 3-OPh-Ph |
| 78 | H | H | 3-OH-Ph | 3-OH-Ph |
| 79 | H | H | 3-OH-Ph | 3-Br-Ph |
| 80 | H | H | 3-OBn-Ph | 3-Br-Ph |
| 81 | H | H | 3-OH-Ph | 3-(3-OH-Ph)-Ph |
| 82 | H | H | 3-OH-Ph | 3-(3-OEt-Ph)-Ph |
| 83 | H | H | 3-OH-Ph | 3-(3-pyridyl)-Ph |
| 84 | H | H | 3-OBn-Ph | 5-Ph-pyridin-3-yl |
| 85 | H | H | 3-OBn-Ph | 5-Br-3-pyridyl |
| 86 | H | H | 3-OBn-Ph | 5-Ph-3-pyridyl |
| 87 | H | H | 4-OH-Ph | Ph |
| 88 | H | H | 3-OH-Ph | 5-Ph-pyridin-3-yl |
| 89 | H | H | 3-OH-Ph | 3-(3-NH₂-Ph)-Ph |
| 90 | H | H | 3-OH-Ph | 3-(3-Cl,4-F-Ph)-Ph |
| 91 | H | H | 3-OH-Ph | 3-(4-iPr-Ph)-Ph |
| 92 | H | H | 3-NO₂-Ph | 5-Ph-pyridin-3-yl |
| 93 | H | H | 3-OH-Ph | 3-(3-N-Boc-pyrrol-2-yl)-Ph |
| 94 | H | H | 3-NHSO₂Me-Ph | 3-pyridyl |
| 95 | H | H | 3-NHSO₂Et-Ph | 3-pyridyl |
| 96 | H | H | 3-SO₂NH₂-Ph | 3-pyridyl |
| 97 | H | H | 3-OH-Ph | 3-(2-OH-Ph)-Ph |
| 98 | H | H | 3-OH-Ph | 3-(3-pyrrol-2-yl)-Ph |
| 99 | H | H | 3-OH-Ph | 3-(6-OMe-pyridin-2-yl)-Ph |
| 100 | H | H | 3-OH-Ph | 3-(5-OMe-pyridin-2-yl)-Ph |
| 101 | H | H | 3-OH-Ph | 3-(2,5-Me₂-isoxazol-4-yl)-Ph |
| 102 | H | H | 3-OH-Ph | 3-(pyridin-4-yl)-Ph |
| 109 | H | CH₃ | Ph | 4-Cl-phenyl |
| 110 | H | CH₃ | Ph | 4-CF₃-phenyl |
| 111 | H | CH₃ | Ph | 4-CH₃-phenyl |
| 112 | H | CH₃ | CH₂Ph | pyridin-3-yl |
| 113 | H | CH₃ | COPh | 4-Cl-phenyl |
| 114 | H | CH₃ | COPh | 4-CF₃-phenyl |
| 115 | H | CH₃ | COPh | 4-CH₃-phenyl |
| 116 | H | CH₃ | CONHCH₂Ph | 4-Cl-phenyl |
| 117 | H | CH₃ | CONHCH₂Ph | 4-CF₃-phenyl |
| 118 | H | CH₃ | CONHCH₂Ph | 4-CH₃-phenyl |
| 120 | H | CH₃ | Ph | thiazol-2-yl |
| 121 | H | CH₃ | cyclohexyl | piperidin-1-yl |
| 122 | H | CH₃ | cyclohexyl | 4-CONHMe-phenyl |
| 123 | H | CH₃ | Ph | Ph |
| 124 | H | CH₃ | CH₂Ph | CH₂Ph |
| 127 | H | CH₃ | 3-OBn-Ph | Ph |
| 128 | H | CH₃ | 3-SO₂NH₂-Ph | Ph |
| 129 | H | CH₃ | 3-OH-Ph | Ph |
| 130 | H | CH₃ | 4-OBn-Ph | Ph |
| 131 | H | CH₃ | 3-NO₂-Ph | 3-OMe-Ph |
| 132 | H | CH₃ | 3-NH₂-Ph | 3-OMe-Ph |
| 133 | H | CH₃ | 3-NO₂-Ph | 3-OH-Ph |
| 134 | H | CH₃ | Ph | 3-OBn-Ph |
| 135 | H | CH₃ | 3-NO₂-Ph | 3-OBn-Ph |
| 136 | H | CH₃ | 3-NO₂-Ph | 3-OBn-Ph |
| 137 | H | CH₃ | 3-OH-Ph | 3-pyridyl |
| 138 | H | CH₃ | 3-NH₂-Ph | 3-Br-Ph |
| 139 | H | CH₃ | 3-NH₂-Ph | 3-OPh-Ph |
| 140 | H | CH₃ | 3-OBn-Ph | 5-Br-3-pyridyl |
| 141 | H | CH₃ | Ph | 3-OPh-Ph |
| 142 | H | CH₃ | 3-OH-Ph | 3-OBn-Ph |
| 143 | H | CH₃ | 3-OH-Ph | 3-OPh-Ph |
| 144 | H | CH₃ | 3-OH-Ph | 3-OH-Ph |
| 145 | H | CH₃ | 3-OH-Ph | 3-Br-Ph |
| 146 | H | CH₃ | 3-OBn-Ph | 3-Br-Ph |
| 147 | H | CH₃ | 3-OH-Ph | 3-(3-OH-Ph)-Ph |
| 148 | H | CH₃ | 3-OH-Ph | 3-(3-OEt-Ph)-Ph |
| 149 | H | CH₃ | 3-OH-Ph | 3-(3-pyridyl)-Ph |
| 150 | H | CH₃ | 3-OBn-Ph | 5-Ph-pyridin-3-yl |
| 151 | H | CH₃ | 3-OBn-Ph | 5-Br-3-pyridyl |
| 152 | H | CH₃ | 3-OBn-Ph | 5-Ph-3-pyridyl |
| 153 | H | CH₃ | 4-OH-Ph | Ph |
| 154 | H | CH₃ | 3-OH-Ph | 5-Ph-pyridin-3-yl |
| 155 | H | CH₃ | 3-OH-Ph | 3-(3-NH₂-Ph)-Ph |
| 156 | H | CH₃ | 3-OH-Ph | 3-(3-Cl,4-F-Ph)-Ph |
| 157 | H | CH₃ | 3-OH-Ph | 3-(4-iPr-Ph)-Ph |
| 158 | H | CH₃ | 3-NO₂-Ph | 5-Ph-pyridin-3-yl |
| 159 | H | CH₃ | 3-OH-Ph | 3-(3-N-Boc-pyrrol-2-yl)-Ph |
| 160 | H | CH₃ | 3-NHSO₂Me-Ph | 3-pyridyl |
| 161 | H | CH₃ | 3-NHSO₂Et-Ph | 3-pyridyl |
| 162 | H | CH₃ | 3-OMe-Ph | Ph |
| 163 | H | CH₃ | 3-SO₂NH₂-Ph | 3-pyridyl |
| 164 | H | CH₃ | 3-OH-Ph | 3-(2-OH-Ph)-Ph |
| 165 | H | CH₃ | 3-OH-Ph | 3-(3-pyrrol-2-yl)-Ph |
| 166 | H | CH₃ | 3-OH-Ph | 3-(6-OMe-pyridin-2-yl)-Ph |
| 167 | H | CH₃ | 3-OH-Ph | 3-(5-OMe-pyridin-2-yl)-Ph |
| 168 | H | CH₃ | 3-OH-Ph | 3-(2,5-Me₂-isoxazol-4-yl)-Ph |
| 169 | H | CH₃ | 3-OH-Ph | 3-(pyridin-4-yl)-Ph |
| 176 | H | CH₂OCH₃ | Ph | 4-Cl-phenyl |
| 177 | H | CH₂OCH₃ | Ph | 4-CF₃-phenyl |
| 178 | H | CH₂OCH₃ | Ph | 4-CH₃-phenyl |
| 179 | H | CH₂OCH₃ | CH₂Ph | pyridin-3-yl |
| 180 | H | CH₂OCH₃ | COPh | 4-Cl-phenyl |
| 181 | H | CH₂OCH₃ | COPh | 4-CF₃-phenyl |
| 182 | H | CH₂OCH₃ | COPh | 4-CH₃-phenyl |
| 183 | H | CH₂OCH₃ | CONHCH₂Ph | 4-Cl-phenyl |
| 184 | H | CH₂OCH₃ | CONHCH₂Ph | 4-CF₃-phenyl |
| 185 | H | CH₂OCH₃ | CONHCH₂Ph | 4-CH₃-phenyl |
| 187 | H | CH₂OCH₃ | Ph | thiazol-2-yl |
| 188 | H | CH₂OCH₃ | cyclohexyl | piperidin-1-yl |
| 189 | H | CH₂OCH₃ | cyclohexyl | 4-CONHMe-phenyl |
| 190 | H | CH₂OCH₃ | CH₂Ph | CH₂Ph |
| 193 | H | CH₂OCH₃ | 3-SO₂NH₂-Ph | Ph |
| 194 | H | CH₂OCH₃ | 3-OH-Ph | Ph |
| 195 | H | CH₂OCH₃ | 4-OBn-Ph | Ph |
| 196 | H | CH₂OCH₃ | 3-NO₂-Ph | 3-OMe-Ph |
| 197 | H | CH₂OCH₃ | 3-NH₂-Ph | 3-OMe-Ph |
| 198 | H | CH₂OCH₃ | 3-NO₂-Ph | 3-OH-Ph |
| 199 | H | CH₂OCH₃ | Ph | 3-OBn-Ph |
| 200 | H | CH₂OCH₃ | 3-NO₂-Ph | 3-OBn-Ph |
| 201 | H | CH₂OCH₃ | 3-NO₂-Ph | 3-OBn-Ph |
| 202 | H | CH₂OCH₃ | 3-OBn-Ph | 3-pyridyl |
| 203 | H | CH₂OCH₃ | 3-OH-Ph | 3-pyridyl |
| 204 | H | CH₂OCH₃ | 3-NH₂-Ph | 3-Br-Ph |
| 205 | H | CH₂OCH₃ | 3-NH₂-Ph | 3-OPh-Ph |
| 206 | H | CH₂OCH₃ | 3-OBn-Ph | 5-Br-3-pyridyl |
| 207 | H | CH₂OCH₃ | Ph | 3-OPh-Ph |
| 208 | H | CH₂OCH₃ | 3-OH-Ph | 3-OBn-Ph |

-continued

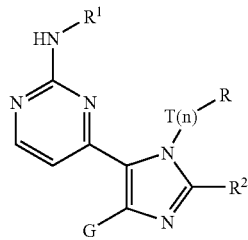

IIa

| No. IIa- | G | —T$_{(n)}$—R | R$^1$ | R$^2$ |
|---|---|---|---|---|
| 209 | H | CH$_2$OCH$_3$ | 3-OH-Ph | 3-OPh-Ph |
| 210 | H | CH$_2$OCH$_3$ | 3-OH-Ph | 3-OH-Ph |
| 211 | H | CH$_2$OCH$_3$ | 3-OH-Ph | 3-Br-Ph |
| 212 | H | CH$_2$OCH$_3$ | 3-OBn-Ph | 3-Br-Ph |
| 213 | H | CH$_2$OCH$_3$ | 3-OH-Ph | 3-(3-OH-Ph)-Ph |
| 214 | H | CH$_2$OCH$_3$ | 3-OH-Ph | 3-(3-OEt-Ph)-Ph |
| 215 | H | CH$_2$OCH$_3$ | 3-OH-Ph | 3-(3-pyridyl)-Ph |
| 216 | H | CH$_2$OCH$_3$ | 3-OBn-Ph | 5-Ph-pyridin-3-yl |
| 217 | H | CH$_2$OCH$_3$ | 3-OBn-Ph | 5-Br-3-pyridyl |
| 218 | H | CH$_2$OCH$_3$ | 3-OBn-Ph | 5-Ph-3-pyridyl |
| 219 | H | CH$_2$OCH$_3$ | 4-OH-Ph | Ph |
| 220 | H | CH$_2$OCH$_3$ | 3-OH-Ph | 5-Ph-pyridin-3-yl |
| 221 | H | CH$_2$OCH$_3$ | 3-OH-Ph | 3-(3-NH$_2$-Ph)-Ph |
| 222 | H | CH$_2$OCH$_3$ | 3-OH-Ph | 3-(3-Cl,4-F-Ph)-Ph |
| 223 | H | CH$_2$OCH$_3$ | 3-OH-Ph | 3-(4-iPr-Ph)-Ph |
| 224 | H | CH$_2$OCH$_3$ | 3-NO$_2$-Ph | 5-Ph-pyridin-3-yl |
| 225 | H | CH$_2$OCH$_3$ | 3-OH-Ph | 3-(3-N-Boc-pyrrol-2-yl)-Ph |
| 226 | H | CH$_2$OCH$_3$ | 3-NHSO$_2$Me-Ph | 3-pyridyl |
| 227 | H | CH$_2$OCH$_3$ | 3-NHSO$_2$Et-Ph | 3-pyridyl |
| 228 | H | CH$_2$OCH$_3$ | 3-SO$_2$NH$_2$-Ph | 3-pyridyl |
| 229 | H | CH$_2$OCH$_3$ | 3-OH-Ph | 3-(2-OH-Ph)-Ph |
| 230 | H | CH$_2$OCH$_3$ | 3-OH-Ph | 3-(3-pyrrol-2-yl)-Ph |
| 231 | H | CH$_2$OCH$_3$ | 3-OH-Ph | 3-(6-OMe-pyridin-2-yl)-Ph |
| 232 | H | CH$_2$OCH$_3$ | 3-OH-Ph | 3-(5-OMe-pyridin-2-yl)-Ph |

-continued

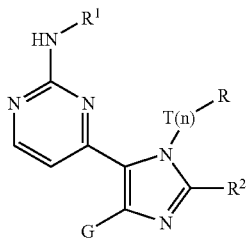

IIa

| No. IIa- | G | —T$_{(n)}$—R | R$^1$ | R$^2$ |
|---|---|---|---|---|
| 233 | H | CH$_2$OCH$_3$ | 3-OH-Ph | 3-(2,5-Me$_2$-isoxazol-4-yl)-Ph |
| 234 | H | CH$_2$OCH$_3$ | 3-OH-Ph | 3-(pyridin-4-yl)-Ph. |

8. A composition comprising a compound according to any one of claims 1, 2, 3, 4, 6, or 7, and a pharmaceutically acceptable carrier, adjuvant, or vehicle.

9. The composition according to claim 8, additionally comprising a therapeutic agent that is an agent for treating cancer.

10. A method of treating or lessening the severity of colon cancer, comprising the step of administering to said patient a composition according to claim 8.

11. The method according to claim 10, comprising the additional step of administering to said patient an additional therapeutic agent that is an anti-proliferative agent, wherein:
said additional therapeutic agent is appropriate for the disease being treated; and
said additional therapeutic agent is administered together with said composition as a single dosage form or separately from said composition as part of a multiple dosage form.

12. A composition for coating an implantable device comprising a compound according to claim 1 and a carrier suitable for coating said implantable device.

\* \* \* \* \*